(12) United States Patent
Patel et al.

(10) Patent No.: US 11,090,289 B2
(45) Date of Patent: Aug. 17, 2021

(54) COMPOSITIONS AND METHODS FOR BLOCKING SODIUM CHANNELS

(71) Applicants: University of Virginia Patent Foundation, Charlottesville, VA (US); Mirko Rivara, San Polo di Torrile (IT)

(72) Inventors: Manoj K. Patel, Charlottesville, VA (US); Mirko Rivara, San Polo di Torrile (IT)

(73) Assignee: University of Virginia Patent Foundation, Charlottesville ( * ) Notice: Subject to any disclaimer, the term of this patent is extended or adjusted under 35 U.S.C. 154(b) by 0 days.

(21) Appl. No.: 16/480,300

(22) PCT Filed: Jan. 24, 2018

(86) PCT No.: PCT/US2018/015059
§ 371 (c)(1),
(2) Date: Jul. 23, 2019

(87) PCT Pub. No.: WO2018/140504
PCT Pub. Date: Aug. 2, 2018

(65) Prior Publication Data
US 2019/0365714 A1 Dec. 5, 2019

Related U.S. Application Data

(60) Provisional application No. 62/449,812, filed on Jan. 24, 2017.

(51) Int. Cl.
*A61K 31/4164* (2006.01)
*A61K 31/4184* (2006.01)
*A61P 25/08* (2006.01)

(52) U.S. Cl.
CPC ...... *A61K 31/4164* (2013.01); *A61K 31/4184* (2013.01); *A61P 25/08* (2018.01)

(58) Field of Classification Search
None
See application file for complete search history.

(56) References Cited

U.S. PATENT DOCUMENTS

| 4,424,229 | A | 1/1984 | Jorgensen et al. | |
|---|---|---|---|---|
| 6,632,828 | B2 | 10/2003 | Stamford et al. | |
| 6,737,418 | B2 | 5/2004 | Hogenkamp et al. | |
| 2002/0028798 | A1* | 3/2002 | Demopulos | A61K 31/4439 514/210.2 |
| 2004/0229927 | A1 | 11/2004 | Sircar et al. | |
| 2010/0256165 | A1* | 10/2010 | Hongu | A61P 9/12 514/255.05 |

FOREIGN PATENT DOCUMENTS

| CN | 1944414 | A | 4/2007 |
|---|---|---|---|
| CN | 104606192 | A | 5/2015 |
| CN | 104844518 | A | 8/2015 |
| DE | 297816 | A5 | 1/1992 |
| DE | 102008000237 | A1 | 8/2008 |
| EP | 1605078 | A1 | 12/2005 |
| JP | 2004277386 | A | 10/2004 |
| JP | 2005349439 | A | 12/2005 |
| JP | 2014040395 | A | 3/2014 |
| WO | WO-02083111 | A2 | 10/2002 |
| WO | WO-2007021941 | A2 | 2/2007 |
| WO | WO-2018140504 | A1 | 8/2018 |

OTHER PUBLICATIONS

Shavkunov, Alexander. Bioluminescence Methodology for the Detection of Protein-Protein Interactions Within the Voltage-Gated Sodium Channel Macromolecular Complex. Assay and Drug Development Technologies. 10(2), Apr. 2012.*
Puratchikody, Ayarivan. QSAR Studies on Antiepileptic and Locomotor in vivo Activities of 4,5-diphenyl-1H-Imidazoles. Chem. Biol. Drug. Des. 2009, 74, 173-182.*
Shavkunov, Alexander. Bioluminescence Methodology for the Detection or Protein-Protein Interactions Within the Voltage-Gated Sodium Channel Macromolecular Complex. Assay and Drug Development Technologies, 10(2), 2012, 148-160.*
"European Application Serial No. 18744497.1, Response filed Feb. 12, 2020 to Communication pursuant to Rules 161(2) and 162 EPC dated Sep. 6, 2019", 19 pgs.
"International Application Serial No. PCT/US2018/015059, International Preliminary Report on Patentability dated Aug. 8, 2019", 7 pgs.
WO-4424229, Jan. 1984, Jorgensen, Dan, et al.
"2,4(5)-Diarylimidazoles as inhibitors of hNaV1.2 sodium channels: Pharmacological evaluation and structureproperty relationships", Bioorganic & Medicinal Chemistry vol. 17, (2009), 3642-3648.
"International Application Serial No. PCT/US2018/015059, International Search Report dated Jun. 29, 2018", 4 pgs.
"International Application Serial No. PCT/US2018/015059, Invitation to Pay Add'l Fees and Partial Search Report dated Mar. 22, 2018", 3 pgs.
"International Application Serial No. PCT/US2018/015059, Written Opinion dated Jun. 29, 2018", 5 pgs.
Zuliani, Valentina, et al., "Anticonvulsant activity of 2,4(1H)-diarylimidazoles in mice and rats acute seizure models", Bioorg. Med. Chem. 18 (2010), (2010), 7957-7965.
"European Application Serial No. 18744497.1, Extended European Search Report dated Oct. 6, 2020", 21 pgs.

(Continued)

*Primary Examiner* — Samantha L Shterengarts
(74) *Attorney, Agent, or Firm* — Schwegman Lundberg & Woessner, P.A.

(57) ABSTRACT

The disclosure provides methods for treating a subject suffering from a disease associated with sodium channel activity. The method comprises administering to the subject a therapeutically effective amount of a compound according to Formula II or Formula III described in the specification, or a pharmaceutically acceptable salt, prodrug, tautomer, stereoisomer, hydrate, or solvate thereof.

5 Claims, 14 Drawing Sheets

(56) References Cited

OTHER PUBLICATIONS

"European Application Serial No. 18744497.1, Partial supplementary European search report dated Jul. 1, 2020", 23 pgs.

Guo, Xiao, et al., "Highly efficient and eco-friendly protocol to functionalized imidazoles via ring-opening of [alpha]-nitro epoxides", RSC Advances, vol. 5, No. 64, (Jan. 2015), 51559-51562.

Mitra, Shubhanjan, et al., "Nano indium oxide catalyzed tandem cyclization of amidine with nitroolefin", Tetrahedron Letters, vol. 54, No. 36, (Jul. 16, 2013), 4982-4985.

Murthy, S N, et al., "DABCO as a mild and efficient catalytic system for the synthesis of highly substituted imidazoles via multi-component condensation strategy", Tetrahedron Letters, vol. 51, No. 40, (Oct. 6, 2010), 5252-5257.

Nagalakshmi, G, "Synthesis and Pharmacological Evaluation of 2-(4-Halosubstituted phenyl)-4,5-diphenyl-1 H -imidazoles", E-Journal of Chemistry, vol. 5, No. 3, (Jan. 2008), 447-452.

Rivara, M, et al., "2,4(5)-Diarylimidazoles: Synthesis and biological evaluation of a new class of sodium channel blockers against hNa"v1.2", Bioorganic and Medicinal Chemistry Letters, vol. 18, No. 20, (Oct. 15, 2008), 5460-5462.

Rivara, M., et al., "In vivo screening of diaryl imidazoles as anticonvulsant agents", Medicinal Chemistry Research, vol. 21, No. 11, (Nov. 19, 2011), 3428-3434.

Rivara, Mirko, et al., "Inhibition of NaV1.6 sodium channel currents by a novel series of 1,4-disubstituted-triazole derivatives obtained via copper-catalyzed click chemistry", Bioorganic and Medicinal Chemistry Letters, vol. 22, No. 20, (2012), 6401-6404.

Xie, Zeqiang, et al., "Copper-mediated C(sp 3 )-H azidation with Me 3 SiN 3 : synthesis of imidazoles from ketones and aldehydes", Chemical Communications, vol. 52, No. 38, (Jan. 2016), 6467-6470.

\* cited by examiner

COMPOSITIONS AND METHODS FOR BLOCKING SODIUM CHANNELS

RELATED APPLICATIONS

This application is a U.S. National Stage Filing under 35 U.S.C. 371 from International Application No. PCT/US2018/015059, filed on Jan. 24, 2018, and published as WO 2018/140504, which claims the benefit of priority to U.S. Provisional Patent Application No. 62/449,812 filed on Jan. 24, 2017, the disclosures of which are incorporated herein in their entireties by reference.

BACKGROUND

Epilepsy, a neurological disorder, is characterized by recurrent spontaneous seizures within the brain and is a major public health issue affecting over 2 million Americans. In the United States, 1 in 26 people will develop epilepsy in their lifetime. Current treatments for epilepsy involve the suppression of seizure's using antiepileptic drugs (AEDs). Unfortunately, substantial proportions of patients (~30%) continue to experience seizures even in the presence of optimal doses of AEDs and are considered pharmaco-resistant. Furthermore, many patients that achieve seizure control with medications suffer from medication induced neurotoxicity, sedation, and cognitive side effects (see, for example, Rivara M et al (2008) Bioorg Med Chem 18, 5460-62; Fantini M et al (2009) Bioorg Med Chem 17, 3642-48; Zuliani V et al (2010) Bioorg Med Chem 18, 7957-65; Rivara M et al (2012) Bioorg Med Chem Lett 22, 6401-04). In view of this, there is a continued need for the development of more effective and safer AEDs.

There is a long felt need in the art for compositions and methods useful for treating diseases and disorders associated with involvement of sodium channels, including epilepsy. The present invention satisfies these needs.

SUMMARY OF THE INVENTION

The present invention provides compounds useful for the treatment of diseases and disorders associated with voltage-gated sodium channel dysfunction. The diseases and disorders include epilepsy and other seizure disorders, chronic pain and neuropathic pain. Various compounds of the present invention are selective to certain isoforms of sodium channel, e.g., NaV1.6. and some are selective for the certain state of the NaV1.6 sodium channel, e.g., inactive state. Such properties can result in advantageous state-dependent or use-dependent activity. Compounds herein can be effective even for challenging therapy resistant scenarios where current clinical options are ineffective. Compounds of the present invention include aryl substituted oxazoles, thiazoles, imidazoles, benzoxazoles, benzothiazoles and benzimidazoles. In some embodiments, the compounds are aryl substituted imidazoles and aryl substituted benzimidazoles. The present invention further relates to treatment methods and compositions involving the compounds provided herein.

The present invention provides a method for treating a subject suffering from a disease associated with sodium channel activity, the method comprising administering to the subject a therapeutically effective amount of a compound according to Formula II or Formula III, or a pharmaceutically acceptable salt, prodrug, tautomer, stereoisomer, hydrate, or solvate thereof:

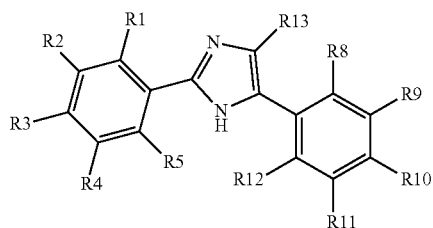

Formula II wherein

R1, R2, R3, R4, R5, R8 and R12 in each occurrence is independently H, $CH_3$, F, Cl, Br, I, $OCH_3$, $CF_3$, $OCF_3$, $NH_2$, COOH, CHO, OH, SH, $NO_2$, $COCH_3$, $CONH_2$, or $NHCOCH_3$;

R9, R10 and R11 each is independently H, $CH_3$, F, Cl, Br, I, $OCH_3$, $CF_3$, $OCF_3$, $NH_2$, COOH, CHO, OH, SH, $NO_2$, $COCH_3$, $CONH_2$, $NHCOCH_3$, or

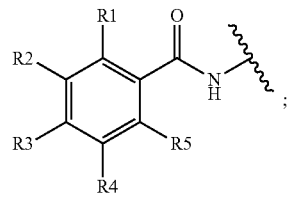

R13 is H, optionally substituted $C_1$-$C_6$ alkyl, optionally substituted $C_1$-$C_6$ haloalkyl, optionally substituted $C_6$-$C_{10}$ aryl, optionally substituted 5, 6, 7, 8 and 9-membered heteroaryl, or halogen; and when R13 is H then R9, R10 or R11 is

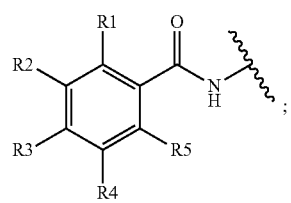

and

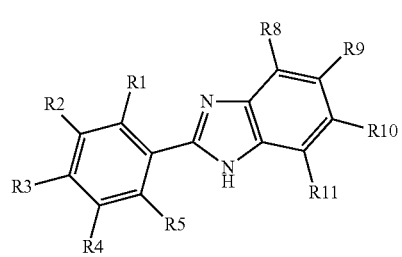

Formula III wherein

R1, R2, R4 and R5 each is independently H, $OCH_3$, $CF_3$, $OCF_3$, $NH_2$, COOH, CHO, OH, SH, $COCH_3$, $CONH_2$, or $NHCOCH_3$;

R3 is H;

R8 and R11 each is independently H, CH$_3$, F, Cl, Br, I, OCH$_3$, CF$_3$, OCF$_3$, NH$_2$, COOH, CHO, OH, SH, NO$_2$, COCH$_3$, CONH$_2$, or NHCOCH$_3$;

R9 is F, Cl, Br, I, NO$_2$, or CF$_3$; and

R10 is H.

The present invention also provides a pharmaceutical composition comprising a pharmaceutically acceptable carrier and a therapeutically effective amount of a compound according to Formula II or Formula III, or a pharmaceutically acceptable salt, prodrug, tautomer, stereoisomer, hydrate, or solvate thereof:

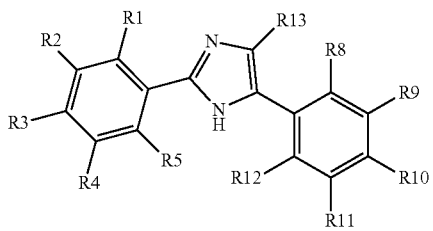

Formula II wherein

R1, R2, R3, R4, R5, R8 and R12 in each occurrence is independently H, CH$_3$, F, Cl, Br, I, OCH$_3$, CF$_3$, OCF$_3$, NH$_2$, COOH, CHO, OH, SH, NO$_2$, COCH$_3$, CONH$_2$, or NHCOCH$_3$;

R9, R10 and R11 each is independently H, CH$_3$, F, Cl, Br, I, OCH$_3$, CF$_3$, OCF$_3$, NH$_2$, COOH, CHO, OH, SH, NO$_2$, COCH$_3$, CONH$_2$, NHCOCH$_3$, or

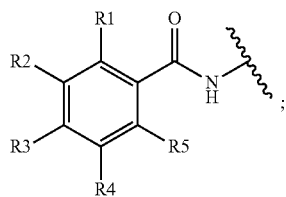

R13 is H, optionally substituted C$_1$-C$_6$ alkyl, optionally substituted C$_1$-C$_6$ haloalkyl, optionally substituted C$_6$-C$_{10}$ aryl, optionally substituted 5, 6, 7, 8 and 9-membered heteroaryl, or halogen; and when R13 is H then R9, R10 or R11 is

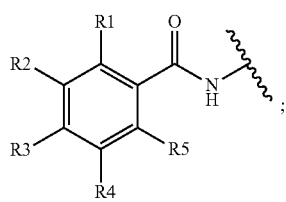

and

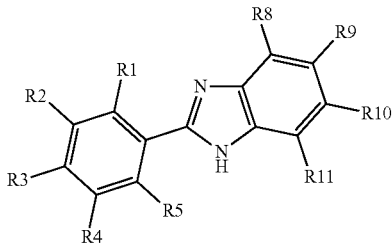

Formula III wherein

R1, R2, R4 and R5 each is independently H, OCH$_3$, CF$_3$, OCF$_3$, NH$_2$, COOH, CHO, OH, SH, COCH$_3$, CONH$_2$, or NHCOCH$_3$;

R3 is H;

R8 and R11 each is independently H, CH$_3$, F, Cl, Br, I, OCH$_3$, CF$_3$, OCF$_3$, NH$_2$, COOH, CHO, OH, SH, NO$_2$, COCH$_3$, CONH$_2$, or NHCOCH$_3$;

R9 is F, Cl, Br, I, NO$_2$, or CF$_3$; and

R10 is H.

The present invention also provides a compound according to Formula II, or a pharmaceutically acceptable salt, prodrug, tautomer, stereoisomer, hydrate, or solvate thereof:

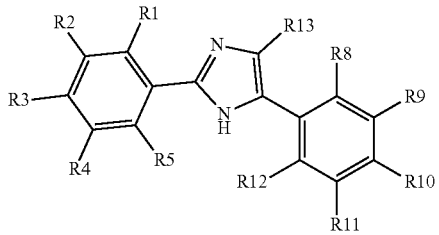

Formula II wherein

R1, R2, R4, R5, R8 and R12 in each occurrence is independently H, CH$_3$, F, Br, I, OCH$_3$, CF$_3$, OCF$_3$, NH$_2$, COOH, CHO, OH, SH, NO$_2$, COCH$_3$, CONH$_2$, or NHCOCH$_3$;

R3 is H, CH$_3$, F, Cl, Br, I, OCH$_3$, CF$_3$, OCF$_3$, NH$_2$, COOH, CHO, OH, SH, NO$_2$, COCH$_3$, CONH$_2$, or NHCOCH$_3$;

R9, R10 and R11 each is independently H, CH$_3$, F, Cl, Br, I, OCH$_3$, CF$_3$, OCF$_3$, NH$_2$, COOH, CHO, OH, SH, NO$_2$, COCH$_3$, CONH$_2$, NHCOCH$_3$, or

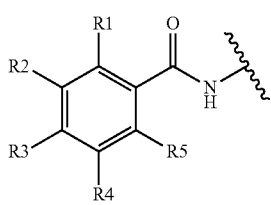

R13 is H, optionally substituted C$_1$-C$_6$ alkyl, optionally substituted C$_1$-C$_6$ haloalkyl, optionally substituted C$_6$-C$_{10}$ aryl, optionally substituted 5, 6, 7, 8 and 9-membered heteroaryl, or halogen; and wherein when R13 is H then R9, R10 or R11 is

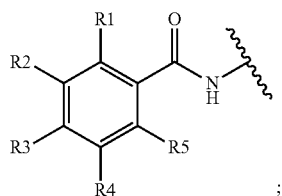

and
wherein when R13 is CH$_3$ then R3 is H.

In some embodiments, the compounds disclosed herein advantageously mimic the effects of clinically active anti-epilepsy drugs (AEDs). For example, some compounds delay sodium channel recovery from inactivation. Some compounds disclosed herein can function as use-dependent blockers which is an advantageous characteristic for AEDs as it allows increased inhibition of sodium channels during increased neuronal activity, such as during seizures. As disclosed herein, compounds that are potentially effective for treating both acute and chronic seizures were identified by use of the NIH ADDS screening program for AED activity and through the following tests: MES, ScMET, 32 mA 6 Hz Psychomotor test, and 44 mA 6 Hz Psychomotor test. Successful performance of these compounds in the 6 Hz psychomotor tests in comparison with current treatment compounds indicates that some of the compounds disclosed herein have an ability to treat therapy resistant seizure disorders, including therapy resistant epilepsy. Some compounds advantageous neurotoxicity profiles. For example, one compound displayed little to no neurotoxicity at concentrations ranging up to 600 mg/kg, which represents a significantly higher tolerance in vivo compared to tolerances for current therapeutic options.

The present invention provides compounds of formula I or a tautomer thereof, or a pharmaceutically acceptable salt or solvate of said compound or said tautomer.

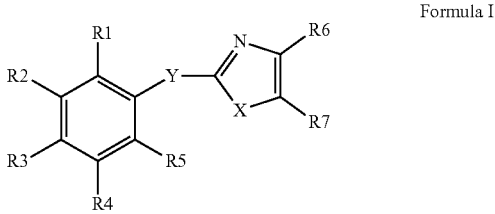

Formula I

Various aspects and embodiments of the invention are described in further detail below.

DETAILED DESCRIPTION OF THE INVENTION

Figure 1:
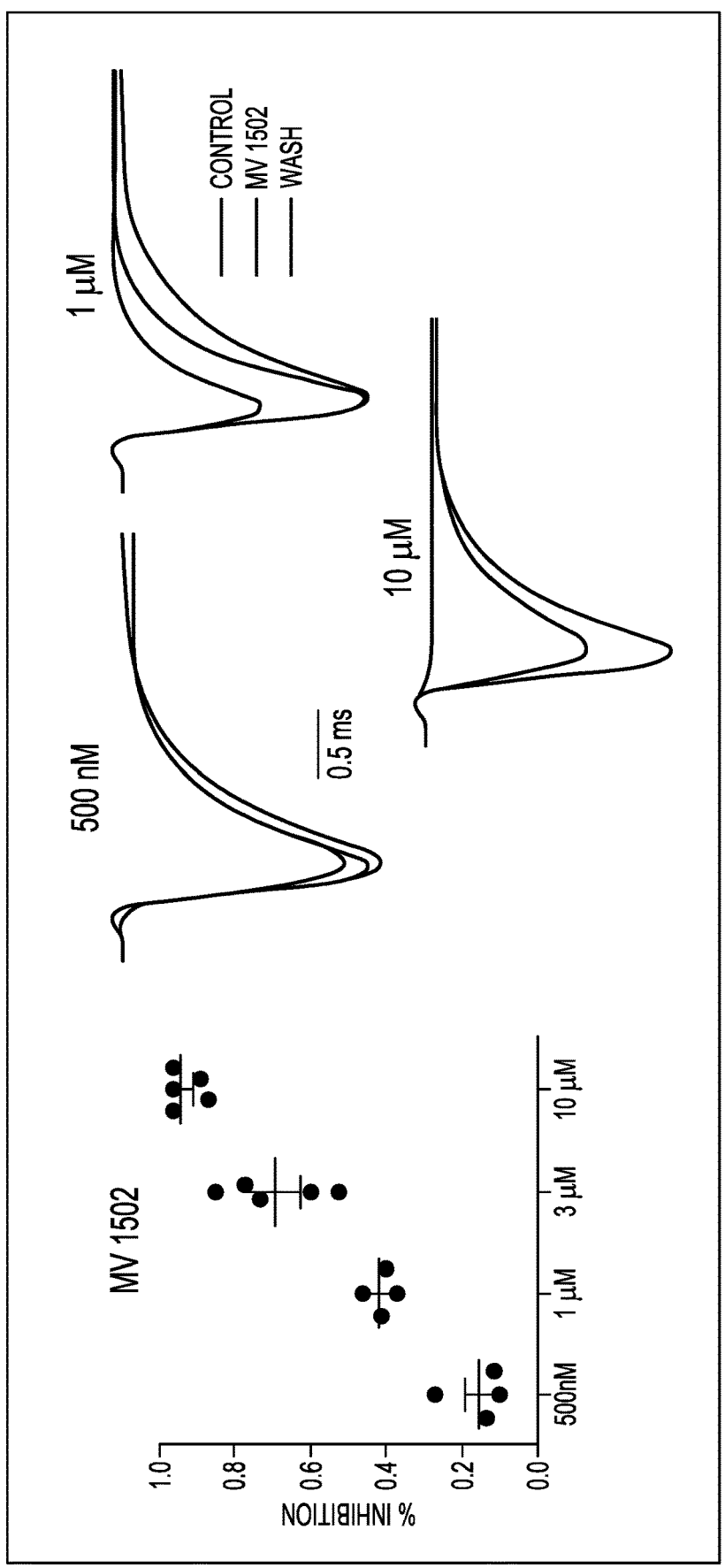
FIG. 1 shows a scatter plot depicting dose response of MV1502 and activation over time curves for MV1502 (light color line, top) compared to a wash (medium color line, middle) and a control (dark color line, bottom) at 500 nM, 1 µM and 10 µM.

Reference will now be made in detail to certain embodiments of the disclosed subject matter. While the disclosed subject matter will be described in conjunction with the enumerated claims, it will be understood that the exemplified subject matter is not intended to limit the claims to the disclosed subject matter.

Definition of Terms

In describing and claiming the invention, the following terminology will be used in accordance with the definitions set forth below. Unless defined otherwise, all technical and scientific terms used herein have the commonly understood by one of ordinary skill in the art to which the invention pertains. Although any methods and materials similar or equivalent to those described herein may be useful in the practice or testing of the present invention, certain methods and materials are described below. Specific terminology of particular importance to the description of the present invention is defined below.

The articles "a" and "an" are used herein to refer to one or to more than one (i.e., to at least one) of the grammatical object of the article. By way of example, "an element" means one element or more than one element.

The term "about," as used herein, means approximately, in the region of, roughly, or around. When the term "about" is used in conjunction with a numerical range, it modifies that range by extending the boundaries above and below the numerical values set forth. For example, in one aspect, the term "about" is used herein to modify a numerical value above and below the stated value by a variance of 10%.

The terms "additional therapeutically active compound" or "additional therapeutic agent", as used in the context of the present invention, refers to the use or administration of a compound for an additional therapeutic use for a particular injury, disease, or disorder being treated. Such a compound, for example, could include one being used to treat an unrelated disease or disorder, or a disease or disorder which may not be responsive to the primary treatment for the injury, disease or disorder being treated.

As use herein, the terms "administration of" and or "administering" a compound should be understood to mean providing a compound of the invention or a prodrug of a compound of the invention to a subject in need of treatment.

As used herein, an "agonist" is a composition of matter which, when administered to a mammal such as a human, enhances or extends a biological activity attributable to the level or presence of a target compound or molecule of interest in the subject.

As used herein, "alleviating a disease or disorder symptom," means reducing the severity of the symptom or the frequency with which such a symptom is experienced by a subject, or both.

As used herein, an "analog", or "analogue" of a chemical compound is a compound that, by way of example, resembles another in structure but is not necessarily an isomer (e.g., 5-fluorouracil is an analog of thymine).

An "antagonist" is a composition of matter which when administered to a mammal such as a human, inhibits a biological activity attributable to the level or presence of a compound or molecule of interest in the subject.

The term "antimicrobial agents" as used herein refers to any naturally-occurring, synthetic, or semi-synthetic compound or composition or mixture thereof, which is safe for human or animal use as practiced in the methods of this invention, and is effective in killing or substantially inhibiting the growth of microbes. "Antimicrobial" as used herein, includes antibacterial, antifungal, and antiviral agents.

The term "basic" or "positively charged" amino acid, as used herein, refers to amino acids in which the R groups have a net positive charge at pH 7.0, and include, but are not limited to, the standard amino acids lysine, arginine, and histidine.

The term bioactive is used interchangeably with "biologically active" and "functional".

The term "biocompatible," as used herein, refers to a material that does not elicit a substantial detrimental response in the host.

The term "biological sample," as used herein, refers to samples obtained from a living organism, including skin, hair, tissue, blood, plasma, cells, sweat, and urine.

The terms "cell" and "cell line," as used herein, may be used interchangeably. All of these terms also include their progeny, which are any and all subsequent generations. It is understood that all progeny may not be identical due to deliberate or inadvertent mutations.

The terms "cell culture" and "culture," as used herein, refer to the maintenance of cells in an artificial, in vitro environment. It is to be understood, however, that the term "cell culture" is a generic term and may be used to encompass the cultivation not only of individual cells, but also of tissues, organs, organ systems or whole organisms, for which the terms "tissue culture," "organ culture," "organ system culture" or "organotypic culture" may occasionally be used interchangeably with the term "cell culture."

The phrases "cell culture medium," "culture medium" (plural "media" in each case) and "medium formulation" refer to a nutritive solution for cultivating cells and may be used interchangeably.

By "chemically feasible" is meant a bonding arrangement or a compound where the generally understood rules of organic structure are not violated; for example a structure within a definition of a claim that would contain in certain situations a pentavalent carbon atom that would not exist in nature would be understood to not be within the claim. The structures disclosed herein, in all of their embodiments are intended to include only "chemically feasible" structures, and any recited structures that are not chemically feasible, for example in a structure shown with variable atoms or groups, are not intended to be disclosed or claimed herein.

When a substituent is specified to be an atom or atoms of specified identity, "or a bond", a configuration is referred to when the substituent is "a bond" that the groups that are immediately adjacent to the specified substituent are directly connected to each other in a chemically feasible bonding configuration.

All chiral, diastereomeric, racemic forms of a structure are intended, unless a particular stereochemistry or isomeric form is specifically indicated. Compounds used in the present invention can include enriched or resolved optical isomers at any or all asymmetric atoms as are apparent from the depictions, at any degree of enrichment. Both racemic and diastereomeric mixtures, as well as the individual optical isomers can be isolated or synthesized so as to be substantially free of their enantiomeric or diastereomeric partners, and these are all within the scope of the invention.

A "compound," as used herein, refers to any type of substance or agent that is commonly considered a drug, or a candidate for use as a drug, as well as combinations and mixtures of the above. When referring to a compound of the invention, and unless otherwise specified, the term "compound" is intended to encompass not only the specified molecular entity but also its pharmaceutically acceptable, pharmacologically active analogs, including, but not limited to, salts, polymorphs, esters, amides, prodrugs, adducts, conjugates, active metabolites, and the like, where such modifications to the molecular entity are appropriate.

The term "delivery vehicle" refers to any kind of device or material which can be used to deliver compounds in vivo or can be added to a composition comprising compounds administered to a plant or animal. This includes, but is not limited to, implantable devices, aggregates of cells, matrix materials, gels, etc.

As used herein, a "derivative" of a compound refers to a chemical compound that may be produced from another compound of similar structure in one or more steps, as in replacement of H by an alkyl, acyl, or amino group.

The use of the word "detect" and its grammatical variants is meant to refer to measurement of the species without quantification, whereas use of the word "determine" or "measure" with their grammatical variants are meant to refer to measurement of the species with quantification. The terms "detect" and "identify" are used interchangeably herein.

As used herein, a "detectable marker" or a "reporter molecule" is an atom or a molecule that permits the specific detection of a compound comprising the marker in the presence of similar compounds without a marker. Detectable markers or reporter molecules include, e.g., radioactive isotopes, antigenic determinants, enzymes, nucleic acids available for hybridization, chromophores, fluorophores, chemiluminescent molecules, electrochemically detectable molecules, and molecules that provide for altered fluorescence polarization or altered light scattering.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" if the severity of a symptom of the disease or disorder, the frequency with which such a symptom is experienced by a subject, or both, are reduced.

As used herein, an "effective amount" or "therapeutically effective amount" means an amount sufficient to produce a selected effect, such as alleviating symptoms of a disease or disorder. In the context of administering compounds in the form of a combination, such as multiple compounds, the amount of each compound, when administered in combination with another compound(s), may be different from when that compound is administered alone. Thus, an effective amount of a combination of compounds refers collectively to the combination as a whole, although the actual amounts of each compound may vary. The term "more effective" means that the selected effect is alleviated to a greater extent by one treatment relative to the second treatment to which it is being compared. A "therapeutically effective amount" of a compound is also that amount of compound which is sufficient to provide a beneficial effect to the subject to which the compound is administered.

As used in the specification and the appended claims, the terms "for example," "for instance," "such as," "including" and the like are meant to introduce examples that further clarify more general subject matter. Unless otherwise specified, these examples are provided only as an aid for understanding the invention, and are not meant to be limiting in any fashion.

The terms "formula" and "structure" are used interchangeably herein.

As used herein, a "functional" molecule is a molecule in a form in which it exhibits a property or activity by which it is characterized. A functional enzyme, for example, is one that exhibits the characteristic catalytic activity by which the enzyme is characterized.

A "heavy atom" as the term is used herein refers to an atom of an element with an atomic mass greater than that of argon.

As used herein, "homology" is used synonymously with "identity."

The term "ingredient" refers to any compound, whether of chemical or biological origin, that can be used in cell culture media to maintain or promote the growth or proliferation of cells. The terms "component," "nutrient" and "ingredient" can be used interchangeably and are all meant to refer to such compounds. Typical non-limiting ingredients that are used in cell culture media include amino acids, salts, metals, sugars, lipids, nucleic acids, hormones, vitamins, fatty acids, proteins and the like. Other ingredients that promote or maintain cultivation of cells ex vivo can be selected by those of skill in the art, in accordance with the particular need.

The term "inhibit," as used herein, refers to the ability of a compound of the invention to reduce or impede a described function, such as, for example, having activity against cell proliferation or activity against an enzyme. Inhibition may be by at least 10%, may be by at least 25%, may be by at least 50%, and may be inhibited by at least 75%. The terms "inhibit", "reduce", and "block" are used interchangeably herein.

As used herein "injecting or applying" includes administration of a compound of the invention by any number of routes and means including, but not limited to, topical, oral, buccal, intravenous, intramuscular, intra-arterial, intramedullary, intrathecal, intraventricular, transdermal, subcutaneous, intraperitoneal, intranasal, enteral, topical, sublingual, vaginal, ophthalmic, pulmonary, or rectal means.

As used herein, an "instructional material" includes a publication, a recording, a diagram, or any other medium of expression which can be used to communicate the usefulness of the peptide of the invention in the kit for effecting alleviation of the various diseases or disorders recited herein. Optionally, or alternately, the instructional material may describe one or more methods of alleviating the diseases or disorders in a cell or a tissue of a mammal. The instructional material of the kit of the invention may, for example, be affixed to a container which contains the identified compound invention or be shipped together with a container which contains the identified compound. Alternatively, the instructional material may be shipped separately from the container with the intention that the instructional material and the compound be used cooperatively by the recipient.

As used herein, the term "linkage" refers to a connection between two groups. The connection can be either covalent or non-covalent, including but not limited to ionic bonds, hydrogen bonding, and hydrophobic/hydrophilic interactions.

As used herein, the term "linker" refers to a molecule that joins two other molecules either covalently or noncovalently, e.g., through ionic or hydrogen bonds or van der Waals interactions.

The term "modulate", as used herein, refers to changing the level of an activity, function, or process. The term "modulate" encompasses both inhibiting and stimulating an activity, function, or process.

As used herein, the term "pharmaceutically acceptable carrier" includes any of the standard pharmaceutical carriers, such as a phosphate buffered saline solution, water, emulsions such as an oil/water or water/oil emulsion, and various types of wetting agents. The term also encompasses any of the agents approved by a regulatory agency of the US Federal government or listed in the US Pharmacopeia for use in animals, including humans.

"Plurality" means at least two.

The term "prevent," as used herein, means to stop something from happening, or taking advance measures against something possible or probable from happening. In the context of medicine, "prevention" generally refers to action taken to decrease the chance of getting a disease or condition.

A "preventive" or "prophylactic" treatment is a treatment administered to a subject who does not exhibit signs, or exhibits only early signs, of a disease or disorder. A prophylactic or preventative treatment is administered for the purpose of decreasing the risk of developing pathology associated with developing the disease or disorder.

A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug, or may demonstrate increased palatability or be easier to formulate.

As used herein, the term "purified" and like terms relate to an enrichment of a molecule or compound relative to other components normally associated with the molecule or compound in a native environment. The term "purified" does not necessarily indicate that complete purity of the particular molecule has been achieved during the process. A "highly purified" compound as used herein refers to a compound that is greater than 90% pure.

The term "regulate" refers to either stimulating or inhibiting a function or activity of interest.

A "salt" as is well known in the art includes an organic compound such as a carboxylic acid, a sulfonic acid, or an amine, in ionic form, in combination with a counterion. For example, acids in their anionic form can form salts with cations such as metal cations, for example sodium, potassium, and the like; with ammonium salts such as NH4+ or the cations of various amines, including tetraalkyl ammonium salts such as tetramethylammonium, or other cations such as trimethylsulfonium, and the like. Other salt-forming ions include triflate, tosylate, PF6−, BF4−, and BPh4−.

A "sample," as used herein, refers typically to a biological sample from a subject, including, but not limited to, normal tissue samples, diseased tissue samples, biopsies, blood, saliva, feces, semen, tears, and urine. A sample can also be any other source of material obtained from a subject which contains cells, tissues, or fluid of interest. A sample can also be obtained from cell or tissue culture.

A "solid-state" composition, as the term is used herein, refers to a material that is a solid at the temperature examined (usually room temperature, about 20° C.), that is not dissolved in a liquid solvent but is in the physical state of a solid, which can be amorphous, crystalline, in a film, in bulk, and so forth.

A "solvate" refers to an association or complex of one or more solvent molecules and a compound of the present invention. Examples of solvents that form solvates include water, isopropanol, ethanol, methanol, DMSO, ethyl acetate, acetic acid, and ethanolamine. The term "hydrate" refers to the complex where the solvent molecule is water.

The term "standard," as used herein, refers to something used for comparison. For example, a standard can be a known standard agent or compound which is administered or added to a control sample and used for comparing results when measuring said compound in a test sample. Standard can also refer to an "internal standard," such as an agent or compound which is added at known amounts to a sample and is useful in determining such things as purification or recovery rates when a sample is processed or subjected to purification or extraction procedures before a marker of interest is measured.

A "subject" of diagnosis or treatment is a mammal, including a human, as well as other organisms of interest.

The term "symptom," as used herein, refers to any morbid phenomenon or departure from the normal in structure, function, or sensation, experienced by the patient and indicative of disease. In contrast, a "sign" is objective evidence of disease. For example, a bloody nose is a sign. It is evident to the patient, doctor, nurse and other observers.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

A "therapeutic" treatment is a treatment administered to a subject who exhibits signs of pathology for the purpose of diminishing or eliminating those signs.

As used herein, the term "treating" includes prophylaxis of the specific disease, disorder, or condition, or alleviation of the symptoms associated with a specific disease, disorder, or condition and/or preventing or eliminating said symptoms.

As used herein, the term "wound" relates to a physical tear, break, or rupture to a tissue or cell layer. A wound may occur by any physical insult, including a surgical procedure or as a result of a disease, disorder condition.

Chemical Definitions

As used herein, the term "halogen" or "halo" includes bromo, chloro, fluoro, and iodo.

The term "haloalkyl" as used herein refers to an alkyl radical bearing at least one halogen substituent, for example, chloromethyl, fluoroethyl or trifluoromethyl and the like.

The term "$C_1$-$C_n$ alkyl" wherein n is an integer, as used herein, represents a branched or linear alkyl group having from one to the specified number of carbon atoms. Typically, $C_1$-$C_6$ alkyl groups include, but are not limited to, methyl, ethyl, n-propyl, iso-propyl, butyl, iso-butyl, sec-butyl, tert-butyl, pentyl, hexyl, and the like.

The term "$C_2$-$C_n$ alkenyl" wherein n is an integer, as used herein, represents an olefinically unsaturated branched or linear group having from 2 to the specified number of carbon atoms and at least one double bond. Examples of such groups include, but are not limited to, 1-propenyl, 2-propenyl, 1,3-butadienyl, 1-butenyl, hexenyl, pentenyl, and the like.

The term "$C_2$-$C_n$ alkynyl" wherein n is an integer refers to an unsaturated branched or linear group having from 2 to the specified number of carbon atoms and at least one triple bond. Examples of such groups include, but are not limited to, 1-propynyl, 2-propynyl, 1-butynyl, 2-butynyl, 1-pentynyl, and the like.

The term "$C_3$-$C_n$ cycloalkyl" wherein n=8, represents cyclopropyl, cyclobutyl, cyclopentyl, cyclohexyl, cycloheptyl, and cyclooctyl.

As used herein, the term "optionally substituted" typically refers to from zero to four substituents, wherein the substituents are each independently selected. Each of the independently selected substituents may be the same or different than other substituents. For example, the substituents of an R group of a formula may be optionally substituted (e.g., from 1 to 4 times) with independently selected H, halogen, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain and amino acid. As another example, an R group which is optionally substituted may be substituted with H, CH₃, F, Cl, Br, I, OCH₃, CF₃, OCF₃, NH₂, COOH, CHO, OH, SH, NO₂, COCH₃, CONH₂, or NHCOCH₃. As another example, an R group which is optionally substituted may be substituted with a

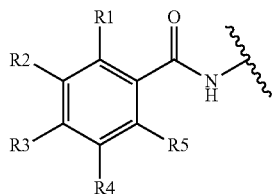

group, where R1, R2, R3, R4 and R5 in each occurrence is independently H, OCH₃, CF₃, OCF₃, NH₂, COOH, CHO, OH, SH, COCH₃, CONH₂, or NHCOCH₃.

As used herein the term "aryl" refers to an optionally substituted mono or bicyclic carbocyclic ring system having one or two aromatic rings including, but not limited to, phenyl, benzyl, naphthyl, tetrahydronaphthyl, indanyl, indenyl, and the like. Optionally substituted aryl includes aryl compounds having from zero to four substituents, and substituted aryl includes aryl compounds having one or more substituents. The term (C₅-C₈ alkyl)aryl refers to any aryl group which is attached to the parent moiety via the alkyl group.

"Heterocycle" refers to any stable 4, 5, 6, 7, 8, 9, 10, 11, or 12 membered, (unless the number of members is otherwise recited), monocyclic, bicyclic, or tricyclic heterocyclic ring that is saturated or partially unsaturated, and which consists of carbon atoms and 1, 2, 3, or 4 heteroatoms independently selected from the group consisting of N, O, and S. If the heterocycle is defined by the number of carbons atoms, then from 1, 2, 3, or 4 of the listed carbon atoms are replaced by a heteroatom. If the heterocycle is bicyclic or tricyclic, then at least one of the two or three rings must contain a heteroatom, though both or all three may each contain one or more heteroatoms. The N group may be N, NH, or N-substituent, depending on the chosen ring and if substituents are recited. The nitrogen and sulfur heteroatoms optionally may be oxidized (e.g., S, S(O), S(O)₂, and N—O). The heterocycle may be attached to its pendant group at any heteroatom or carbon atom that results in a stable structure. The heterocycles described herein may be substituted on carbon or on a nitrogen atom if the resulting compound is stable.

"Heteroaryl" refers to any stable 5, 6, 7, 8, 9, 10, 11, or 12 membered, (unless the number of members is otherwise recited), monocyclic, bicyclic, or tricyclic heterocyclic ring that is aromatic, and which consists of carbon atoms and 1, 2, 3, or 4 heteroatoms independently selected from the group consisting of N, O, and S. If the heteroaryl is defined by the number of carbons atoms, then 1, 2, 3, or 4 of the listed carbon atoms are replaced by a heteroatom. If the heteroaryl group is bicyclic or tricyclic, then at least one of the two or three rings must contain a heteroatom, though both or all three may each contain one or more heteroatoms. If the heteroaryl group is bicyclic or tricyclic, then only one of the rings must be aromatic. The N group may be N, NH, or N-substituent, depending on the chosen ring and if substituents are recited. The nitrogen and sulfur heteroatoms may optionally be oxidized (e.g., S, S(O), S(O)₂, and N—O). The heteroaryl ring may be attached to its pendant group at any heteroatom or carbon atom that results in a stable structure. The heteroaryl rings described herein may be substituted on carbon or on a nitrogen atom if the resulting compound is stable."

The term "heteroatom" means for example oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring.

The term "bicyclic" represents either an unsaturated or saturated stable 7- to 12-membered bridged or fused bicyclic carbon ring. The bicyclic ring may be attached at any carbon atom which affords a stable structure. The term includes, but is not limited to, naphthyl, dicyclohexyl, dicyclohexenyl, and the like.

Substituted ring groups such as substituted cycloalkyl, aryl, heterocyclyl and heteroaryl groups also include rings and fused ring systems in which a bond to a hydrogen atom is replaced with a bond to a carbon atom. Therefore, substituted cycloalkyl, aryl, heterocyclyl and heteroaryl groups can also be substituted with alkyl, alkenyl, and alkynyl groups as defined herein.

By a "ring system" as the term is used herein is meant a moiety comprising one, two, three or more rings, which can be substituted with non-ring groups or with other ring systems, or both, which can be fully saturated, partially unsaturated, fully unsaturated, or aromatic, and when the ring system includes more than a single ring, the rings can be fused, bridging, or spirocyclic. By "spirocyclic" is meant the class of structures wherein two rings are fused at a single tetrahedral carbon atom, as is well known in the art.

Recursive substituents are an intended aspect of the disclosed subject matter. One of ordinary skill in the art of medicinal and organic chemistry understands the versatility of such substituents. To the degree that recursive substituents are present in a claim of the disclosed subject matter, the total number should be determined as set forth above.

The compounds of the present invention contain one or more asymmetric centers in the molecule. In accordance with the present invention a structure that does not designate the stereochemistry is to be understood as embracing all the various optical isomers, as well as racemic mixtures thereof.

The compounds of the present invention may exist in tautomeric forms and the invention includes both mixtures and separate individual tautomers. For example the following structure:

is understood to represent a mixture of the structures:

The term "pharmaceutically-acceptable salt" refers to salts which retain the biological effectiveness and properties of the compounds of the present invention and which are not biologically or otherwise undesirable. In many cases, the compounds of the present invention are capable of forming acid and/or base salts by virtue of the presence of amino and/or carboxyl groups or groups similar thereto.

Compounds of the present invention that have one or more asymmetric carbon atoms may exist as the optically pure enantiomers, or optically pure diastereomers, as well as mixtures of enantiomers, mixtures of diastereomers, and racemic mixtures of such stereoisomers. The present invention includes within its scope all such isomers and mixtures thereof.

The present invention includes pharmaceutically acceptable salts, prodrugs, tautomers, stereoisomers, hydrates, and solvates of the compounds disclosed herein including, e.g., a salt of a tautomer of a compound described herein and a tautomer of a salt of a compound described herein.

Compounds

The present invention provides a compound according to Formula II, or a pharmaceutically acceptable salt, prodrug, tautomer, stereoisomer, hydrate, or solvate thereof:

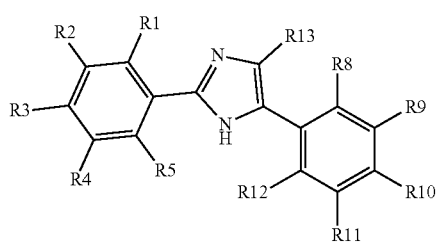

Formula II wherein
R1, R2, R4, R5, R8 and R12 in each occurrence is independently H, $CH_3$, F, Cl, Br, I, $OCH_3$, $CF_3$, $OCF_3$, $NH_2$, COOH, CHO, OH, SH, $NO_2$, $COCH_3$, $CONH_2$, or $NHCOCH_3$;
R3 is H, $CH_3$, F, Cl, Br, I, $OCH_3$, $CF_3$, $OCF_3$, $NH_2$, COOH, CHO, OH, SH, $NO_2$, $COCH_3$, $CONH_2$, or $NHCOCH_3$;
R9, R10 and R11 each is independently H, $CH_3$, F, Cl, Br, I, $OCH_3$, $CF_3$, $OCF_3$, $NH_2$, COOH, CHO, OH, SH, $NO_2$, $COCH_3$, $CONH_2$, $NHCOCH_3$, or

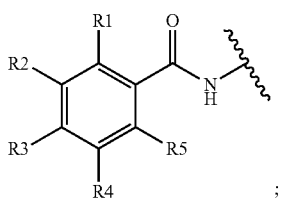
;

R13 is H, optionally substituted $C_1$-$C_6$ alkyl, optionally substituted $C_1$-$C_6$ haloalkyl, optionally substituted $C_6$-$C_{10}$ aryl, optionally substituted 5, 6, 7, 8 and 9-membered heteroaryl, or halogen; and
wherein when R13 is H then R9, R10 or R11 is

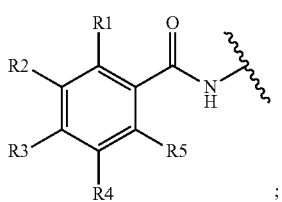
;

and
wherein when R13 is $CH_3$ then R3 is H.

In some embodiments, R13 is optionally substituted $C_1$-$C_6$ alkyl. In other embodiments R13 is $C_1$-$C_6$ alkyl. R13 may be $CH_3$.

In some embodiments, R1, R2, R3, R4 and R5 in each occurrence is independently H, Cl, $OCH_3$, OH, $CF_3$, or $NHCOCH_3$. In further embodiments, R3 is H, Cl, $OCH_3$, or $NHCOCH_3$. In further embodiments, R1, R2, R4 and R5 each is independently H, $OCH_3$, $CF_3$, or OH. In certain embodiments, each of R1, R2, R4 and R5 is H; or each of R1, R3, R4 and R5 is H; or each of R1, R2, R3, R4 and R5 is H.

In some embodiments, R8, R9, R10, R11 and R12 each is independently H, $CH_3$, F, Cl, Br, I, $OCH_3$, $CF_3$, $OCF_3$, $NH_2$, COOH, CHO, OH, SH, $NO_2$, $COCH_3$, $CONH_2$, $NHCOCH_3$. In further embodiments, R8, R9, R10, R11 and R12 each is independently H or $CF_3$.

The compound may have the structure:

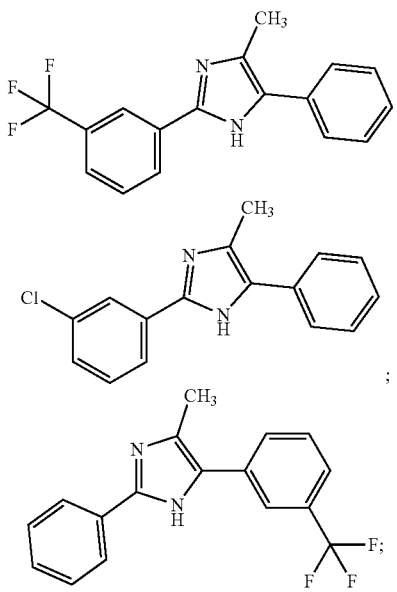

or a pharmaceutically acceptable salt, prodrug, tautomer, stereoisomer, hydrate, or solvate thereof.

In some embodiments, R13 is H and R9, R10 or R11 is

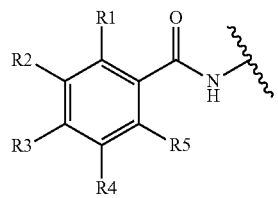

In certain embodiments R9 is

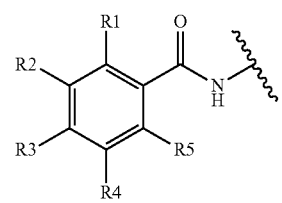

and R10 and R11 are H. In certain other embodiments R10 is

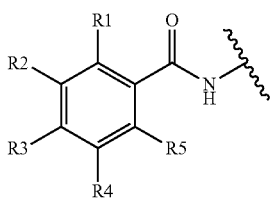

and R9 and R11 are H.

In some embodiments, at least one of R9, R10 and R11 is

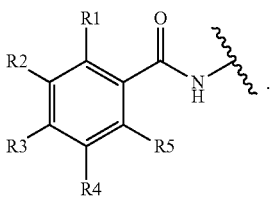

In another embodiment, only one of R9, R10 and R11 is

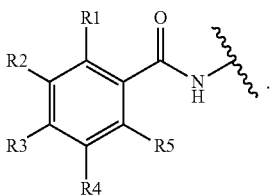

The structure

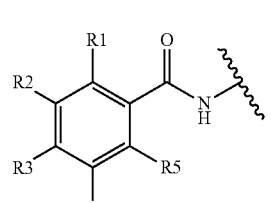

has R1, R2, R3, R4, R5 which may be, independently, H, CH₃, F, Cl, Br, I, OCH₃, CF₃, OCF₃, NH₂, COOH, CHO, OH, SH, NO₂, COCH₃, CONH₂, or NHCOCH₃ for each occurrence of R1, R2, R3, R4, R5 independently from any other occurrence of R1, R2, R3, R4, R5.

The structure

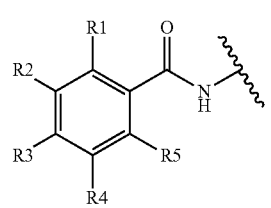

may have R3 is H, Cl or OCH₃ and may have R1, R2, R4 and R5 are H.

In some embodiments, R13 is H and R9, R10 or R11 is

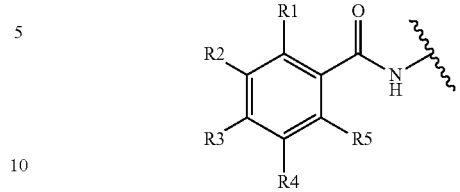

and at least one occurrence of R3 is OCH₃ or Cl. In yet further embodiments, at least one occurrence of R3 is OCH₃, only one occurrence of R3 is OCH₃ or each occurrence of R3 is OCH₃. Each occurrence of R3 may be the same. In another embodiment, each occurrence of R3 differs. In various embodiments each occurrence of R1, R2, R4 and R5 are H The compound may have the structure:

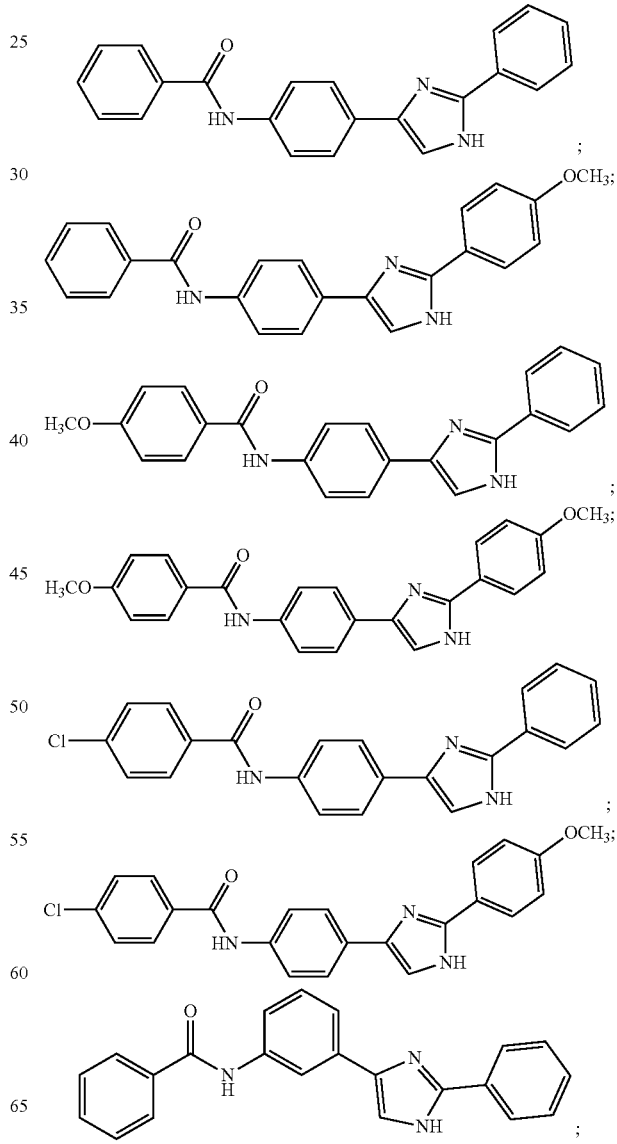

-continued

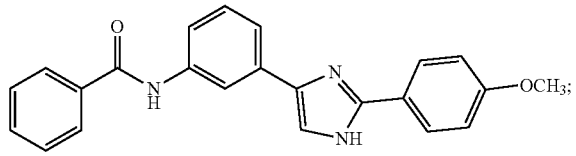

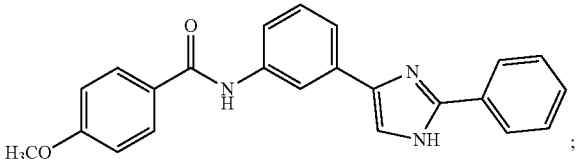

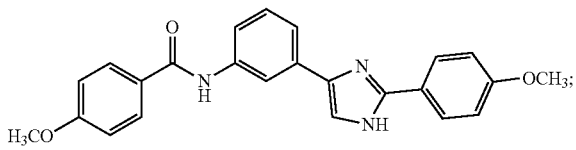

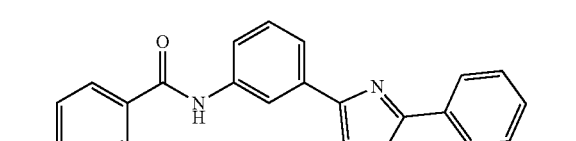

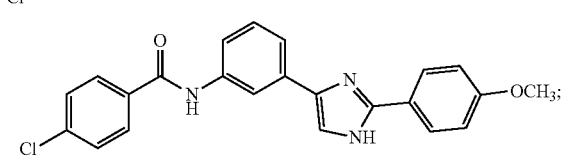

or a pharmaceutically acceptable salt, prodrug, tautomer, stereoisomer, hydrate, or solvate thereof.

The present invention also provides a compound having the structure:

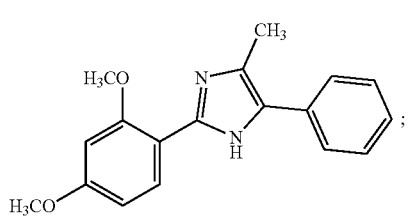

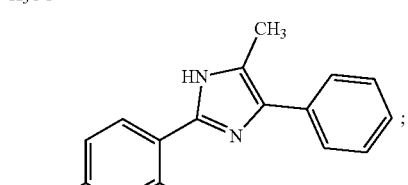

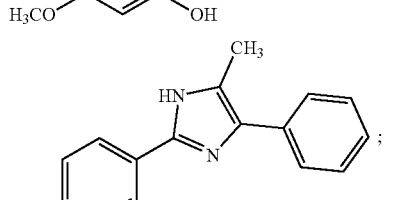

-continued

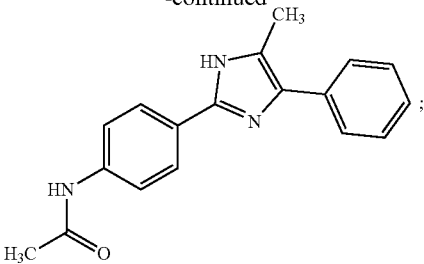

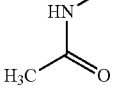

or a pharmaceutically acceptable salt, prodrug, tautomer, stereoisomer, hydrate, or solvate thereof.

The present invention also provides compounds of Formula I or a tautomer thereof, or a pharmaceutically acceptable salt or solvate of said compound or said tautomer:

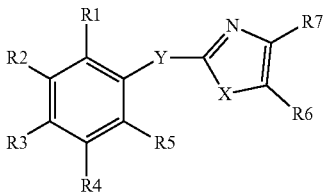

Formula I wherein each of R1, R2, R3, R4 and R5 is, independently, H, optionally substituted $C_1$-$C_6$ alkyl, optionally substituted $C_1$-$C_6$ haloalkyl, optionally substituted $C_6$-$C_{10}$ aryl, optionally substituted 5, 6, 7, 8 and 9-membered heteroaryl, or halogen;

X is C, N, O, or S;

Y is $(CH_2)_n$, where n=0,1,2; $CH_2CO$; NH, O, or S

R1 and/or R5 is H, $CH_3$, F, Cl, Br, I, $OCH_3$, $CF_3$, $OCF_3$, $NH_2$, COOH, CHO, OH, SH, $NO_2$, $COCH_3$, $CONH_2$, or $NHCOCH_3$;

R2 and/or R4 is H, $CH_3$, F, Cl, Br, I, $OCH_3$, $CF_3$, $OCF_3$, $NH_2$, COOH, CHO, OH, SH, $NO_2$, $COCH_3$, $CONH_2$, or $NHCOCH_3$;

R3 is H, $CH_3$, F, Cl, Br, I, $OCH_3$, $CF_3$, $OCF_3$, $NH_2$, COOH, CHO, OH, SH, $NO_2$, $COCH_3$, $CONH_2$, or $NHCOCH_3$;

R6 and/or R7 is H, optionally substituted $C_1$-$C_6$ alkyl containing the requisite number of carbon atoms can be branched or unbranched, optionally substituted $C_1$-$C_6$ haloalkyl containing the requisite number of carbon atoms can be branched or unbranched, optionally substituted $C_6$-$C_{10}$ aryl, or optionally substituted 5, 6, 7, 8 and 9-membered heteroaryl;

or R6 and R7 together with the carbon atom to which they are respectively attached may form a benzo-fused carbocycle or heterocycle.

The present invention provides compounds useful as sodium (Na) channel blockers for the treatment of multiple diseases and disorders mediated by modulation of voltage-gated sodium channels including, but not limited to, CNS disorders such as epilepsy, chronic pain and neuropathic pain. Compounds of the present invention include aryl substituted oxazoles, thiazoles, imidazoles, benzoxazoles, benzothiazoles and benzimidazoles. In some embodiments, the compounds are aryl-substituted imidazoles and benzimidazoles. In further embodiments, the compounds are 2,4(5)-diaryl imidazoles and 2-arylbenzimidazoles.

The compounds of formula (I) when X=NH can exist in tautomeric forms. Specifically, the 2 (or 4 or 5)-monosubstituted, the 2,4-disubstituted and the 2,4,5-trisubstituted imidazoles can exist as the (1H)-tautomer or the (3H)-tautomer. Such compounds may exist in substantially pure (1H)-tautomeric form, substantially pure (3H)-tautomeric form or as any mixture of tautomeric forms. All such tautomers and mixtures of tautomers are included within the scope of the present inventon. References herein to specific compounds should be understood to refer to the compound and/or its tautomer.

Herein, references to compounds of the invention include compounds of formula I (and other formulas herein) or pharmaceutically adequate salts or solvates or pharmaceutically acceptable solvates of pharmaceutically acceptable salt.

The compounds of formula I or pharmaceutically acceptable salts thereof may exist both in unsolvated or solvated forms.

The compounds of the invention may exist in a continuum of solid states ranging from amorphous to fully crystalline.

The compounds of the invention may exist in a mesomorphic state as well as true liquid state.

As to any of the groups described herein, which contain one or more substituents, it is understood, of course, that such groups do not contain any substitution or substitution patterns which are sterically impractical and/or synthetically non-feasible. In addition, the compounds of this disclosed subject matter include all stereochemical isomers arising from the substitution of these compounds.

Selected substituents within the compounds described herein are present to a recursive degree. In this context, "recursive substituent" means that a substituent may recite another instance of itself or of another substituent that itself recites the first substituent. Because of the recursive nature of such substituents, theoretically, a large number may be present in any given claim. One of ordinary skill in the art of medicinal chemistry and organic chemistry understands that the total number of such substituents is reasonably limited by the desired properties of the compound intended. Such properties include, by way of example and not limitation, physical properties such as molecular weight, solubility or log P, application properties such as activity against the intended target, and practical properties such as ease of synthesis.

Some of the compounds exist as tautomeric isomers. Tautomeric isomers are in equilibrium with one another. For example, amide containing compounds may exist in equilibrium with imidic acid tautomers. Regardless of which tautomer is shown, and regardless of the nature of the equilibrium among tautomers, the compounds are understood by one of ordinary skill in the art to comprise both amide and imidic acid tautomers. Thus, any amide containing compounds are understood to include their imidic acid tautomers. Likewise, any imidic acid containing compounds are understood to include their amide tautomers.

Provided also are all tautomeric forms of the compounds of any Formula described herein. Tautomeric isomers are in equilibrium with one another. Regardless of which tautomer is shown, and regardless of the nature of the equilibrium among tautomers, the compounds are understood by one of ordinary skill in the art to comprise both.

In certain embodiments, provided herein are also crystalline and amorphous forms of the compounds described herein or pharmaceutically acceptable salts, isomer, or a mixture thereof.

Accordingly, the chemical structures depicted herein encompass all possible tautomeric forms of the illustrated compounds. Compounds may exist in unsolvated forms as well as solvated forms, including hydrated forms. Certain compounds may exist in multiple crystalline, co-crystalline, or amorphous forms. Compounds of Formula (1) and other formulas of the invention include pharmaceutically acceptable salts thereof, or pharmaceutically acceptable solvates of the free acid form of any of the foregoing, as well as crystalline forms of any of the foregoing.

In various embodiments of the compound it is an acetate, carbonate, sulphate, citrate, fumarate, hydrochloride, chloride, hydrobromide, bromide, mesylate, methylsulphate, nitrate, oxalate, phosphate, hydrogenphosphate, dihydrogenphosphate, tartrate or tosylate salt. In further embodiments, the compound is a hydrochloride salt.

Pharmaceutical Compositions

The present invention provides pharmaceutical compositions comprising a pharmaceutically-acceptable carrier and an effective amount of at least one compound of the invention.

The present invention provides a pharmaceutical composition comprising a pharmaceutically acceptable carrier and a therapeutically effective amount of a compound according to Formula II or Formula III, or a pharmaceutically acceptable salt, prodrug, tautomer, stereoisomer, hydrate, or solvate thereof:

Formula II

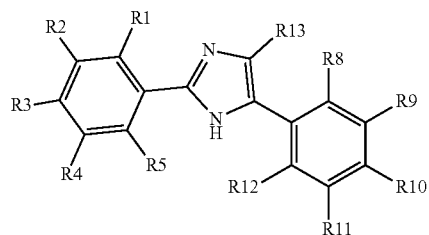

wherein

R1, R2, R3, R4, R5, R8 and R12 in each occurrence is independently H, $CH_3$, F, Cl, Br, I, $OCH_3$, $CF_3$, $OCF_3$, $NH_2$, COOH, CHO, OH, SH, $NO_2$, $COCH_3$, $CONH_2$, or $NHCOCH_3$;

R9, R10 and R11 each is independently H, $CH_3$, F, Cl, Br, I, $OCH_3$, $CF_3$, $OCF_3$, $NH_2$, COOH, CHO, OH, SH, $NO_2$, $COCH_3$, $CONH_2$, $NHCOCH_3$, or

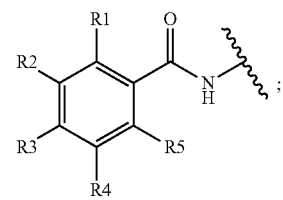

R13 is H, optionally substituted $C_1$-$C_6$ alkyl, optionally substituted $C_1$-$C_6$ haloalkyl, optionally substituted $C_6$-$C_{10}$ aryl, optionally substituted 5, 6, 7, 8 and 9-membered heteroaryl, or halogen; and when R13 is H then R9, R10 or R11 is

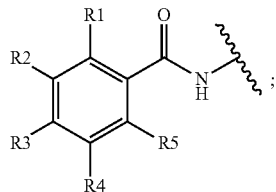

and

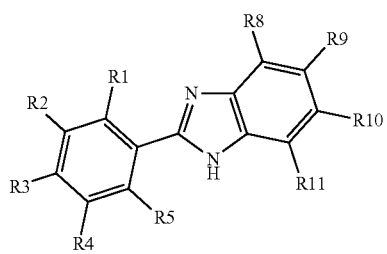

Formula III wherein

R1, R2, R4 and R5 each is independently H, OCH$_3$, CF$_3$, OCF$_3$, NH$_2$, COOH, CHO, OH, SH, COCH$_3$, CONH$_2$, or NHCOCH$_3$;

R3 is H;

R8 and R11 each is independently H, CH$_3$, F, Cl, Br, I, OCH$_3$, CF$_3$, OCF$_3$, NH$_2$, COOH, CHO, OH, SH, NO$_2$, COCH$_3$, CONH$_2$, or NHCOCH$_3$;

R9 is F, Cl, Br, I, NO$_2$, or CF$_3$; and

R10 is H.

In various embodiments of the pharmaceutical composition the compound is according to Formula II, or a pharmaceutically acceptable salt, prodrug, tautomer, stereoisomer, hydrate, or solvate thereof:

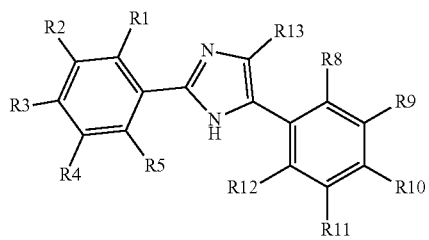

Formula II wherein

R1, R2, R3, R4, R5, R8 and R12 in each occurrence is independently H, CH$_3$, F, Cl, Br, I, OCH$_3$, CF$_3$, OCF$_3$, NH$_2$, COOH, CHO, OH, SH, NO$_2$, COCH$_3$, CONH$_2$, or NHCOCH$_3$;

R9, R10 and R11 each is independently H, CH$_3$, F, Cl, Br, I, OCH$_3$, CF$_3$, OCF$_3$, NH$_2$, COOH, CHO, OH, SH, NO$_2$, COCH$_3$, CONH$_2$, NHCOCH$_3$, or

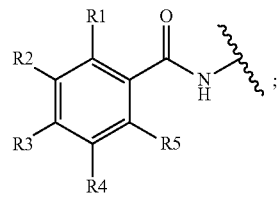

R13 is H, optionally substituted C$_1$-C$_6$ alkyl, optionally substituted C$_1$-C$_6$ haloalkyl, optionally substituted C$_6$-C$_{10}$ aryl, optionally substituted 5, 6, 7, 8 and 9-membered heteroaryl, or halogen; and wherein when R13 is H then R9, R10 or R11 is

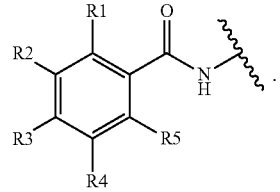

In some embodiments, R13 is optionally substituted C$_1$-C$_6$ alkyl. In other embodiments R13 is C$_1$-C$_6$ alkyl. R13 may be CH$_3$.

In various embodiments, R1, R2, R3, R4 and R5 in each occurrence is independently H, Cl, OCH$_3$, OH, CF$_3$, or NHCOCH$_3$. In further embodiments, R3 is H, Cl, OCH$_3$, or NHCOCH$_3$. In yet further embodiments, R1, R2, R4 and R5 each is independently H, OCH$_3$, CF$_3$, or OH. In certain embodiments, each of R1, R2, R4 and R5 is H; or each of R1, R3, R4 and R5 is H; or each of R1, R2, R3, R4 and R5 is H.

In various embodiments, R8, R9, R10, R11 and R12 each is independently H, CH$_3$, F, Cl, Br, I, OCH$_3$, CF$_3$, OCF$_3$, NH$_2$, COOH, CHO, OH, SH, NO$_2$, COCH$_3$, CONH$_2$, NHCOCH$_3$. In further embodiments, R8, R9, R10, R11 and R12 each is independently H or CF$_3$.

The compound may have the structure:

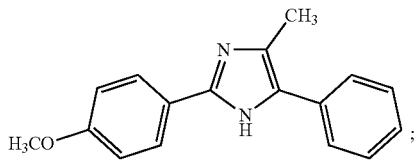

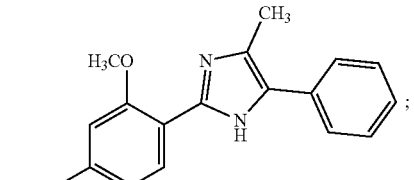

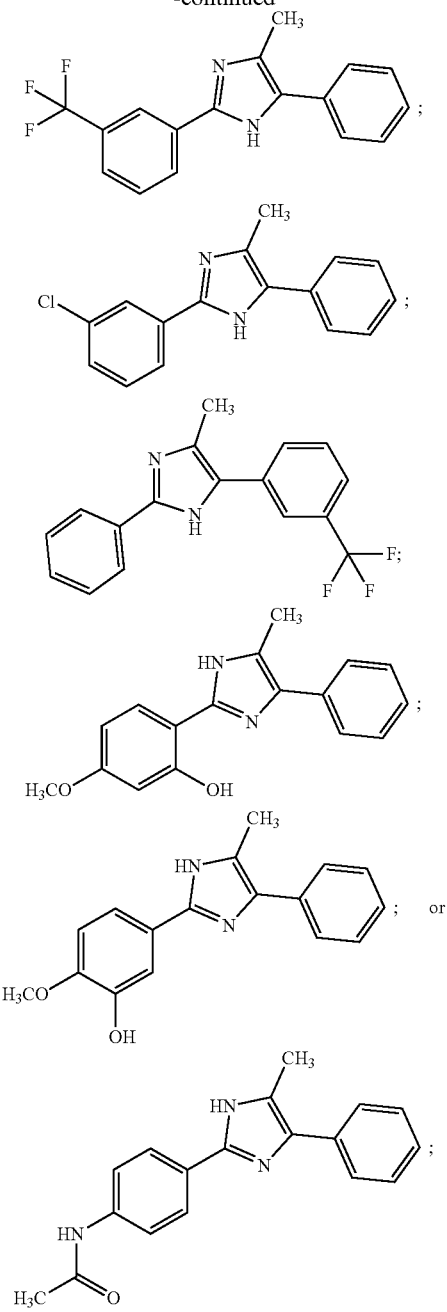

or a pharmaceutically acceptable salt, prodrug, tautomer, stereoisomer, hydrate, or solvate thereof.

In some embodiments, R13 is H and R9, R10 or R11 is

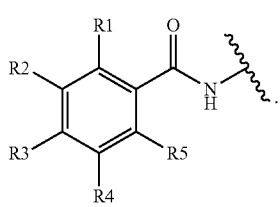

In certain embodiments R9 is

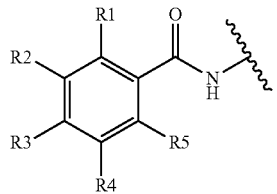

and R10 and R11 are H. In certain other embodiments R10 is

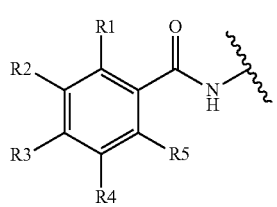

and R9 and R11 are H.

In some embodiments, at least one of R9, R10 and R11 is

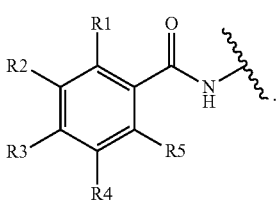

In another embodiment, only one of R9, R10 and R11 is

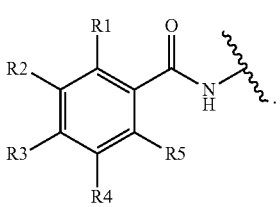

The structure

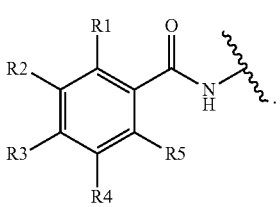

has R1, R2, R3, R4, R5 which may be, independently, H, $CH_3$, F, Cl, Br, I, $OCH_3$, $CF_3$, $OCF_3$, $NH_2$, COOH, CHO, OH, SH, $NO_2$, $COCH_3$, $CONH_2$, or $NHCOCH_3$ for each occurrence of R1, R2, R3, R4, R5 independently from any other occurrence of R1, R2, R3, R4, R5.

The structure

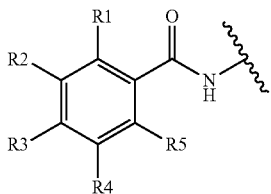

may have R3 is H, Cl or OCH₃ and may have R1, R2, R4 and R5 are H.

In some embodiments, R13 is H and R9, R10 or R11 is

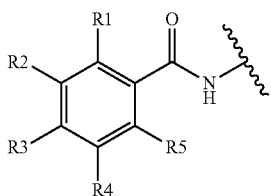

and at least one occurrence of R3 is OCH₃ or Cl. In yet further embodiments, at least one occurrence of R3 is OCH₃, only one occurrence of R3 is OCH₃ or each occurrence of R3 is OCH₃. Each occurrence of R3 may be the same. In another embodiment, each occurrence of R3 differs. In various embodiments each occurrence of R1, R2, R4 and R5 are H.

In various embodiments of the method, the compound has the structure:

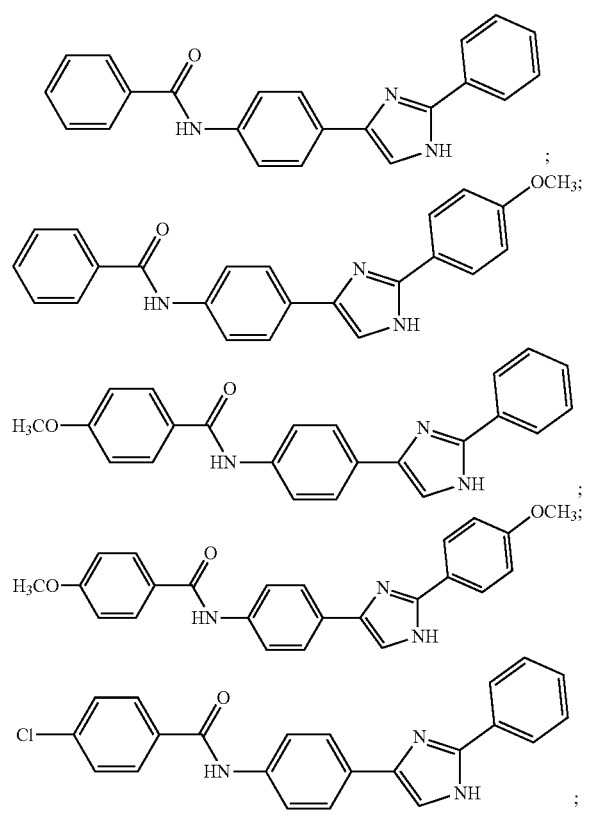

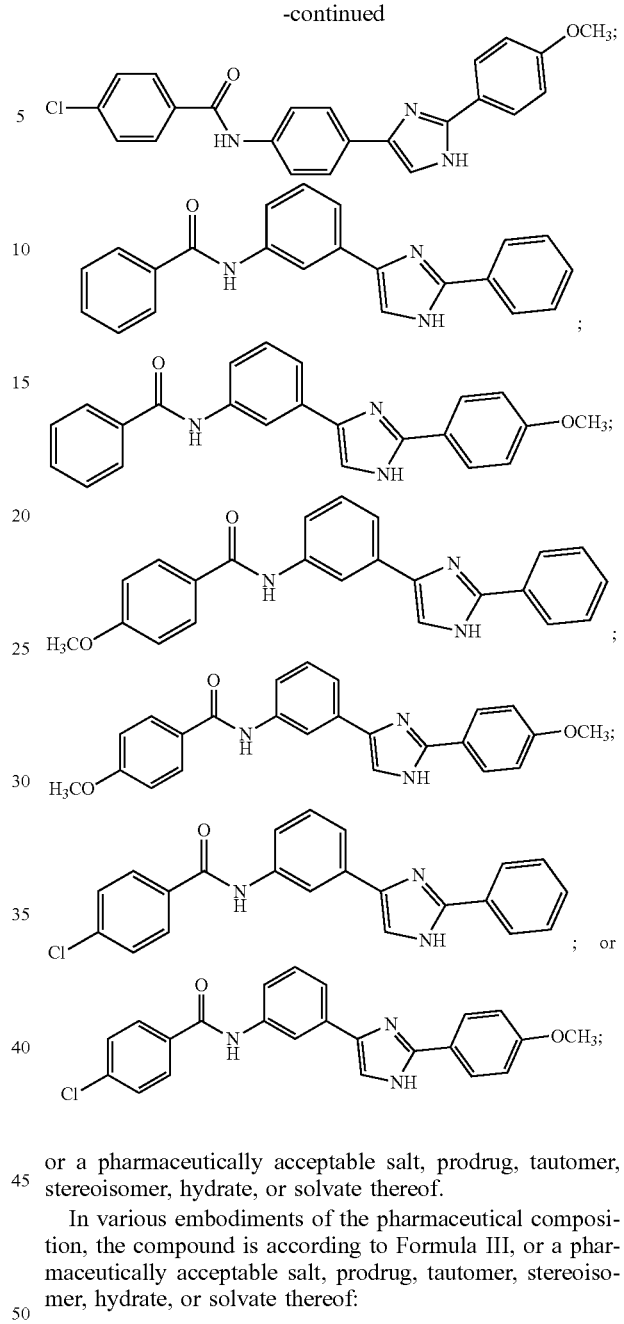

or a pharmaceutically acceptable salt, prodrug, tautomer, stereoisomer, hydrate, or solvate thereof.

In various embodiments of the pharmaceutical composition, the compound is according to Formula III, or a pharmaceutically acceptable salt, prodrug, tautomer, stereoisomer, hydrate, or solvate thereof:

Formula III

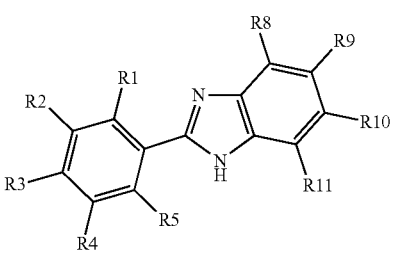

wherein

R1, R2, R4 and R5 each is independently H, OCH₃, CF₃, OCF₃, NH₂, COOH, CHO, OH, SH, COCH₃, CONH₂, or NHCOCH₃;

R3 is H;

R8 and R11 each is independently H, CH₃, F, Cl, Br, I, OCH₃, CF₃, OCF₃, NH₂, COOH, CHO, OH, SH, NO₂, COCH₃, CONH₂, or NHCOCH₃;

R9 is F, Cl, Br, I, NO₂, or CF₃; and

R10 is H.

In further embodiments, R9 is Cl, NO₂ or CF₃. In yet further embodiments R9 is Cl.

In further embodiments, R1, R2, R4 and R5 each is independently H or OCH₃. In yet further embodiments, at least three of R1, R2, R4 and R5 are H.

In various embodiments, R8 and R11 are H.

In various embodiments of the method the compound is:

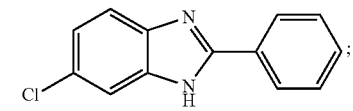

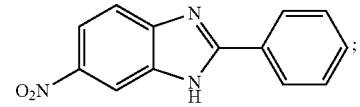

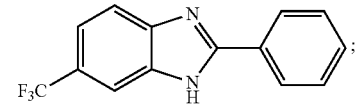

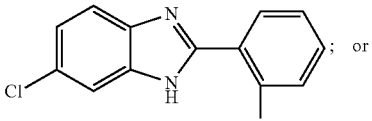

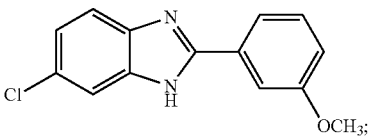

or a pharmaceutically acceptable salt, prodrug, tautomer, stereoisomer, hydrate, or solvate thereof.

The present invention provides a pharmaceutical composition comprising a pharmaceutically acceptable carrier and a therapeutically effective amount of a compound, wherein the compound is:

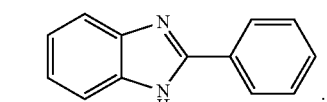

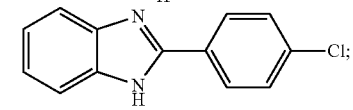

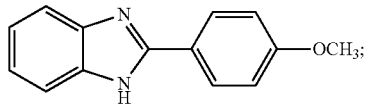

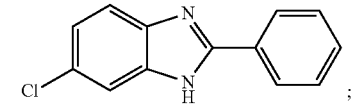

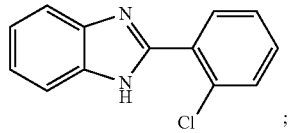

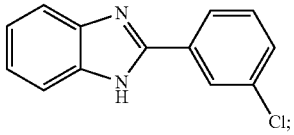

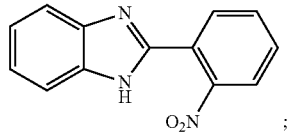

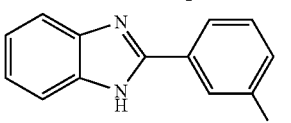

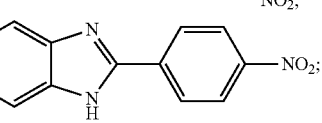

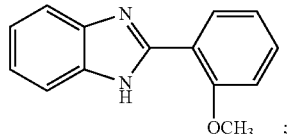

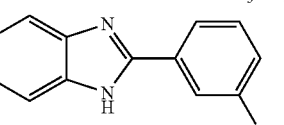

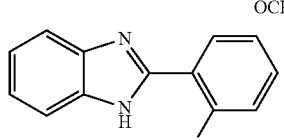

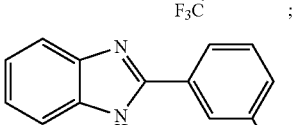

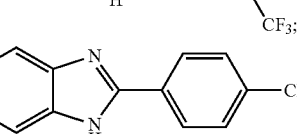

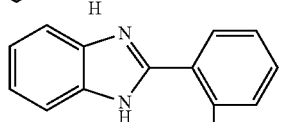

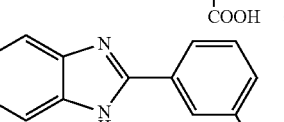

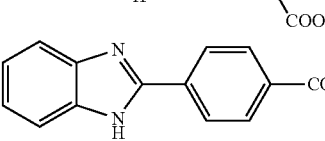

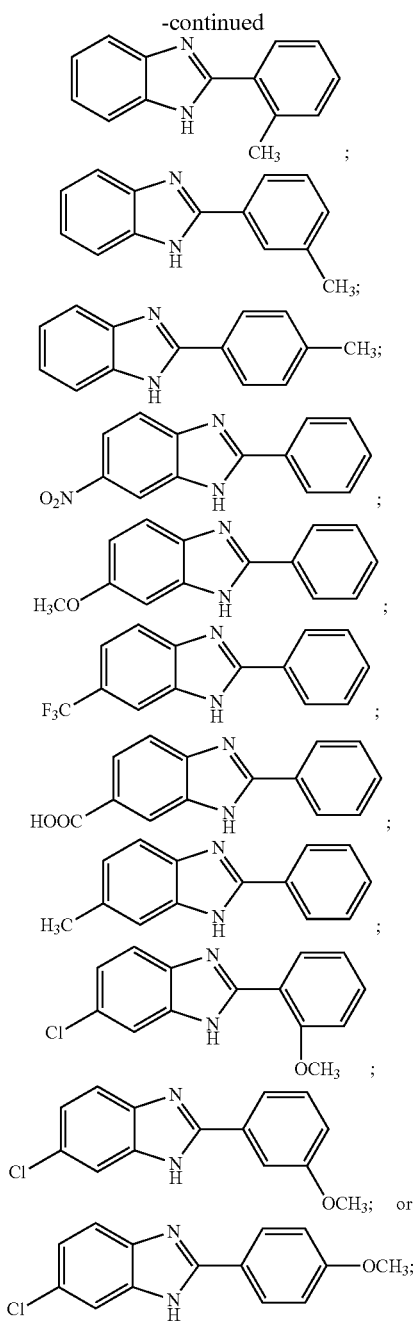

or a pharmaceutically acceptable salt, prodrug, tautomer, stereoisomer, hydrate, or solvate thereof, In various embodiments of the pharmaceutical composition, one of R1, R2, R3, R4, R5, R8, R9, R10, R11 and R12 of Formula II is other than H and the remainder are H.

In some embodiments of the pharmaceutical composition, two of R1, R2, R3, R4, R5, R8, R9, R10, R11 and R12 of Formula II are other than H and the remainder are H.

In various embodiments of the pharmaceutical composition, one of R1, R2, R3, R4, R5, R8, R9, R10, and R11 of Formula III is other than H and the remainder are H.

In some embodiments of the pharmaceutical composition, two of R1, R2, R3, R4, R5, R8, R9, R10, and R11 of Formula III are other than H and the remainder are H.

In various embodiments, the present invention provides compositions useful for blocking Na (sodium) channels.

The present invention provides a pharmaceutical composition comprising a pharmaceutically-acceptable carrier and an effective amount of at least one compound of Formula I or a tautomer thereof, or a pharmaceutically acceptable salt or solvate of said compound or said tautomer:

Formula I wherein each of R1, R2, R3, R4 and R5 is, independently, H, optionally substituted $C_1$-$C_6$ alkyl, optionally substituted $C_1$-$C_6$ haloalkyl, optionally substituted $C_6$-$C_{10}$ aryl, optionally substituted 5, 6, 7, 8 and 9-membered heteroaryl, or halogen;

X is C, N, O, or S;

Y is $(CH_2)_n$, where n=0,1,2; CH2CO; NH, O, or S

R1 and/or R5 is H, $CH_3$, F, Cl, Br, I, $OCH_3$, $CF_3$, $OCF_3$, $NH_2$, COOH, CHO, OH, SH, NO2, $COCH_3$, $CONH_2$, or $NHCOCH_3$;

R2 and/or R4 is H, $CH_3$, F, Cl, Br, I, $OCH_3$, $CF_3$, $OCF_3$, $NH_2$, COOH, CHO, OH, SH, NO2, $COCH_3$, $CONH_2$, or $NHCOCH_3$;

R3 is H, $CH_3$, F, Cl, Br, I, $OCH_3$, $CF_3$, $OCF_3$, $NH_2$, COOH, CHO, OH, SH, NO2, $COCH_3$, $CONH_2$, or $NHCOCH_3$;

R6 and/or R7 is H, optionally substituted $C_1$-$C_6$ alkyl containing the requisite number of carbon atoms can be branched or unbranched, optionally substituted $C_1$-$C_6$ haloalkyl containing the requisite number of carbon atoms can be branched or unbranched, optionally substituted $C_6$-$C_{10}$ aryl, or optionally substituted 5, 6, 7, 8 and 9-membered heteroaryl;

or R6 and R7 together with the carbon atom to which they are respectively attached may form a benzo-fused carbocycle or heterocycle.

The compound may be a compound listed in Table 1.

As described herein, the compositions of the present invention comprise, as an active agent, compounds having the structure of any of the formulas disclosed herein in a pharmaceutically acceptable form. If desired, the compositions may further comprise one or more additional active agents. Where it is appropriate, any of the active agents may be administered in the form of the compound per se, and/or in the form of a salt, polymorph, ester, amide, prodrug, derivative, or the like, provided the salt, polymorph, ester, amide, prodrug or derivative is suitable pharmacologically. Where it is appropriate, salts, esters, amides, prodrugs and other derivatives of the active agents may be prepared using standard procedures known to those skilled in the art of synthetic organic chemistry and described, for example, by J. March, Advanced Organic Chemistry: Reactions, Mechanisms and Structure, 4th Ed. (New York: Wiley-Interscience, 1992). For any active agents that may exist in enantiomeric forms, the active agent may be incorporated into the present compositions either as the racemate or in enantiomerically enriched form.

The values provided herein for radicals, substituents, and ranges, are for illustration only; they do not exclude other defined values or other values within defined ranges for the radicals and substituents. The disclosed compounds include compounds of the specific Formulas recited herein having any combination of the values and exemplary values.

In one embodiment, the compounds of the invention can first be encapsulated into microcapsules, microspheres, microparticles, microfibers, reinforcing fibers and the like to facilitate mixing and achieving controlled, extended, delayed and/or sustained release and combined other agents or drugs. Encapsulating the biologically active agent can also protect the agent against degradation during formation of the composite of the invention.

In some embodiments of the pharmaceutical compositions, the compound is an acetate, carbonate, sulphate, citrate, fumarate, hydrochloride, chloride, hydrobromide, bromide, mesylate, methylsulphate, nitrate, oxalate, phosphate, hydrogenphosphate, dihydrogenphosphate, tartrate or tosylate salt. In further embodiments, the compound is a hydrochloride salt.

Methods of Use

The present invention provides a method for treating a subject suffering from a disease associated with sodium channel activity, the method comprising administering to the subject a therapeutically effective amount of a compound according to Formula II or Formula III, or a pharmaceutically acceptable salt, prodrug, tautomer, stereoisomer, hydrate, or solvate thereof:

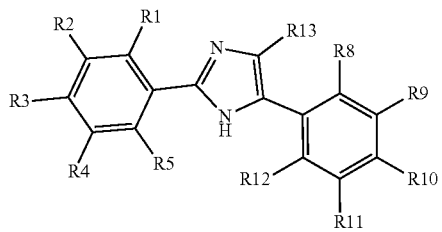

Formula II wherein

R1, R2, R3, R4, R5, R8 and R12 in each occurrence is independently H, CH$_3$, F, Cl, Br, I, OCH$_3$, CF$_3$, OCF$_3$, NH$_2$, COOH, CHO, OH, SH, NO$_2$, COCH$_3$, CONH$_2$, or NHCOCH$_3$;

R9, R10 and R11 each is independently H, CH$_3$, F, Cl, Br, I, OCH$_3$, CF$_3$, OCF$_3$, NH$_2$, COOH, CHO, OH, SH, NO$_2$, COCH$_3$, CONH$_2$, NHCOCH$_3$, or

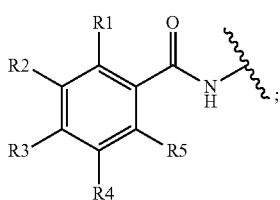

R13 is H, optionally substituted C$_1$-C$_6$ alkyl, optionally substituted C$_1$-C$_6$ haloalkyl, optionally substituted C$_6$-C$_{10}$ aryl, optionally substituted 5, 6, 7, 8 and 9-membered heteroaryl, or halogen; and when R13 is H then R9, R10 or R11 is

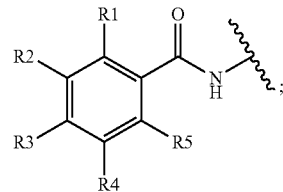

and

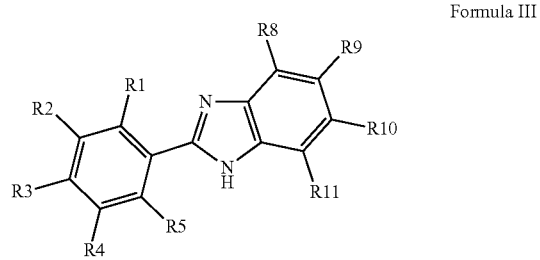

Formula III wherein

R1, R2, R4 and R5 each is independently H, OCH$_3$, CF$_3$, OCF$_3$, NH$_2$, COOH, CHO, OH, SH, COCH$_3$, CONH$_2$, or NHCOCH$_3$;

R3 is H;

R8 and R11 each is independently H, CH3, F, Cl, Br, I, OCH$_3$, CF$_3$, OCF$_3$, NH$_2$, COOH, CHO, OH, SH, NO2, COCH$_3$, CONH$_2$, or NHCOCH$_3$;

R9 is F, Cl, Br, I, NO2, or CF3; and

R10 is H.

In some embodiments of the method, the compound is according to Formula II, or a pharmaceutically acceptable salt, prodrug, tautomer, stereoisomer, hydrate, or solvate thereof:

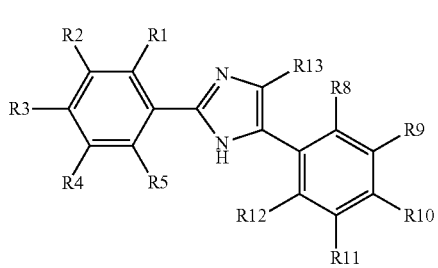

Formula II wherein

R1, R2, R3, R4, R5, R8 and R12 in each occurrence is independently H, CH$_3$, F, Cl, Br, I, OCH$_3$, CF$_3$, OCF$_3$, NH$_2$, COOH, CHO, OH, SH, NO$_2$, COCH$_3$, CONH$_2$, or NHCOCH$_3$;

R9, R10 and R11 each is independently H, CH$_3$, F, Cl, Br, I, OCH$_3$, CF$_3$, OCF$_3$, NH$_2$, COOH, CHO, OH, SH, NO$_2$, COCH$_3$, CONH$_2$, NHCOCH$_3$, or

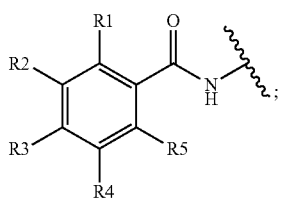

R13 is H, optionally substituted $C_1$-$C_6$ alkyl, optionally substituted $C_1$-$C_6$ haloalkyl, optionally substituted $C_6$-$C_{10}$ aryl, optionally substituted 5, 6, 7, 8 and 9-membered heteroaryl, or halogen; and wherein when R13 is H then R9, R10 or R11 is

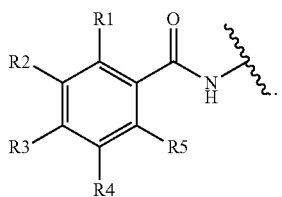

In some embodiments, R13 is optionally substituted $C_1$-$C_6$ alkyl. In other embodiments R13 is $C_1$-$C_6$ alkyl. R13 may be $CH_3$.

In various embodiments, R1, R2, R3, R4 and R5 in each occurrence is independently H, Cl, $OCH_3$, OH, $CF_3$, or $NHCOCH_3$. In further embodiments, R3 is H, Cl, $OCH_3$, or $NHCOCH_3$. In further embodiments, R1, R2, R4 and R5 each is independently H, $OCH_3$, $CF_3$, or OH. In certain embodiments, each of R1, R2, R4 and R5 is H; or each of R1, R3, R4 and R5 is H; or each of R1, R2, R3, R4 and R5 is H.

In various embodiments, R8, R9, R10, R11 and R12 each is independently H, $CH_3$, F, Cl, Br, I, $OCH_3$, $CF_3$, $OCF_3$, $NH_2$, COOH, CHO, OH, SH, $NO_2$, $COCH_3$, $CONH_2$, $NHCOCH_3$. In further embodiments, R8, R9, R10, R11 and R12 each is independently H or $CF_3$.

The compound may have the structure:

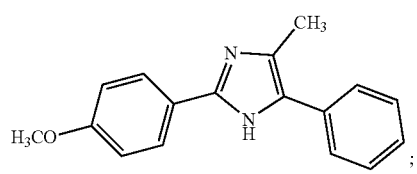

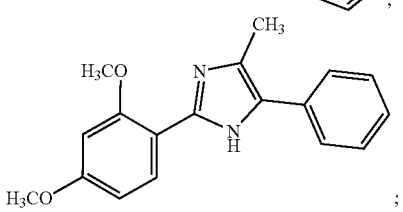

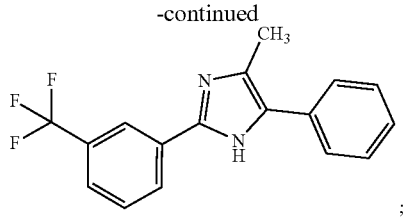

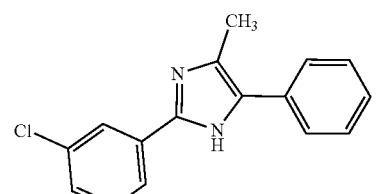

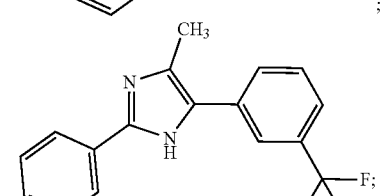

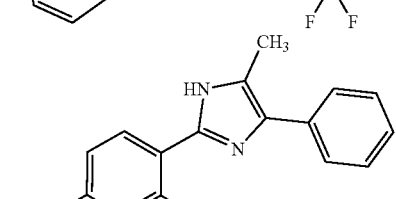

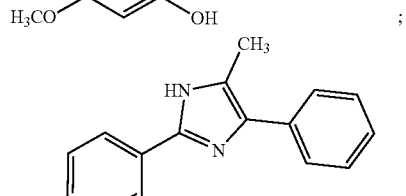

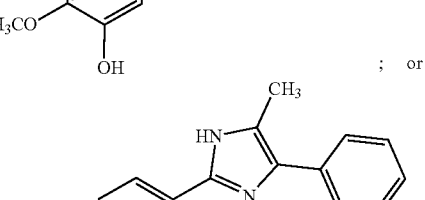

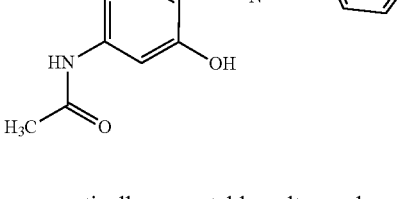

or a pharmaceutically acceptable salt, prodrug, tautomer, stereoisomer, hydrate, or solvate thereof.

In some embodiments, R13 is H and R9, R10 or R11 is

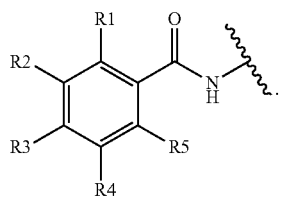

In certain embodiments R9 is

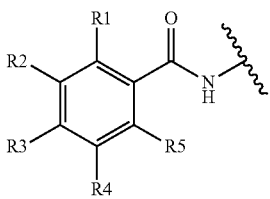

and R10 and R11 are H. In certain other embodiments R10 is

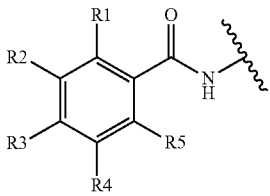

and R9 and R11 are H.

In some embodiments, at least one of R9, R10 and R11 is

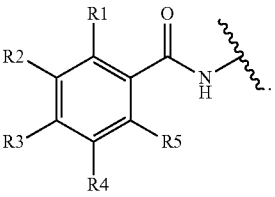

In another embodiment, only one of R9, R10 and R11 is

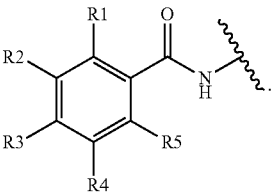

The structure

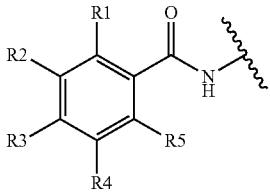

has R1, R2, R3, R4, R5 which may be, independently, H, CH₃, F, Cl, Br, I, OCH₃, CF₃, OCF₃, NH₂, COOH, CHO, OH, SH, NO₂, COCH₃, CONH₂, or NHCOCH₃ for each occurrence of R1, R2, R3, R4, R5 independently from any other occurrence of R1, R2, R3, R4, R5.

The structure

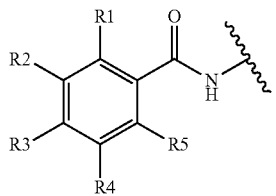

may have R3 is H, Cl or OCH₃ and may have R1, R2, R4 and R5 are H.

In some embodiments, R13 is H and R9, R10 or R11 is

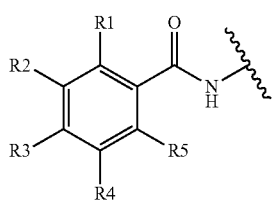

and at least one occurrence of R3 is OCH₃ or Cl. In yet further embodiments, at least one occurrence of R3 is OCH₃, only one occurrence of R3 is OCH₃ or each occurrence of R3 is OCH₃. Each occurrence of R3 may be the same. In another embodiment, each occurrence of R3 differs. In various embodiments each occurrence of R1, R2, R4 and R5 are H.

In various embodiments of the method, the compound has the structure:

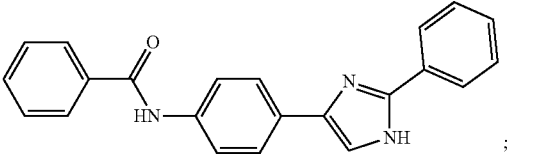

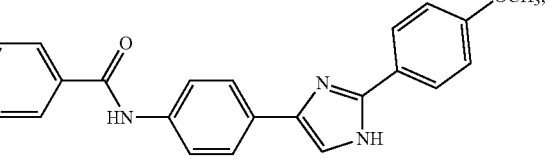

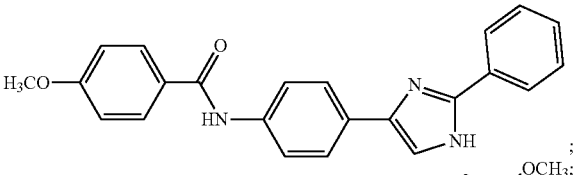

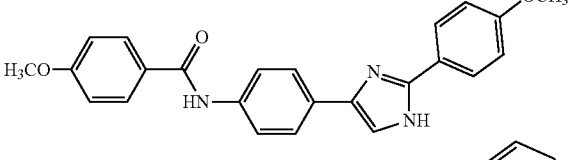

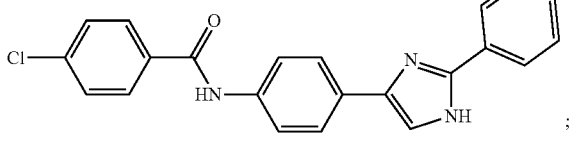

-continued

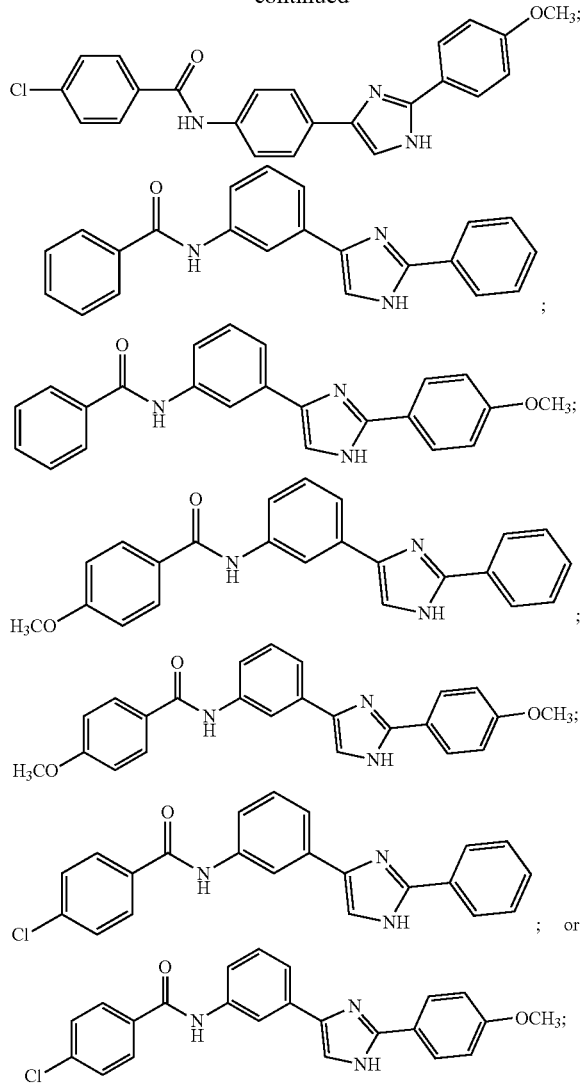

or a pharmaceutically acceptable salt, prodrug, tautomer, stereoisomer, hydrate, or solvate thereof.

In some embodiments of the method, the compound is according to Formula III, or a pharmaceutically acceptable salt, prodrug, tautomer, stereoisomer, hydrate, or solvate thereof:

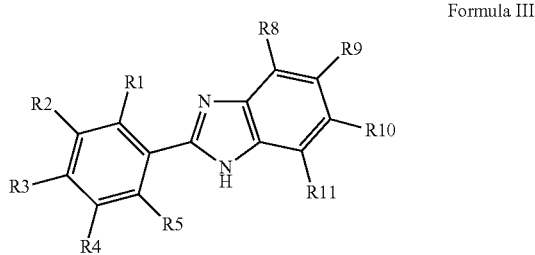

Formula III wherein

R1, R2, R4 and R5 each is independently H, OCH₃, CF₃, OCF₃, NH₂, COOH, CHO, OH, SH, COCH₃, CONH₂, or NHCOCH₃;

R3 is H;

R8 and R11 each is independently H, CH₃, F, Cl, Br, I, OCH₃, CF₃, OCF₃, NH2, COOH, CHO, OH, SH, NO₂, COCH₃, CONH2, or NHCOCH₃;

R9 is F, Cl, Br, I, NO₂, or CF₃; and

R10 is H.

In further embodiments, R9 is Cl, NO₂ or CF₃. In yet further embodiments R9 is Cl.

In further embodiments, R1, R2, R4 and R5 each is independently H or OCH₃. In yet further embodiments, at least three of R1, R2, R4 and R5 are H.

In some embodiments, R8 and R11 are H.

In some embodiments of the method the compound is:

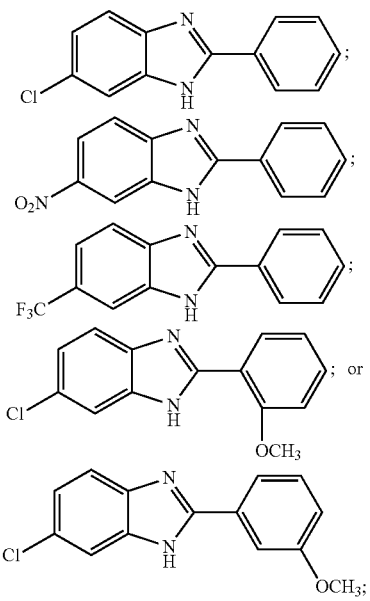

or a pharmaceutically acceptable salt, prodrug, tautomer, stereoisomer, hydrate, or solvate thereof.

The present invention also provides a method for treating a subject suffering from a disease associated with sodium channel activity, the method comprising administering to the subject a therapeutically effective amount of a compound, wherein the compound is:

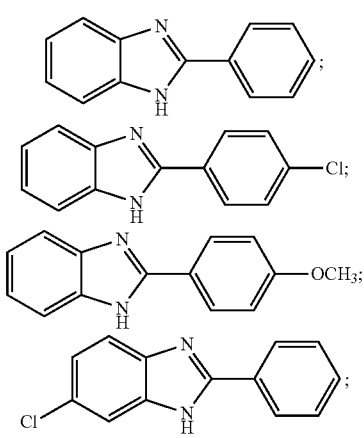

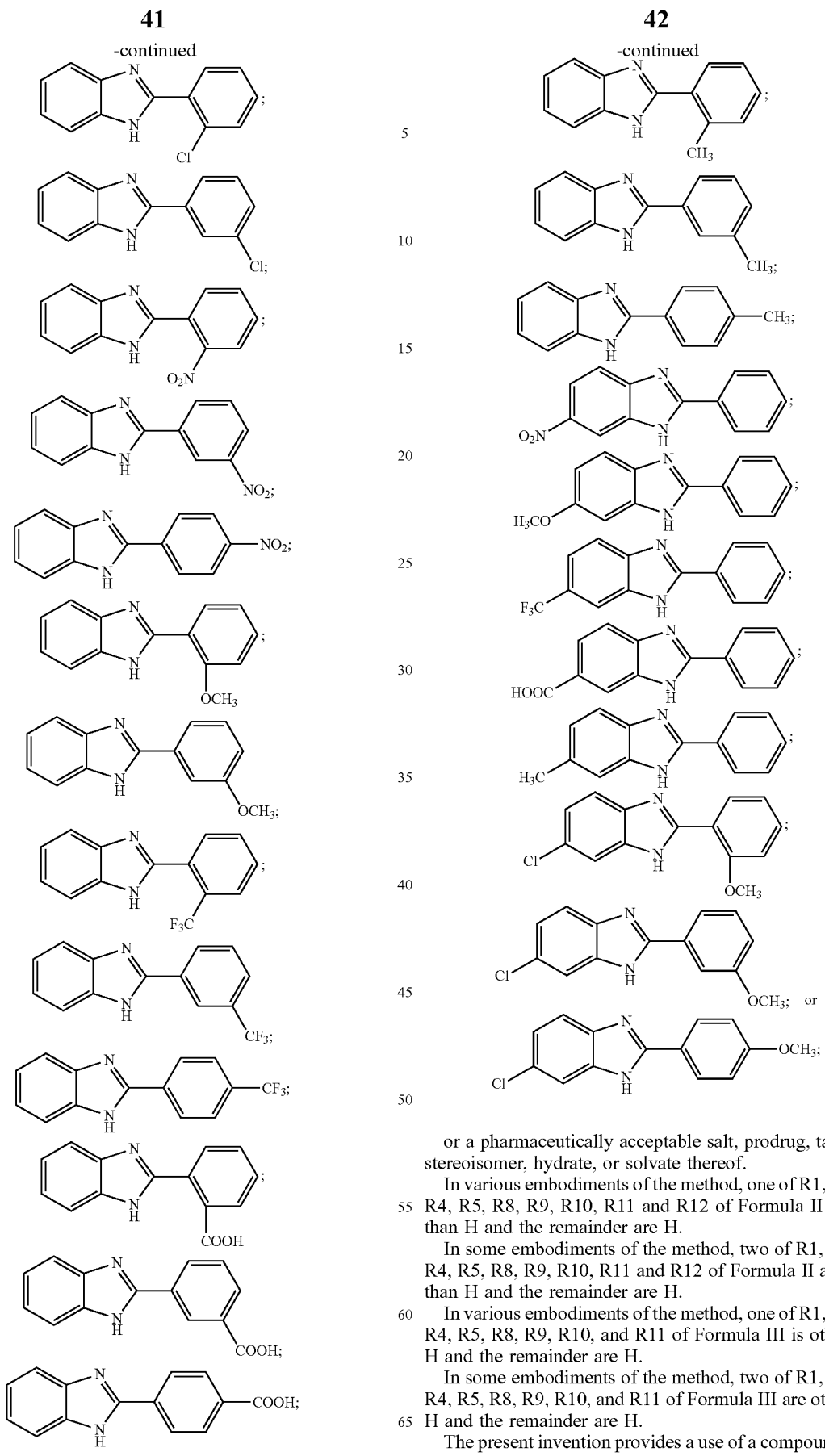

or a pharmaceutically acceptable salt, prodrug, tautomer, stereoisomer, hydrate, or solvate thereof.

In various embodiments of the method, one of R1, R2, R3, R4, R5, R8, R9, R10, R11 and R12 of Formula II is other than H and the remainder are H.

In some embodiments of the method, two of R1, R2, R3, R4, R5, R8, R9, R10, R11 and R12 of Formula II are other than H and the remainder are H.

In various embodiments of the method, one of R1, R2, R3, R4, R5, R8, R9, R10, and R11 of Formula III is other than H and the remainder are H.

In some embodiments of the method, two of R1, R2, R3, R4, R5, R8, R9, R10, and R11 of Formula III are other than H and the remainder are H.

The present invention provides a use of a compound in the manufacture of a medicament for treating a subject suffering from a disease associated with sodium channel activity, wherein the compound is according to Formula II or Formula III, or a pharmaceutically acceptable salt, prodrug, tautomer, stereoisomer, hydrate, or solvate thereof:

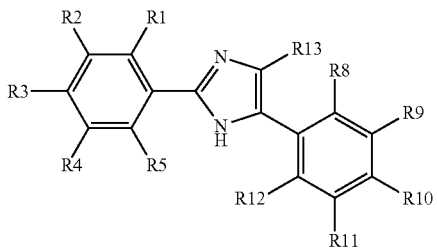

Formula II wherein

R1, R2, R3, R4, R5, R8 and R12 in each occurrence is independently H, CH$_3$, F, Cl, Br, I, OCH$_3$, CF$_3$, OCF$_3$, NH$_2$, COOH, CHO, OH, SH, NO$_2$, COCH$_3$, CONH$_2$, or NHCOCH$_3$;

R9, R10 and R11 each is independently H, CH$_3$, F, Cl, Br, I, OCH$_3$, CF$_3$, OCF$_3$, NH$_2$, COOH, CHO, OH, SH, NO$_2$, COCH$_3$, CONH$_2$, NHCOCH$_3$, or

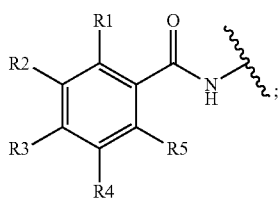

R13 is H, optionally substituted C$_1$-C$_6$ alkyl, optionally substituted C$_1$-C$_6$ haloalkyl, optionally substituted C$_6$-C$_{10}$ aryl, optionally substituted 5, 6, 7, 8 and 9-membered heteroaryl, or halogen; and when R13 is H then R9, R10 or R11 is

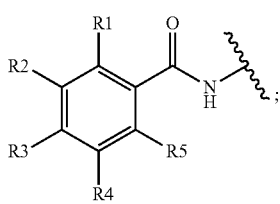

and

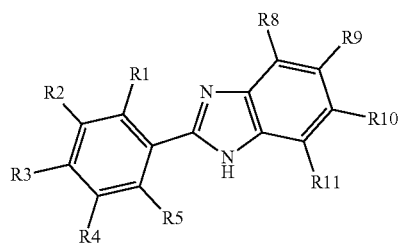

Formula III wherein

R1, R2, R4 and R5 each is independently H, OCH$_3$, CF$_3$, OCF$_3$, NH$_2$, COOH, CHO, OH, SH, COCH$_3$, CONH$_2$, or NHCOCH$_3$;

R3 is H;

R8 and R11 each is independently H, CH$_3$, F, Cl, Br, I, OCH$_3$, CF$_3$, OCF$_3$, NH$_2$, COOH, CHO, OH, SH, NO$_2$, COCH$_3$, CONH$_2$, or NHCOCH$_3$;

R9 is F, Cl, Br, I, NO$_2$, or CF$_3$; and

R10 is H.

The present invention provides a compound according to Formula II or Formula III, or a pharmaceutically acceptable salt, prodrug, tautomer, stereoisomer, hydrate, or solvate thereof, for use in treating a subject suffering from a disease associated with sodium channel activity, wherein the compound:

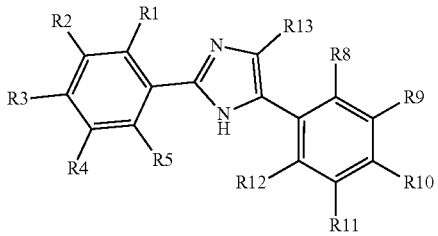

Formula II wherein

R1, R2, R3, R4, R5, R8 and R12 in each occurrence is independently H, CH$_3$, F, Cl, Br, I, OCH$_3$, CF$_3$, OCF$_3$, NH$_2$, COOH, CHO, OH, SH, NO$_2$, COCH$_3$, CONH$_2$, or NHCOCH$_3$;

R9, R10 and R11 each is independently H, CH$_3$, F, Cl, Br, I, OCH$_3$, CF$_3$, OCF$_3$, NH$_2$, COOH, CHO, OH, SH, NO$_2$, COCH$_3$, CONH$_2$, NHCOCH$_3$, or

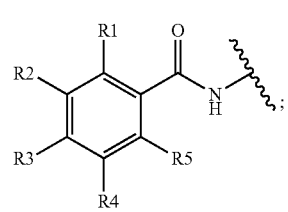

R13 is H, optionally substituted C$_1$-C$_6$ alkyl, optionally substituted C$_1$-C$_6$ haloalkyl, optionally substituted C$_6$-C$_{10}$ aryl, optionally substituted 5, 6, 7, 8 and 9-membered heteroaryl, or halogen; and when R13 is H then R9, R10 or R11 is

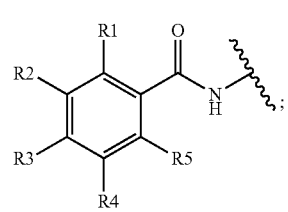

and

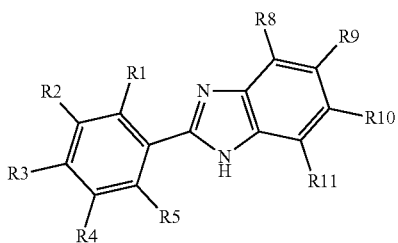

Formula III wherein
R1, R2, R4 and R5 each is independently H, $OCH_3$, $CF_3$, $OCF_3$, $NH_2$, COOH, CHO, OH, SH, $COCH_3$, $CONH_2$, or $NHCOCH_3$;
R3 is H;
R8 and R11 each is independently H, $CH_3$, F, Cl, Br, I, $OCH_3$, $CF_3$, $OCF_3$, $NH_2$, COOH, CHO, OH, SH, $NO_2$, $COCH_3$, $CONH_2$, or $NHCOCH_3$;
R9 is F, Cl, Br, I, $NO_2$, or $CF_3$; and
R10 is H.

The present invention also provides method for treating a subject suffering from a disease associated with sodium channel activity, the method comprising administering to the subject a therapeutically effective amount of a compound according to Formula I, or a tautomer thereof, or a pharmaceutically acceptable salt or solvate of said compound or said tautomer:

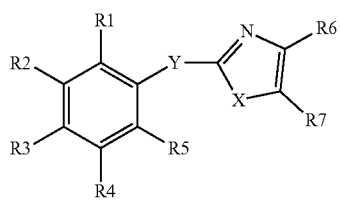

Formula I wherein each of R1, R2, R3, R4 and R5 is, independently, H, optionally substituted $C_1$-$C_6$ alkyl, optionally substituted $C_1$-$C_6$ haloalkyl, optionally substituted $C_6$-$C_{10}$ aryl, optionally substituted 5, 6, 7, 8 and 9-membered heteroaryl, or halogen;
X is C, N, O, or S;
Y is $(CH_2)_n$, where n=0,1,2; CH2CO; NH, O, or S
R1 and/or R5 is H, $CH_3$, F, Cl, Br, I, $OCH_3$, $CF_3$, $OCF_3$, $NH_2$, COOH, CHO, OH, SH, $NO_2$, $COCH_3$, $CONH_2$, or $NHCOCH_3$;
R2 and/or R4 is H, $CH_3$, F, Cl, Br, I, $OCH_3$, $CF_3$, $OCF_3$, $NH_2$, COOH, CHO, OH, SH, NO2, $COCH_3$, $CONH_2$, or $NHCOCH_3$;
R3 is H, $CH_3$, F, Cl, Br, I, $OCH_3$, $CF_3$, $OCF_3$, $NH_2$, COOH, CHO, OH, SH, $NO_2$, $COCH_3$, $CONH_2$, or $NHCOCH_3$;
R6 and/or R7 is H, optionally substituted $C_1$-$C_6$ alkyl containing the requisite number of carbon atoms can be branched or unbranched, optionally substituted $C_1$-$C_6$ haloalkyl containing the requisite number of carbon atoms can be branched or unbranched, optionally substituted $C_6$-$C_{10}$ aryl, or optionally substituted 5, 6, 7, 8 and 9-membered heteroaryl;
or R6 and R7 together with the carbon atom to which they are respectively attached may form a benzo-fused carbocycle or heterocycle.

The compound may be a compound listed in Table 1.

The present invention provides a use of a compound of General Formula I for the manufacture treatment of diseases mediated by modulation of voltage-gated sodium channels including, but not limited to, CNS disorders such as epilepsy, chronic pain and neuropathic pain. The present invention also provides a compound of General Formula I for use in treating diseases mediated by modulation of voltage-gated sodium channels including, but not limited to, CNS disorders such as epilepsy, chronic pain and neuropathic pain.

Each embodiments of the method described herein is also intended as an embodiment for the uses and compound for use described herein.

In some embodiments of the method, the disease associated with sodium channel activity is a seizure disorder, neuropathic pain or chronic pain.

The seizure disorder may be epilepsy. In further embodiments, the epilepsy may be partial epilepsy, generalized absence epilepsy, temporal lobe epilepsy or therapy resistant epilepsy, or any combination thereof.

The seizure disorder may be characterized by acute seizures, chronic seizures, generalized tonic-clonic seizures or refractory seizures. The seizure disorder may be epilepsy characterized by acute seizures, chronic seizures, generalized tonic-clonic seizures or refractory seizures.

The seizure disorder may be therapy resistant.

The therapy resistant epilepsy or therapy resistant seizure disorder may be a pharmaco-resistant epilepsy or a pharmaco-resistant seizure disorder.

In some embodiments, the method may treat a subject suffering from a seizure disorder, a subject suffering from neuropathic pain, or a subject suffering from chronic pain, or a combination thereof.

The method may treat a subject suffering from acute seizures, chronic seizures, generalized tonic-clonic seizures or refractory seizures.

The method may treat a subject suffering from epilepsy. In some embodiments of the method, the subject suffers from partial epilepsy, generalized absence epilepsy, temporal lobe epilepsy or therapy resistant epilepsy, or any combination thereof. The disease may be therapy resistant or the subject may be therapy resistant. The disease may be pharmaco-resistant or the subject may be pharmaco-resistant.

The method may treat a subject suffering from a disease associated with sodium channel isoform NaV1.6 activity, or primarily associated with sodium channel isoform NaV1.6 activity.

The present invention provides compounds and compositions useful for treating diseases and disorders associated with Na channel activity. In one aspect, the compounds block Na channel activity.

The subject may be a mammal. It may be a human or a non-human mammal. In some embodiments, the subject is in need of modulation of sodium channel inactivation. The subject may be in need of a reduced number of sodium channels available for action potential initiation and conduction. The subject may be in need of delayed recovery from sodium channel inactivation.

In various embodiments, the compound modulates sodium channel isoform NaV1.6 selectively over other sodium channel isoforms and may be used accordingly. In further embodiments, the compound modulates NaV1.6 selectively over NaV1.1, NaV1.2, NaV1.3, NaV1.4, NaV1.5, NaV1.7 or NaV1.8 or any other NaV isoform. Various compounds of the present disclosure may have a greater affinity for the inactivated state of a sodium channel than the activated state of the sodium channel. Some compounds may provide a use-dependent sodium channel blocker which may increase inhibition of sodium channels during increased neuronal activity.

In various embodiments of the methods, the compound is an acetate, carbonate, sulphate, citrate, fumarate, hydrochloride, chloride, hydrobromide, bromide, mesylate, methylsulphate, nitrate, oxalate, phosphate, hydrogenphosphate, dihydrogenphosphate, tartrate or tosylate salt. In further embodiments, the compound is a hydrochloride salt.

Preparation of Compounds

Processes for preparing compounds of any of the formulas of the invention or for preparing intermediates useful for preparing compounds of any of the formulas of the invention are provided as further embodiments of the invention. Intermediates useful for preparing compounds of formula I or any other formula disclosed herein are also provided as further embodiments of the invention.

The present application provides methods and compositions for making and testing compounds of the invention as well as for identifying compounds with the desired activity described herein.

Typical embodiments of compounds described herein may be synthesized using the general reaction schemes described below. It will be apparent given the description herein that the general schemes may be altered by substitution of the starting materials with other materials having similar structures to result in products that are correspondingly different. Descriptions of syntheses follow to provide numerous examples of how the starting materials may vary to provide corresponding products. Given a desired product for which the substituent groups are defined, the necessary starting materials generally may be determined by inspection. Starting materials are typically obtained from commercial sources or synthesized using published methods. For synthesizing compounds which are embodiments described in the present disclosure, inspection of the structure of the compound to be synthesized will provide the identity of each substituent group. The identity of the final product will generally render apparent the identity of the necessary starting materials by a simple process of inspection, given the examples herein. In general, compounds described herein are typically stable and isolatable at room temperature and pressure.

The compounds of the invention could be prepared by any method known in the art for the preparation of compounds with analogue structures. The compounds of the invention can be prepared following the procedures here described as well as by the specific methods described or similar processes to either.

It will be appreciated that the experimental conditions in the schemes are illustrative of suitable conditions for performing the transformations shown and that it may be necessary to vary the precise conditions employed for the preparation of compounds of formula (I).

Some of the derivatives of the formula (I) and other formula herein can be prepared by the procedures described in the general methods below or by routine modifications thereof.

The invention also provides synthetic processes and intermediates described herein, which are useful for preparing said compounds.

The compounds of the invention can be better understood if connected with the following synthetic schemes and methods which illustrate a means by which the compounds can be prepared.

The compounds of this invention can be prepared by a variety of synthetic procedures. Representative procedures are shown in, but are not limited to, the following schemes:

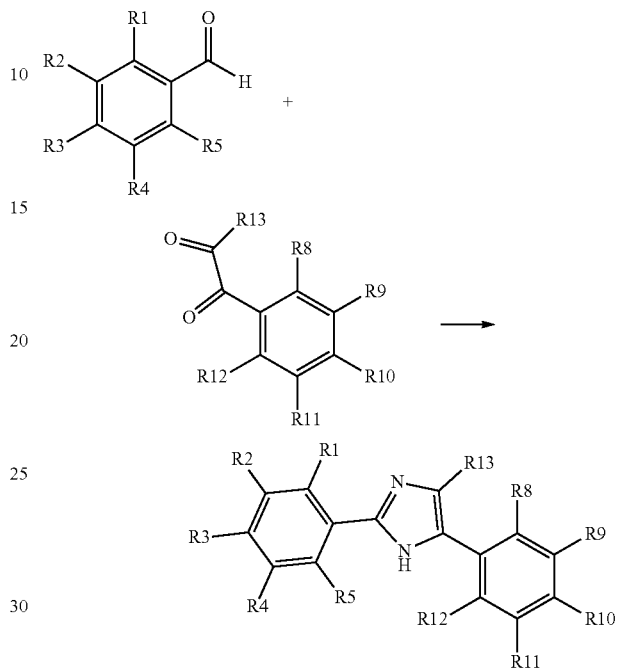

Scheme 1. Synthesis of 2,4(5)-arylimidazoles.

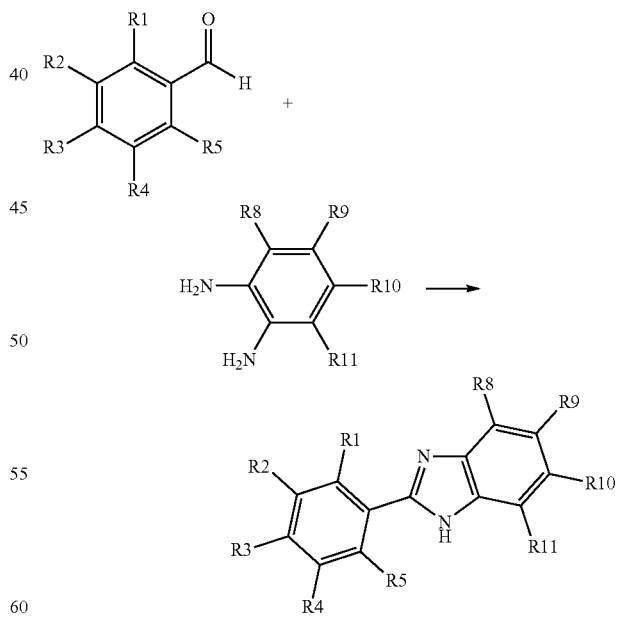

Scheme 2. Synthesis of 2-arylbenzimidazoles.

Each of R1, R2, R3, R4, R5, R8, R9, R10, R11, R12 and R13 is selected, independently, from H, optionally substituted $C_1$-$C_6$ alkyl, optionally substituted $C_1$-$C_6$ haloalkyl, optionally substituted $C_6$-$C_{10}$ aryl, optionally substituted 5, 6, 7, 8 and 9-membered heteroaryl, halogens.

R1 and/or R5 is selected from
H, CH$_3$, F, Cl, Br, I, OCH$_3$, CF$_3$, OCF$_3$, NH$_2$, COOH, CHO, OH, SH, NO$_2$, COCH$_3$, CONH$_2$, NHCOCH$_3$;

R2 and/or R4 is selected from
H, CH$_3$, F, Cl, Br, I, OCH$_3$, CF$_3$, OCF$_3$, NH$_2$, COOH, CHO, OH, SH, NO$_2$, COCH$_3$, CONH$_2$, NHCOCH$_3$;

R3 is selected from
H, CH3, F, Cl, Br, I, OCH$_3$, CF$_3$, OCF$_3$, NH$_2$, COOH, CHO, OH, SH, NO$_2$, COCH$_3$, CONH$_2$, NHCOCH$_3$;

R8 and/or R12 is selected from
H, CH$_3$, F, Cl, Br, I, OCH$_3$, CF$_3$, OCF$_3$, NH$_2$, COOH, CHO, OH, SH, NO$_2$, COCH$_3$, CONH$_2$, NHCOCH$_3$;

R9 and/or R11 is selected from
H, CH$_3$, F, Cl, Br, I, OCH$_3$, CF$_3$, OCF$_3$, NH$_2$, COOH, CHO, OH, SH, NO$_2$, COCH$_3$, CONH$_2$, NHCOCH$_3$;

R10 is selected from
H, CH$_3$, F, Cl, Br, I, OCH$_3$, CF$_3$, OCF$_3$, NH$_2$, COOH, CHO, OH, SH, NO$_2$, COCH$_3$, CONH$_2$, NHCOCH$_3$;

Regarding scheme 1 is provided that when R13 is H or —CH$_3$ or —CH$_2$—CH$_3$ then R9, R10 or R11 can be represented by the formula (a):

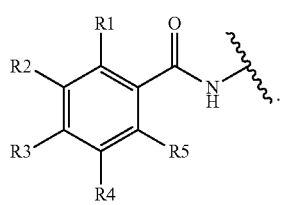

In cases where compounds are sufficiently basic or acidic to form acid or base salts, use of the compounds as salts may be appropriate. Examples of acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Processes for preparing compounds of any of the formulas of the invention are provided as further embodiments of the invention and are illustrated by the following procedures in which the meanings of the generic radicals are as given above unless otherwise qualified.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Suitable salts may also be formed following acid addition to generate non-toxic salts. Examples include the acetate, carbonate, sulphate, citrate, fumarate, hydrochloride, chloride, hydrobromide, bromide, mesylate, methylsulphate, nitrate, oxalate, phosphate, hydrogenphosphate, dihydrogenphosphate, tartrate and tosylate.

Pharmaceutically adequate salts of compounds of formula (I) may be prepared by one or more of three methods:
i. By reacting the compound of formula (I) with the suitable acid or base
ii. By removing any protecting group from a suitable precursor of the compound of formula (I) using the proper acid or base
iii. By converting one salt of the compound of formula (I) into another with the desired acid or base or by means of an appropriate ion exchange column.

All three reactions are typically carried out in solution. The resulting salt may precipitate and then collected by filtration or may be recovered after the solvent has been evaporated.

Combinations

In one embodiment, pharmaceutical compositions comprising a compound disclosed herein, or a pharmaceutically acceptable salt thereof, in combination with one or more (e.g., one, two, three, four, one or two, or one to three, or one to four) additional therapeutic agents, and a pharmaceutically acceptable carrier, diluent or excipient are provided.

The composition of the invention can further comprise additional therapeutic additives, alone or in combination (e.g., 2, 3, or 4 additional additives). Examples of additional additives include but are not limited to: (a) antimicrobials, (b) steroids (e.g., hydrocortisone, triamcinolone); (c) pain medications (e.g., aspirin, an NSAID, and a local anesthetic); (d) anti-inflammatory agents; and (e) combinations thereof.

Examples of antimicrobial agents that can be used in the present invention include, but are not limited to, isoniazid, ethambutol, pyrazinamide, streptomycin, clofazimine, rifabutin, fluoroquinolones, ofloxacin, sparfloxacin, rifampin, azithromycin, clarithromycin, dapsone, tetracycline, erythromycin, cikprofloxacin, doxycycline, ampicillin, amphotericine B, ketoconazole, fluconazole, pyrimethamine, sulfadiazine, clindamycin, lincomycin, pentamidine, atovaquone, paromomycin, diclarazaril, acyclovir, trifluorouridine, foscarnet, penicillin, gentamicin, ganciclovir, iatroconazole, miconazole, Zn-pyrithione, and silver salts, such as chloride, bromide, iodide, and periodate.

Kits

The present invention further provides kits. Kits of the invention comprise at least one compound of the invention, and an instructional material for the use thereof, and optionally an applicator.

In one embodiment, kits comprising a compound disclosed herein, or a pharmaceutically acceptable salt thereof, in combination with one or more (e.g., one, two, three, four, one or two, or one to three, or one to four) additional therapeutic agents are provided. The term "pharmaceutically acceptable salt" includes hydrates and other solvates, as well as salts in crystalline or non-crystalline form. Where a particular pharmaceutically acceptable salt is disclosed, it is understood that the particular salt (e.g., a hydrochloride salt) is an example of a salt, and that other salts may be formed using techniques known to one of skill in the art. Additionally, one of skill in the art would be able to convert the pharmaceutically acceptable salt to the corresponding compound, free base and/or free acid, using techniques generally known in the art. See also: Stahl and Wermuth, C. G. (Editors), Handbook of Pharmaceutical Salts, Wiley-VCH, Weinheim, Germany, 2008.

As used herein, an "instructional material" includes a publication, a recording, a diagram, or any other medium of expression which can be used to communicate the usefulness of the composition of the invention for its designated use. The instructional material of the kit of the invention may, for example, be affixed to a container which contains the composition or be shipped together with a container which contains the composition. Alternatively, the instructional material may be shipped separately from the container with the intention that the instructional material and the composition be used cooperatively by the recipient.

The method of the invention includes a kit comprising a compound identified in the invention and an instructional material which describes administering the compound or a composition comprising the compound to a cell or a subject to any target of interest, such as a surface. This should be construed to include other embodiments of kits that are known to those skilled in the art, such as a kit comprising a solvent, such as a sterile solvent, suitable for dissolving or suspending the composition of the invention prior to administering the compound to a cell or a subject. In some embodiments the subject is a human.

Administration

The compounds of any of the formulas of the invention can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

It will be appreciated that compounds of the invention can be administered using various kinds of delivery systems and media. Furthermore, compounds of the invention can be administered in combination with other therapeutic agents and compounds and can be used with other kinds of treatments.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin;

excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant.

Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be useful to include isotonic agents, for example, sugars, buffers or sodium chloride. Prolonged absorption of the injectable compositions can be brought about by the use in the compositions of agents delaying absorption, for example, aluminum monostearate, and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, typical methods of preparation are vacuum drying and the freeze-drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of a formula of the invention to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

The compounds of the invention may be administered as prodrugs. Thus, certain derivatives (referred as prodrugs) of compounds of formula (I) can, after being administered systemically, be converted into compounds of formula (I) having the desired activity, for example by hydrolytic cleavage.

Dosages

Useful dosages of the compounds of a formula of the invention can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) of a formula of the invention in a liquid composition, such as a lotion, will be from about 0.1-25 wt-%, and can be from about 0.5-10 wt-%. The concentration in a semi-solid or solid composition such as a gel or a powder will be about 0.1-5 wt-%, and can be about 0.5-2.5 wt %.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, can be in the range of 6 to 90 mg/kg/day, and can be in the range of 15 to 60 mg/kg/day.

The compound is conveniently administered in unit dosage form; for example, containing 5 to 1000 mg, conveniently 10 to 750 mg, most conveniently, 50 to 500 mg of active ingredient per unit dosage form.

Ideally, when the active ingredient needs to enter circulation and be delivered via blood, the active ingredient, in one embodiment, should be administered to achieve peak plasma concentrations of the active compound of can be from about 0.5 to about 75 µM, can be from about 1 to 50 µM, and can be from about 2 to about 30 µM. This may be achieved, for example, by the intravenous injection of a 0.05 to 5% solution of the active ingredient, optionally in saline, or orally administered as a bolus containing about 1-100 mg of the active ingredient. Desirable blood levels may be maintained by continuous infusion to provide about 0.01-5.0 mg/kg/hr or by intermittent infusions containing about 0.4-15 mg/kg of the active ingredient(s).

The desired dose may conveniently be presented in a single dose or as divided doses administered at appropriate intervals, for example, as two, three, four, or more sub-doses per day. The sub-dose itself may be further divided, e.g., into a number of discrete loosely spaced administrations; such as multiple inhalations from an insufflator or by application of a plurality of drops into the eye.

In another embodiment, a formulation of the invention can be impregnated into a dressing material (or otherwise contained or encompassed by the dressing material). The dressing material is a pharmaceutically acceptable fabric. It can be, for example, gauze or any other type of medical fabric or material that can be used to cover a wound and/or to keep a therapeutic agent or composition in contact with a patient.

In another embodiment of the invention, the compound is controllably released into a subject when the composition of the invention is implanted into a subject, due to bioresorption relying on the time scale resulting from cellular remodeling. In one aspect, the composition may be used to replace an area of discontinuity in the tissue. The area of discontinuity can be the result of trauma, a disease, disorder, or condition, surgery, injury, etc.

In accordance with the present invention, as described above or as discussed in the Examples below, there can be employed conventional chemical, cellular, histochemical, biochemical, molecular biology, microbiology, and in vivo techniques which are known to those of skill in the art. Such techniques are explained fully in the literature.

Without further description, it is believed that one of ordinary skill in the art can, using the preceding description and the following illustrative examples, make and utilize the compounds of the present invention.

Other useful techniques that can be practiced with the present invention can be found in the art, such as in Rossignol et al. (WO2007081974).

The disclosures of each and every patent, patent application, and publication cited herein are hereby incorporated by reference herein in their entirety.

Headings are included herein for reference and to aid in locating certain sections. These headings are not intended to limit the scope of the concepts described therein under, and these concepts may have applicability in other sections throughout the entire specification.

While this invention has been disclosed with reference to specific embodiments, it is apparent that other embodiments and variations of this invention may be devised by others skilled in the art without departing from the true spirit and scope of the invention.

The invention is now described with reference to the following Examples. The following working examples therefore, are provided for the purpose of illustration only and specifically point out certain embodiments of the present invention, and are not to be construed as limiting in any way the remainder of the disclosure. Therefore, the examples should be construed to encompass any and all variations which become evident as a result of the teaching provided herein.

The terms and expressions that have been employed are used as terms of description and not of limitation, and there is no intention in the use of such terms and expressions of excluding any equivalents of the features shown and described or portions thereof, but it is recognized that various modifications are possible within the scope of the embodiments of the present disclosure. Thus, it should be understood that although the present disclosure has been specifically disclosed by specific embodiments and optional features, modification and variation of the concepts herein disclosed may be resorted to by those of ordinary skill in the art, and that such modifications and variations are considered to be within the scope of embodiments of the present disclosure

EXAMPLES

Method 1

General Procedure for the Preparation of Benzimidazoles

A mixture of o-phenylendiamine (1.0 mmol), arylaldehyde (2.0 mmol) and ammonium acetate (3.0 mmol) in absolute ethanol (3.0 mL) was prepared in a sealed 10 mL vial. The mixture was irradiated for 5 min, setting the temperature at 120° C. and the maximal power output at 100 W. During this period, the reaction vessel was stirred and cooled. The reaction is followed by TLC (DCM/EtOAc 10/1). If necessary an additional mmole of arylaldehyde is added and the mixture is irradiated for an additional 5 min under the same conditions. The solvent was evaporated and the residue was partitioned between saturated aqueous NaHCO3 solution (20 mL) and Ethylacetate (20 mL). The organic phase was dried over Na2SO4 and the solvent was removed in vacuo. The free base is then crystallized from DCM/Hex and then the hydrochloride salts were prepared by treating the free base with an ethanolic HCl 5% w/w solution. The resulting salts were crystallized from absolute ethanol/dry diethyl ether.

Method 2

General Procedure for the Preparation of Diphenyl Imidazoles

A mixture of arylaldehyde (0.7 mmol) the appropriate diketo compound (0.7 mmol) and ammonium acetate (3.41 mmol, 262 mg) in methanol (3.5 mL) was stirred overnight at room temperature, then the solvent was evaporated and the residue was partitioned between saturated aqueous NaHCO3 solution and methylene chloride. The organic phase was dried over Na2SO4 and the solvent was removed in vacuo. The selective isolation of either non-basic (2-aroyl-4(5)-arylimidazoles) or basic (2,4(5)-diarylimidazoles) compounds from the crude reaction mixture was obtained using SCX-2 column (2 g, 30-90 μm, loading 0.4 meq/g). The column is prewashed with DCM:methanol=1:1 (10 mL), the non-basic products were eluted with methanol (10 mL) and then the desired 2,4(5)-diphenylimidazoles were eluted with a methanolic ammonia 5% w/w solution (10 mL). The hydrochloride salts were prepared by treating the free base with an ethanolic HCl 5% w/w solution. The products were then crystallized from absolute ethanol/dry diethyl ether.

Example 1

Preparation of 2,5-Diphenyl-4-methyl-1H-imidazole

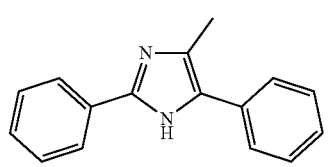 [SMILES: Cc1nc(-c2ccccc2)[nH]c1-c1ccccc1]

Method 2 was applied using benzaldehyde and 1-phenyl-1,2-propanedione to produce 2,5-Diphenyl-4-methyl-1H-imidazole.

Example 2

Preparation of 2-Phenyl-benzimidazole

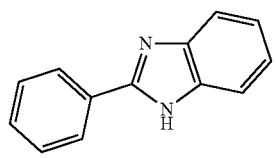 [SMILES: c1ccc(-c2nc3ccccc3[nH]2)cc1]

Method 1 was applied using benzaldehyde and 1,2-phenylendiamine to produce 2-Phenyl-benzimidazole (yield 50%).

Example 3

Preparation of 2-(4-methoxyphenyl)-benzimidazole

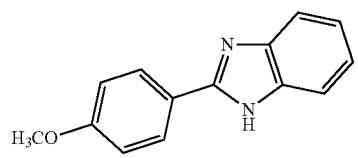 [SMILES: COc1ccc(-c2nc3ccccc3[nH]2)cc1]

Method 1 was applied using 4-methoxybenzaldehyde and 1,2-phenylendiamine to produce 2-(4-methoxyphenyl)-benzimidazole (yield 59%)

Example 4

Preparation of 2-(4-chlorophenyl)-4-methyl-5-phenyl-1H-imidazole

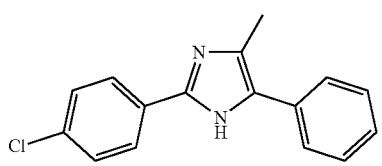 [SMILES: Cc1nc(-c2ccc(Cl)cc2)[nH]c1-c1ccccc1]

Method 2 was applied using 4-chlorobenzaldehyde and 1-phenyl-1,2-propanedione to produce 2-(4-chlorophenyl)-4-methyl-5-phenyl-1H-imidazole.

1H NMR (300 MHz, DMSO-d6) δ 2.51 (3H, s), 7.47-7.51 (1H, t), 7.55-7.60 (2H, t), 7.73-7.77 (4H, m), 8.29-8.32 (2H, d); MS (ESI+): m/z 269.7 [M+H]+.

Example 5

Preparation of 2-(3-chlorophenyl)-4-methyl-5-phenyl-1H-imidazole

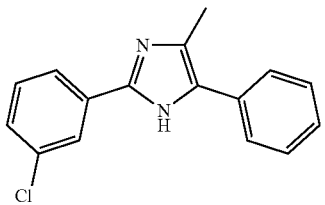 [SMILES: Cc1nc(-c2cccc(Cl)c2)[nH]c1-c1ccccc1]

Method 2 was applied using 3-chlorobenzaldehyde and 1-phenyl-1,2-propanedione to produce 2-(3-chlorophenyl)-4-methyl-5-phenyl-1H-imidazole.

1H NMR (300 MHz, DMSO-d6) δ 2.52 (3H, s), 7.47-7.52 (1H, t), 7.56-7.61 (2H, t), 7.68-7.77 (4H, m), 8.21-8.25 (1H, m), 8.38-8.39 (1H, m); MS (ESI+): m/z 269.7 [M+H]+.

Example 6

Preparation of 2-(3-chlorophenyl)-1H-imidazole

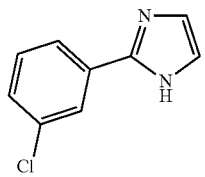 [SMILES: Clc1cccc(-c2ncc[nH]2)c1]

Method 2 was applied using 3-chlorobenzaldehyde and glyoxal to produce 2-(3-chlorophenyl)-1H-imidazole (yield 57%, mp.(oxalate) 183-186° C.).

1H NMR (300 MHz, DMSO-d6) δ 7.29 (2H, s), 7.42-7.54 (2H, m), 7.89-7.93 (1H, d), 8.00 (1H, s); MS (ESI+): m/z 179.2 [M+H]+.

Example 7

Preparation of 2-(3-methoxyphenyl)-4-methyl-1H-imidazole

Method 2 was applied using 3-methoxybenzaldehyde and methylglyoxal to produce 2-(3-methoxyphenyl)-4-methyl-1H-imidazole (yield 39%, mp.(oxalate) 169-172° C.).

Example 8

Preparation of 2-(3-methoxyphenyl)-4,5-dimethyl-1H-imidazole

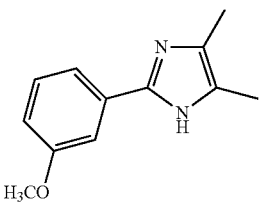

Method 2 was applied using 3-methoxybenzaldehyde and 1,2-propanedione to produce 2-(3-methoxyphenyl)-4,5-dimethyl-1H-imidazole (yield 53%, mp.(oxalate) 225-228° C.).

1H NMR (300 MHz, DMSO-d6) δ 2.22 (6H, s), 3.82 (3H, s), 7.03-7.06 (1H, d), 7.42-7.54 (3H, m); MS (ESI+): m/z 203.3 [M+H]+.

Example 9

Preparation of N-{4-[2-(4-methoxyphenyl)-1H-imidazol-5-yl]phenyl}benzamide

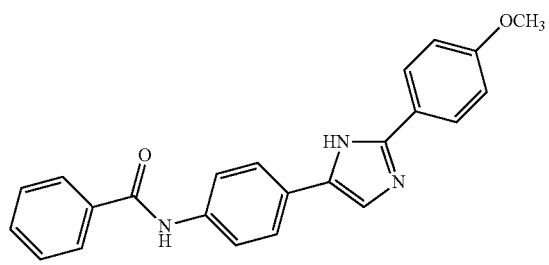 [SMILES: COc1ccc(-c2ncc(-c3ccc(NC(=O)c4ccccc4)cc3)[nH]2)cc1]

Method 2 was applied using 4-methoxybenzaldehyde and N-[4-(2-oxoacetyl)phenyl]benzamide to produce N-{4-[2-(4-methoxyphenyl)-1H-imidazol-5-yl]phenyl}benzamide (yield 60%, mp.(hydrochloride) >300° C.).

1H NMR (300 MHz, DMSO-d6) δ 3.89 (3H, s), 7.25 (2H, m), 7.58 (3H, m), 7.97 (6H, m), 8.17 (3H, m); MS (ESI+): m/z 370.4 [M+H]+.

Example 10

Preparation of N-{3-[2-(4-methoxyphenyl)-1H-imidazol-5-yl]phenyl}benzamide

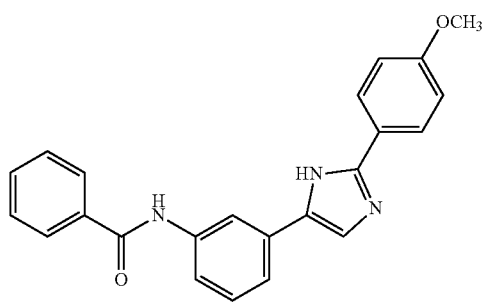 [SMILES: COc1ccc(-c2ncc(-c3cccc(NC(=O)c4ccccc4)c3)[nH]2)cc1]

Method 2 was applied using 4-methoxybenzaldehyde and N-[3-(2-oxoacetyl)phenyl]benzamide to produce N-{3-[2-(4-methoxyphenyl)-1H-imidazol-5-yl]phenyl}benzamide (yield 62%, mp.(hydrochloride) 274-277° C.).

1H NMR (300 MHz, DMSO-d6) δ 3.88 (3H, s), 7.22 (2H, d), 7.58 (4H, m), 7.75 (2H, t), 8.03 (2H, d), 8.13 (1H, s), 8.27 (2H, m), 8.38 (1H, s); MS (ESI+): m/z 370.4 [M+H]+.

Example 11

Evaluation of compounds for % block of Nav1.6 at 100 μM

Compounds of the present invention were tested in an assay for % block of Nav1.6 at a concentration of 100 μM compound. Compounds tested and their % block is set forth in Table 1. Table 1 also indicates the melting point ranges for some compounds.

As shown in Table 1, certain compounds of MV1060-MV1091 series demonstrate high % block of NaV1.6. Some such compounds correspond to a compound of Formula III, wherein R9 is substituted with a halogen, a nitro or a $CF_3$ group. In comparing MV1089, MV1090 and MV1091, it is shown that compounds of Formula III where R3 is H result in higher % block than when R3 is substituted, e.g., by $OCH_3$. In comparing MV1066, MV1084, MV1085, MV1086, MV1087 and MV1088, it is shown that compounds of Formula III where R9 is halogen, a nitro or a $CF_3$ group result in higher % block than when R9 is $OCH_3$, COOH or $CH_3$. Table 2 shows $IC_{50}$ values of certain compounds of MV1060-MV1091.

As also shown in Table 1, compounds of the MV1501-MV1509 series demonstrate high % block of NaV1.6. Such compounds correspond to a compound of Formula II, wherein R13 is $C_1$-$C_6$ alkyl or, more specifically, methyl. MV1504 and MV1505, which correspond to a compound of Formula II where R3 is H, show a higher % block than MV1501 and MV1502, which correspond to a compound of Formula II where R3 is Cl or $OCH_3$, respectively.

TABLE 1

Table of Compounds

| COMP. | STRUCTURE | CHEMICAL NAME | % block NaV1.6 at 100 μM |
|---|---|---|---|
| MV1060 Example 2 | 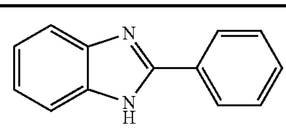 | 2-PHENYLBENZIMIDAZOLE | 30 |
| MV1061 | 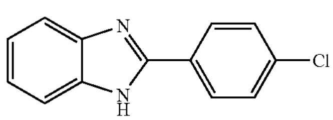 [SMILES: Clc1ccc(-c2nc3ccccc3[nH]2)cc1] | 2-(4-chlorophenyl)-1H-1,3-benzodiazole | 45 |
| MV1062 Example 3 | 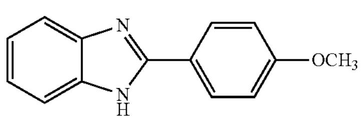 [SMILES: COc1ccc(-c2nc3ccccc3[nH]2)cc1] | 2-(4-methoxyphenyl)-1H-1,3-benzodiazole | 70 |
| MV1066 | 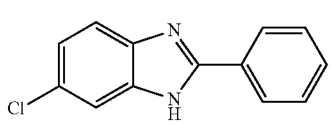 [SMILES: Clc1ccc2nc(-c3ccccc3)[nH]c2c1] | 6-chloro-2-phenyl-1H-1,3-benzodiazole | 95 |
| MV1068 | 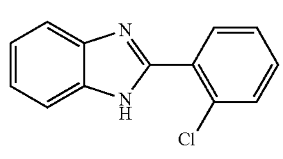 [SMILES: Clc1ccccc1-c1nc2ccccc2[nH]1] | 2-(2-chlorophenyl)-1H-1,3-benzodiazole | 75 |

TABLE 1-continued

Table of Compounds

| MV1069 | 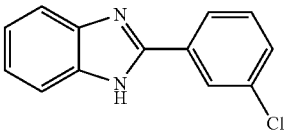 [SMILES: Clc1cccc(-c2nc3ccccc3[nH]2)c1] | 2-(3-chlorophenyl)-1H-1,3-benzodiazole | 65 |
| --- | --- | --- | --- |
| MV1070 | 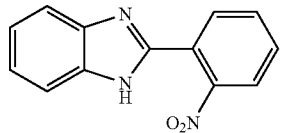 | 2-(2-nitrophenyl)-1H-1,3-benzodiazole | 20 |
| MV1071 | 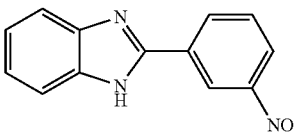 | 2-(3-nitrophenyl)-1H-1,3-benzodiazole | 30 |
| MV1072 | 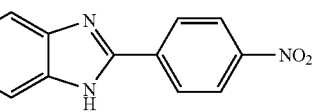 | 2-(4-nitrophenyl)-1H-1,3-benzodiazole | 20 |
| MV1073 |  | 2-(2-methoxyphenyl)-1H-1,3-benzodiazole | 40 |
| MV1074 | 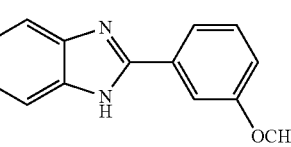 | 2-(3-methoxyphenyl)-1H-1,3-benzodiazde | 40 |
| MV1075 | 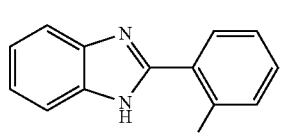 | 2-(2-trifluoromethylphenyl)-1H-1,3-benzodiazole | 20 |
| MV1076 | 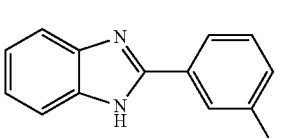 | 2-(3-trifluoromethylphenyl)-1H-1,3-benzodiazole | 60 |
| MV1077 | 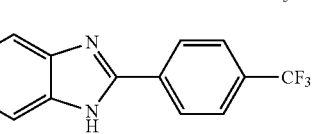 | 2-(4-trifluoromethylphenyl)-1H-1,3-benzodiazole | 15 |
| MV1078 | 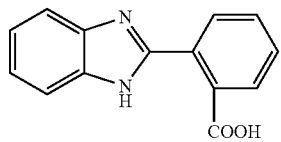 [SMILES: O=C(O)c1ccccc1-c1nc2ccccc2[nH]1] | 2-(1H-1,3-benzodiazol-2-yl)benzoic acid | 5 |
| MV1079 | 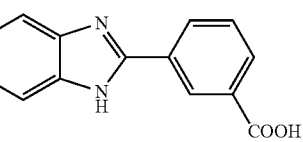 | 3-(1H-1,3-benzodiazol-2-yl)benzoic acid | 15 |

TABLE 1-continued

Table of Compounds

| MV1080 | 4-(1H-1,3-benzodiazol-2-yl)benzoic acid | 10 |
| MV1081 | 2-(2-methylphenyl)-1H-1,3-benzodiazole | 25 |
| MV1082 | 2-(3-methylphenyl)-1H-1,3-benzodiazole | 65 |
| MV1083 | 2-(4-methylphenyl)-1H-1,3-benzodiazole | 30 |
| MV1084 | 6-nitro-2-phenyl-1H-1,3-benzodiazole | 70 |
| MV1085 | 6-methoxy-2-phenyl-1H-1,3-benzodiazole | 35 |
| MV1086 | 6-trifluoromethyl-2-phenyl-1H-1,3-benzodiazole | 90 |
| MV1087 | 2-phenyl-1H-1,3-benzodiazole-6-carboxylic acid | 0 |
| MV1088 | 6-methyl-2-phenyl-1H-1,3-benzodiazole | 55 |
| MV1089 | 6-chloro-2-(2-methoxyphenyl)-1H-1,3-benzodiazole | 90 |
| MV1090 | 6-chloro-2-(3-methoxyphenyl)-1H-1,3-benzodiazole | 85 |

TABLE 1-continued

Table of Compounds

| COMP. | STRUCTURE | | |
|---|---|---|---|
| MV1091 | 6-chloro-2-(4-methoxyphenyl)-1H-1,3-benzodiazole | | 0 |

| COMP. | STRUCTURE | MP (° C.) | % block NaV1.6 at 100 ∝ M |
|---|---|---|---|
| MV1301 | (structure) ·HCl | 320-323 | 0 |
| MV1302 Example 9 | (structure) ·HCl | 312-314 | 20 |
| MV1303 | (structure) ·HCl | 309-311 | 0 |
| MV1304 | (structure) ·HCl | 307-309 | 40 |
| MV1305 | (structure) ·HCl | >330 | 50 |
| MV1306 | (structure) ·HCl | >330 | 10 |
| MV1307 | (structure) ·HCl | 221-223 | 25 |
| MV1308 Example 10 | (structure) ·HCl | 268-270 | 75 |

TABLE 1-continued

Table of Compounds

| COMP. | STRUCTURE | | |
|---|---|---|---|
| MV1309 | (4-methoxybenzamide, 3-(2-phenyl-1H-imidazol-4-yl)phenyl) ·HCl | 255-258 | 75 |
| MV1310 | (4-methoxybenzamide, 3-[2-(4-methoxyphenyl)-1H-imidazol-4-yl]phenyl) ·HCl | 207-209 | 60 |
| MV1311 | (4-chlorobenzamide, 3-(2-phenyl-1H-imidazol-4-yl)phenyl) ·HCl | 295-298 | 90 |
| MV1312 | (4-chlorobenzamide, 3-[2-(4-methoxyphenyl)-1H-imidazol-4-yl]phenyl) ·HCl | 290-292 | 85 |

| COMP. | STRUCTURE | CHEMICAL NAME | FORMULA MW |
|---|---|---|---|
| MV1301 | benzamide, 4-(2-phenyl-1H-imidazol-4-yl)phenyl ·HCl | N-[4-(2-PHENYL-1H-IMIDAZOL-4-YL)-PHENYL]-BENZAMIDE HYDRO-CHLORIDE | C22H17N3O *HCl MW = 375.85 |
| MV1302 Example 9 | benzamide, 4-[2-(4-methoxyphenyl)-1H-imidazol-4-yl]phenyl ·HCl | N-{4-[2-(4-METHOXY-PHENYL)-1H-IMIDAZOL-4-YL]-PHENYL}-BENZAMIDE HYDRO-CHLORIDE | C23H19N3O2 *HCl MW = 405.88 |
| MV1303 | 4-methoxybenzamide, 4-(2-phenyl-1H-imidazol-4-yl)phenyl ·HCl | 4-METHOXY-N-[4-(2-PHENYL-1H-IMIDAZOL-4-YL)-PHENYL]-BENZAMIDE HYDRO-CHLORIDE | C23H19N3O2 *HCl MW = 405.88 |
| MV1304 | 4-methoxybenzamide, 4-[2-(4-methoxyphenyl)-1H-imidazol-4-yl]phenyl ·HCl | 4-METHOXY-N-{4-[2-(4-METHOXY-PHENYL)-1H-IMIDAZOL-4-YL]-PHENYL}-BENZAMIDE HYDRO-CHLORIDE | C24H21N3O3 *HCl MW = 435.9 |

TABLE 1-continued

Table of Compounds

| MV1305 | | 4-CHLORO-N-[4-(2-PHENYL-1H-IMIDAZOL-4-YL)-PHENYL]-BENZAMIDE HYDROCHLORIDE | C22H16N3OCl *HCl MW = 410.29 |
|---|---|---|---|
| MV1306 | | 4-CHLORO-N-{4-[2-(4-METHOXY-PHENYL)-1H-IMIDAZOL-4-YL]-PHENYL}-BENZAMIDE HYDROCHLORIDE | C23H18N3O2Cl *HCl MW = 440.32 |
| MV1307 | | N-[3-(2-PHENYL-1H-IMIDAZOL-4-YL)-PHENYL]-BENZAMIDE HYDROCHLORIDE | C22H17N3O *HCl MW = 375.85 |
| MV1308 Example 10 | | N-{3-[2-(4-METHOXY-PHENYL)-1H-IMIDAZOL-4-YL]-PHENYL}-BENZAMIDE HYDROCHLORIDE | C23H19N3O2 *HCl MW = 405.88 |
| MV1309 | | 4-METHOXY-N-[3-(2-PHENYL-1H-IMIDAZOL-4-YL)-PHENYL]-BENZAMIDE HYDROCHLORIDE | C23H19N3O2 *HCl MW = 405.88 |
| MV1310 | | 4-METHOXY-N-{3-[2-(4-METHOXY-PHENYL)-1H-IMIDAZOL-4-YL]-PHENYL}-BENZAMIDE HYDROCHLORIDE | C24H21N3O3 *HCl MW = 435.9 |
| MV1311 | | 4-CHLORO-N-[3-(2-PHENYL-1H-IMIDAZOL-4-YL)-PHENYL]-BENZAMIDE HYDROCHLORIDE | C22H16N3OCl *HCl MW = 410.29 |
| MV1312 | | 4-CHLORO-N-{3-[2-(4-METHOXY-PHENYL)-1H-IMIDAZOL-4-YL]-PHENYL}-BENZAMIDE HYDROCHLORIDE | C23H18N3O2Cl *HCl MW = 440.32 |

TABLE 1-continued

Table of Compounds

| COMP. | STRUCTURE | CHEMICAL NAME | FORMULA MW | MP (° C.) | % block NaV1.6 at 100 ∝ M |
|---|---|---|---|---|---|
| MV1350 | 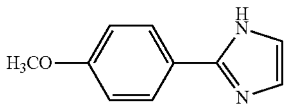 | 2-(4-METHOXY-PHENYL)-1H-IMIDAZOLE OXALATE | C10H10N2O *C2H2O4 MW = 264.23 | 193-195 | 25 |
| MV1351 | 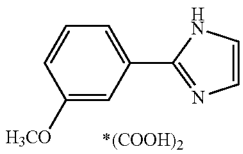 | 2-(3-METHOXY-PHENYL)-1H-IMIDAZOLE OXALATE | C10H10N2O *C2H2O4 MW = 264.23 | 185-188 | 25 |
| MV1352 | 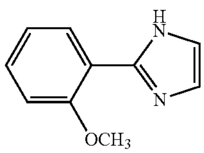 | 2-(2-METHOXY-PHENYL)-1H-IMIDAZOLE OXALATE | C10H10N2O *C2H2O4 MW = 264.23 | 144-146 | 30 |
| MV1353 | 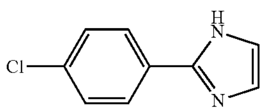 | 2-(4-CHLORO-PHENYL)-1H-IMIDAZOLE OXALATE | C9H7N2Cl *C2H2O4 MW = 268.65 | 238-240 | 30 |
| MV1354 Example 6 | 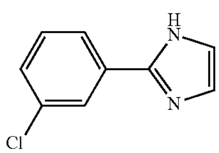 | 2-(3-CHLORO-PHENYL)-1H-IMIDAZOLE OXALATE | C9H7N2Cl *C2H2O4 MW = 268.65 | 183-186 | 20 |
| MV1355 | 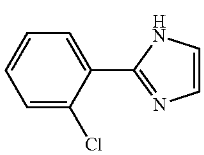 | 2(2-CHLORO-PHENYL)-1H-IMIDAZOLE OXALATE | C9H7N2Cl *C2H2O4 MW = 268.65 | 168-171 | 0 |
| MV1356 | 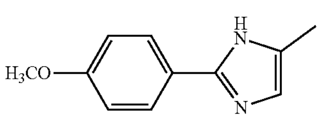 | 2-(4-METHOXY-PHENYL)-5-METHYL-1H-IMIDAZOLE OXALATE | C11H12N2O *C2H2O4 MW = 278.26 | 189-192 | 65 |
| MV1357 Example 7 | 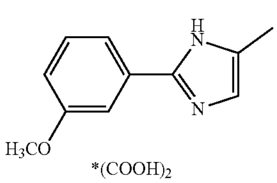 | 2-(3-METHOXY-PHENYL)-5-METHYL-1H-IMIDAZOLE OXALATE | C11H12N2O *C2H2O4 MW = 278.26 | 169-172 | 90 |

TABLE 1-continued

Table of Compounds

| MV1358 | | 2-(2-METHOXY-PHENYL)-5-METHYL-1H-IMIDAZOLE OXALATE | C11H12N2O *C2H2O4 MW = 278.26 | 178-180 | 50 |
|---|---|---|---|---|---|
| MV1359 | | 2-(4-CHLORO-PHENYL)-5-METHYL-1H-IMIDAZOLE OXALATE | C10H9N2Cl *C2H2O4 MW = 282.67 | 210-213 | 75 |
| MV1360 | | 2-(3-CHLORO-PHENYL)-5-METHYL-1H-IMIDAZOLE OXALATE | C10H9N2Cl *C2H2O4 MW = 282.67 | 213-215 | 70 |
| MV1361 | | 2-(2-CHLORO-PHENYL)-5-METHYL-1H-IMIDAZOLE OXALATE | C10H9N2Cl *C2H2O4 MW = 282.67 | 188-190 | 0 |
| MV1362 | | 2-(4-METHOXY-PHENYL)-4,5-DIMETHYL-1H-IMIDAZOLE OXALATE | C12H14N2O *C2H2O4 MW = 292.28 | 218-221 | 85 |
| MV1363 Example 8 | | 2-(3-METHOXY-PHENYL)-4,5-DIMETHYL-1H-IMIDAZOLE OXALATE | C12H14N2O *C2H2O4 MW = 292.28 | 225-228 | 80 |
| MV1364 | | 2-(2-METHOXY-PHENYL)-4,5-DIMETHYL-1H-IMIDAZOLE OXALATE | C12H14N2O *C2H2O4 MW = 292.28 | 204-207 | 70 |
| MV1365 | | 2-(4-CHLORO-PHENYL)-4,5-DIMETHYL-1H-IMIDAZOLE OXALATE | C11H11N2Cl *C2H2O4 MW = 296.70 | 226-228 | 85 |

TABLE 1-continued

Table of Compounds

| | | | | | |
|---|---|---|---|---|---|
| MV1366 | 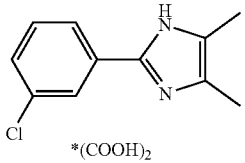 | 2-(3-CHLORO-PHENYL)-4,5-DIMETHYL-1H-IMIDAZOLE OXALATE | C11H11N2Cl *C2H2O4 MW = 296.70 | 228-231 | 95 |
| MV1367 | 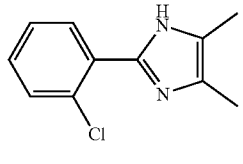 | 2-(2-CHLORO-PHENYL)-4,5-DIMETHYL-1H-IMIDAZOLE OXALATE | C11H11N2Cl *C2H2O4 MW = 296.70 | 220-222 | 45 |
| MV1368 | 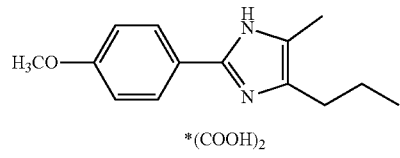 [SMILES: CCCc1nc(-c2ccc(OC)cc2)[nH]c1C] | 2-(4-METHOXY-PHENYL)-5-METHYL-4-PROPYL-1H-IMIDAZOLE OXALATE | C14H18N2O *C2H2O4 MW = 320.34 | 167-170 | 85 |
| MV1369 | 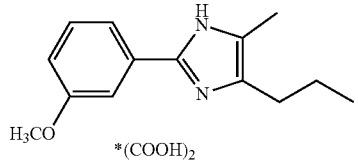 [SMILES: CCCc1nc(-c2cccc(OC)c2)[nH]c1C] | 2-(3-METHOXY-PHENYL)-5-METHYL-4-PROPYL-1H-IMIDAZOLE OXALATE | C14H18N2O *C2H2O4 MW = 320.34 | 130-133 | 100 |
| MV1370 | 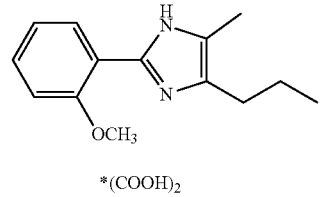 [SMILES: CCCc1nc(-c2ccccc2OC)[nH]c1C] | 2-(2-METHOXY-PHENYL)-5-METHYL-4-PROPYL-1H-IMIDAZOLE OXALATE | C14H18N2O *C2H2O4 MW = 320.34 | 134-137 | 90 |
| MV1371 | 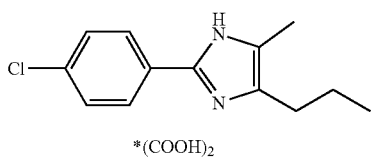 [SMILES: CCCc1nc(-c2ccc(Cl)cc2)[nH]c1C] | 2-(4-CHLORO-PHENYL)-5-METHYL-4-PROPYL-1H-IMIDAZOLE OXALATE | C13H15N2Cl *C2H2O4 MW = 324.75 | 141-144 | 100 |
| MV1372 | 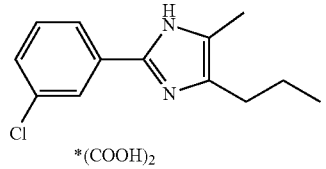 [SMILES: CCCc1nc(-c2cccc(Cl)c2)[nH]c1C] | 2-(3-CHLORO-PHENYL)-5-METHYL-4-PROPYL-1H-IMIDAZOLE OXALATE | C13H15N2Cl *C2H2O4 MW = 324.75 | 181-183 | 100 |
| MV1374 | 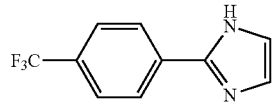 | 2-(4-TRIFLUOROMETHYL-PHENYL)-1H-IMIDAZOLE | C10H7F3N2 MW = 212.21 | 205-207 | nd |
| MV1375 | 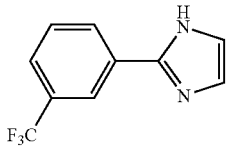 | 2-(3-TRIFLUOROMETHYL-PHENYL)-1H-IMIDAZOLE | C10H7F3N2 MW = 212.21 | 208-211 | nd |

TABLE 1-continued

Table of Compounds

| COMP. | STRUCTURE | NAME | FORMULA | MP (° C.) | % block NaV1.6 at 100 μM |
|---|---|---|---|---|---|
| MV1377 | 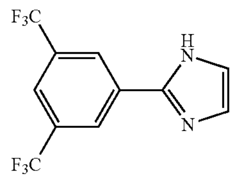 [SMILES: FC(F)(F)c1cc(-c2ncc[nH]2)cc(C(F)(F)F)c1] | 2-(3,5-diTRIFLUORO-METHYL-PHENYL)-1H-IMIDAZOLE | C11H6F5N2 MW = 280.20 | 247-251 | nd |
| MV1378 | 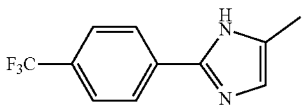 [SMILES: Cc1cnc(-c2ccc(C(F)(F)F)cc2)[nH]1] | 2-(4-TRIFLUOROMETHYL-PHENYL)-5-METHYL-1H-IMIDAZOLE | C11H9F3N2 MW = 226.23 | 189-193 | nd |
| MV1379 | 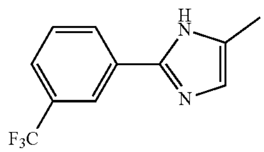 [SMILES: Cc1cnc(-c2cccc(C(F)(F)F)c2)[nH]1] | 2-(3-TRIFLUOROMETHYL-PHENYL)-5-METHYL-1H-IMIDAZOLE | C11H9F3N2 MW = 226.23 | 152-154 | nd |

| COMP. | STRUCTURE | MP (° C.) | % block NaV1.6 at 100 μM |
|---|---|---|---|
| MV1501 | 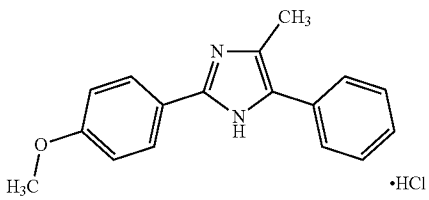 [SMILES: COc1ccc(-c2nc(C)c(-c3ccccc3)[nH]2)cc1 ; Cl] | 245-248 | 90 |
| MV1502 Example 4 | 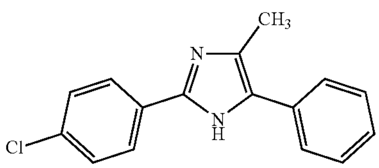 | 266-268 | 95 |
| MV1503 | 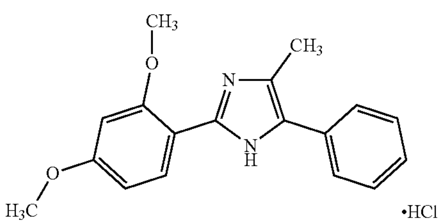 [SMILES: COc1ccc(-c2nc(C)c(-c3ccccc3)[nH]2)c(OC)c1 ; Cl] | 239-241 | nd |
| MV1504 | 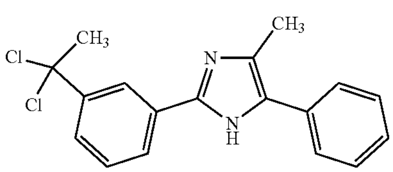 | 271-274 | 100 |
| MV1505 Example 5 | 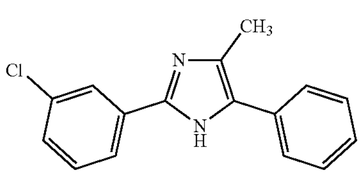 | 224-227 | 100 |

TABLE 1-continued

Table of Compounds

| COMP. | STRUCTURE | | |
|---|---|---|---|
| MV1506 | [structure: 2-phenyl-4-methyl-5-(3-trifluoromethylphenyl)-1H-imidazole ·HCl] | 239-242 | nd |
| MV1507 | [structure: 2-(4-methoxy-2-hydroxyphenyl)-4-methyl-5-phenyl-1H-imidazole ·HCl] | 285-287 | nd |
| MV1508 | [structure: 2-(4-methoxy-3-hydroxyphenyl)-4-methyl-5-phenyl-1H-imidazole ·HCl] | 271-275 | 90 |
| MV1509 | [structure: 2-(4-acetamidophenyl)-4-methyl-5-phenyl-1H-imidazole ·HCl] | 276-279 (dec) | 90 |

| COMP. | STRUCTURE | CHEMICAL NAME | FORMULA MW |
|---|---|---|---|
| MV1501 | [structure] ·HCl | 2-(4-methoxyphenyl)-4-methyl-5-phenyl-1H-imidazole hydrochloride | C17H16N2O *HCl MW = 254.33 |
| MV1502 Example 4 | [structure] ·HCl | 2-(4-chlorophenyl)-4-methyl-5-phenyl-1H-imidazole hydrochloride | C16H13N2Cl *HCl MW = 268.74 |

TABLE 1-continued

Table of Compounds

| | | | |
|---|---|---|---|
| MV1503 | 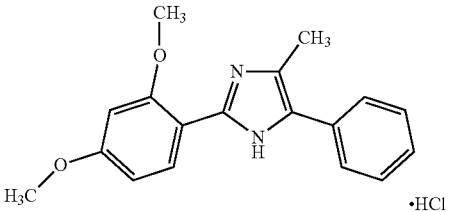 [SMILES: COc1ccc(-c2nc(C)c(-c3ccccc3)[nH]2)c(OC)c1 ; Cl] •HCl | 2-(2,4-dimethoxyphenyl)-4-methyl-5-phenyl-1H-imidazole hydrochloride | C18H18N2O2 *HCl MW = 294.35 |
| MV1504 | 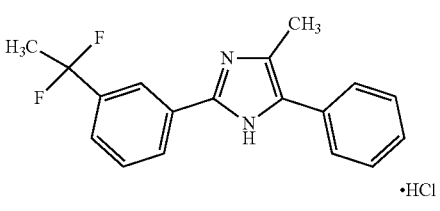 [SMILES: Cc1nc(-c2cccc(C(C)(F)F)c2)[nH]c1-c1ccccc1 ; Cl] •HCl | 4-methyl-5-phenyl-2-[3-(trifluoromethyl)phenyl]-1H-imidazole hydrochloride | C17H13F3N2 *HCl MW = 302.30 |
| MV1505 Example 5 | 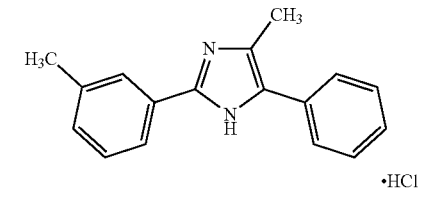 [SMILES: Cc1cccc(-c2nc(C)c(-c3ccccc3)[nH]2)c1 ; Cl] •HCl | 2-(3-chlorophenyl)-4-methyl-5-phenyl-1H-imidazole hydrochloride | C16H13N2Cl *HCl MW = 268.74 |
| MV1506 | 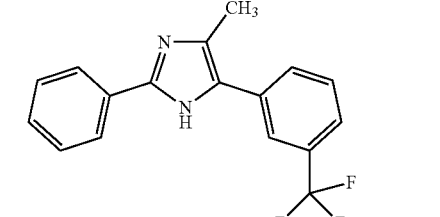 •HCl | 4-methyl-2-phenyl-5-[3-(trifluoromethyl)phenyl]-1H-imidazole hydrochloride | C17H13F3N2 *HCl MW = 302.30 |
| MV1507 | 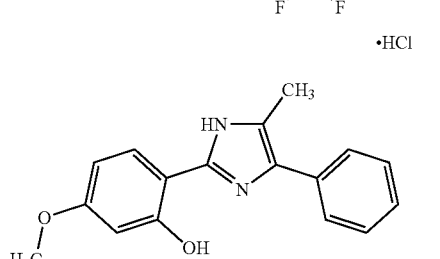 •HCl | 5-methoxy-2-(5-methyl-4-phenyl-1H-imidazol-2-yl)phenol hydrochloride | C17H16N2O2 *HCl MW = 280.33 |
| MV1508 | 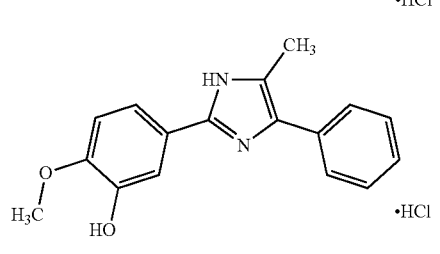 •HCl | 2-methoxy-5-(5-methyl-4-phenyl-1H-imidazol-2-yl)phenol hydrochloride | C17H16N2O2 *HCl MW = 280.33 |
| MV1509 | 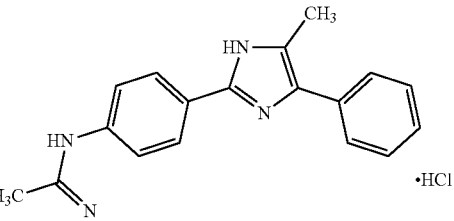 •HCl | N-(4-(5-methyl-4-phenyl-1H-imidazol-2-yl)phenyl]-acetamide hydrochloride | C18H17N3O *HCl MW = 291.35 |

TABLE 2

IC$_{50}$ Values of MV1060-MV1091

| Compound | IC$_{50}$ |
|---|---|
| MV1060 | >100 |
| MV1061 | |
| MV1062 | 90.18 |
| MV1066 | 34.63 |
| MV1068 | 41.61 |
| MV1069 | 37.00 |
| MV1070 | >100 |
| MV1071 | >100 |
| MV1072 | >100 |
| MV1073 | >100 |
| MV1074 | >100 |
| MV1075 | >100 |
| MV1076 | |
| MV1077 | >100 |
| MV1078 | >100 |
| MV1079 | >100 |
| MV1080 | >100 |
| MV1081 | >100 |
| MV1082 | |
| MV1083 | >100 |
| MV1084 | |
| MV1085 | >100 |

TABLE 2-continued

IC$_{50}$ Values of MV1060-MV1091

| Compound | IC$_{50}$ |
|---|---|
| MV1086 | 24.69 |
| MV1087 | >100 |
| MV1088 | |
| MV1089 | 40.09 |
| MV1090 | 29.6 |
| MV1091 | >100 |

Example 12

Evaluation of dose response and activation response compounds on rat NaV1.6 channels in Human Embryonic Kidney cells (HEK293).

Figure 2:
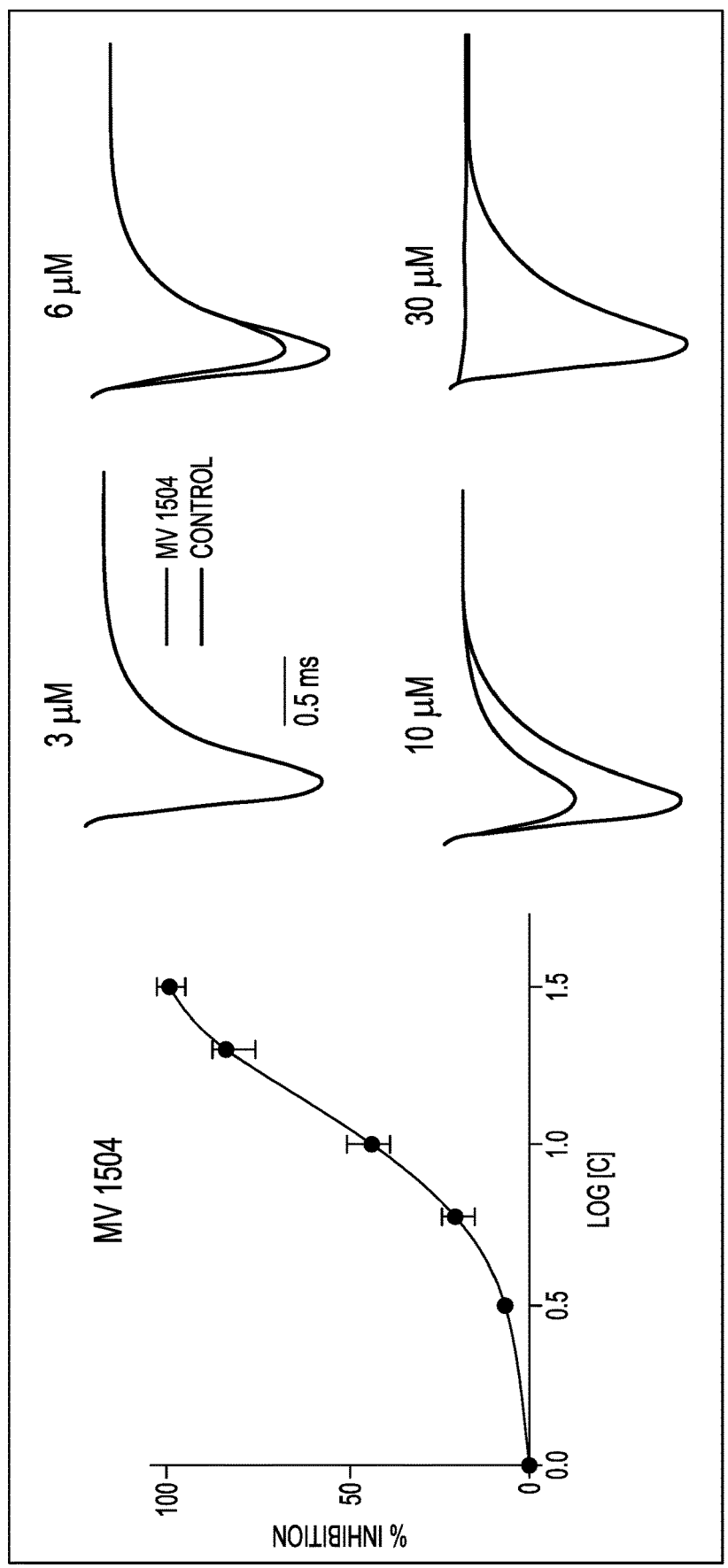
FIG. 2 shows a dose response curve for MV1504 and activation over time curves for MV1504 (light color line, top) compared to a control (dark color line, bottom) at 3 µM, 6 µM, 10 µM and 30 µM.
Figure 3:
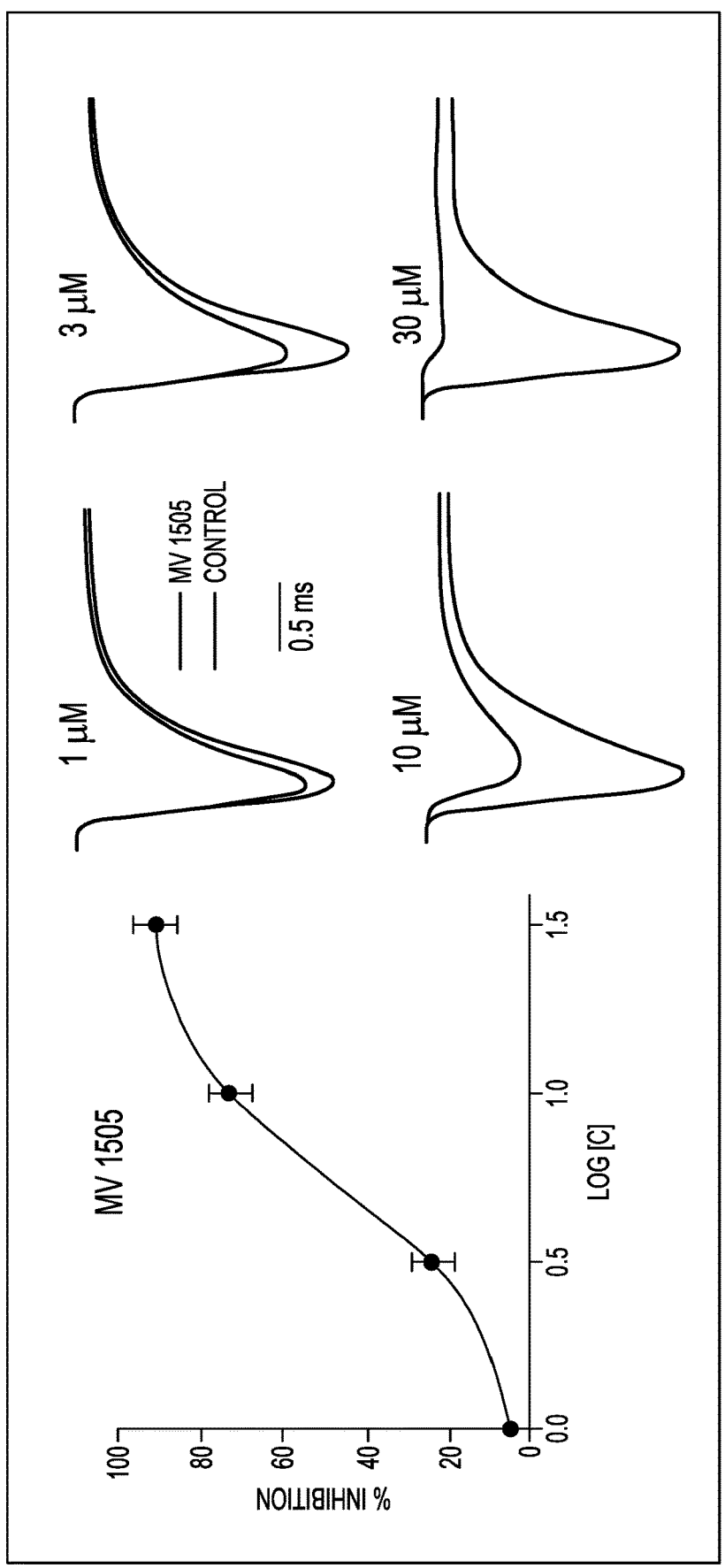
FIG. 3 shows a dose response curve for MV1505 and activation over time curves for MV1505 (light color line, top) compared to a control (dark color line, bottom) at 1 µM, 3 µM, 10 µM and 30 µM.

Compounds of the present invention were tested on rat NaV1.6 sodium channels in human embryonic kidney cells (HEK293) to determine IC50 values at Table 3 and dose response curves as shown in FIG. 1, FIG. 2 and FIG. 3. FIG. 1 shows a plot showing dose response of MV1502 and activation over time curves for MV1502 (light color line, top) compared to a wash (medium color line, middle) and a control (dark color line, bottom) at 500 nM, 1 µM and 10 µM. FIG. 2 shows a dose response curve for MV1504 and activation over time curves for MV1504 (light color line, top) compared to a control (dark color line, bottom) at 3 µM, 6 µM, 10 µM and 30 µM. FIG. 3 shows a dose response curve for MV1505 and activation over time curves for MV1505 (light color line, top) compared to a control (dark color line, bottom) at 1 µM, 3 µM, 10 µM and 30 µM.

TABLE 3

Rat Nav1.6 channel IC50 values for MV1502, MV1504 and MV1505

| Compound | | IC$_{50}$ |
|---|---|---|
| MV1502 | 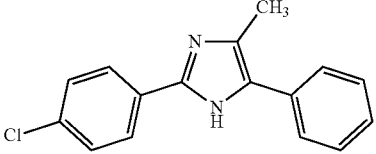 [SMILES: Cc1nc(-c2ccc(Cl)cc2)[nH]c1-c1ccccc1] | 1.2 µM |
| MV1504 | 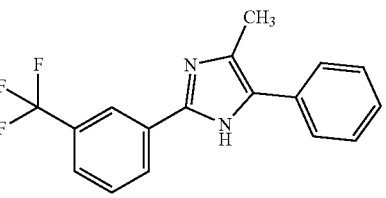 | 12 µM |
| MV1505 | 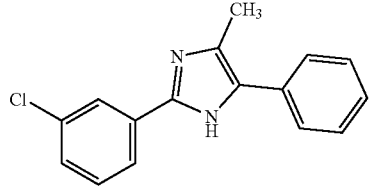 [SMILES: Cc1nc(-c2cccc(Cl)c2)[nH]c1-c1ccccc1] | 5.4 µM |

Example 13

Evaluation of compounds as state-dependent inhibitors

Figure 4:
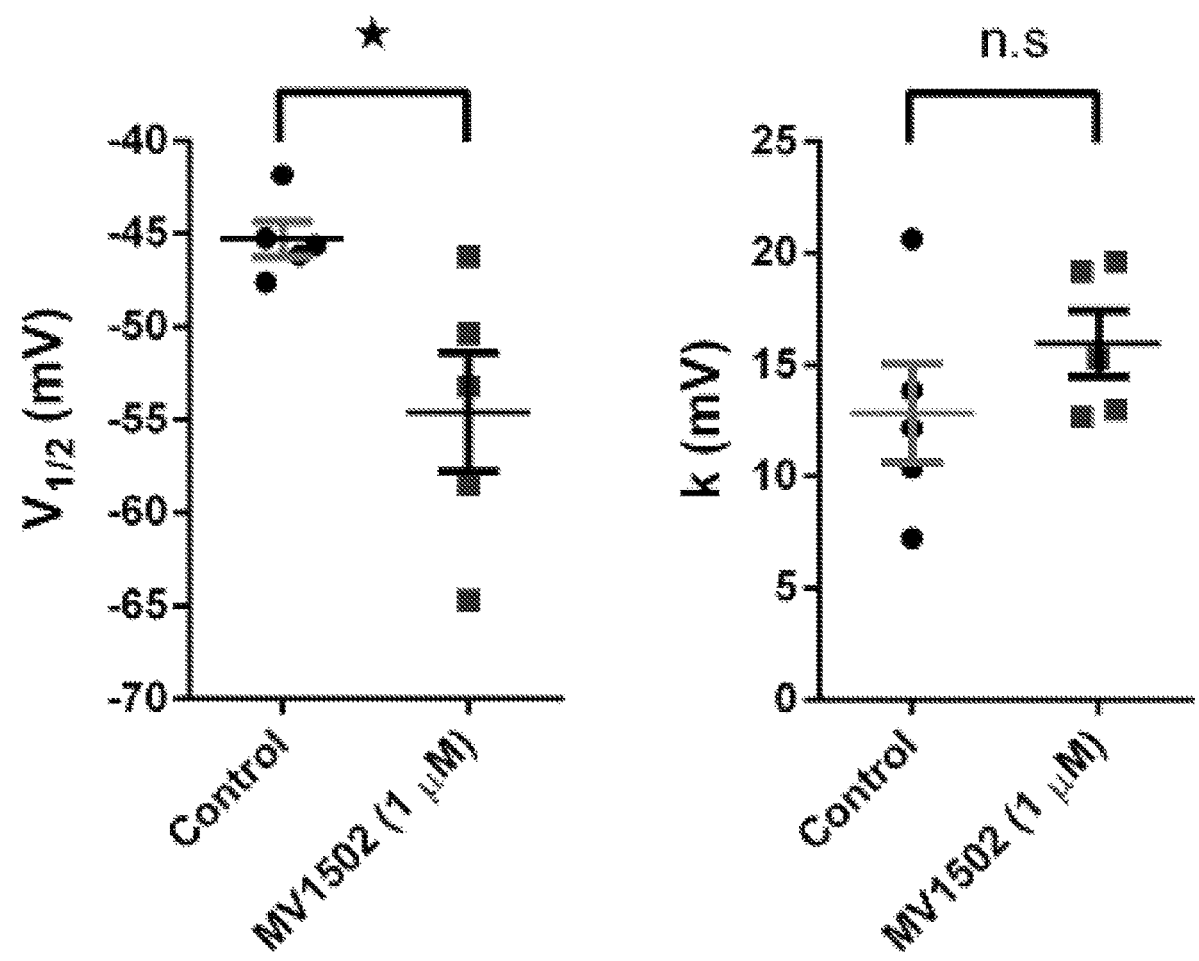
FIG. 4 shows MV1502 (light squares) at 1 µM at half maximal voltage for inactivation ($V_{1/2}$) which was shifted by −9.3 mV compared to a control (dark squares).
Figure 5:
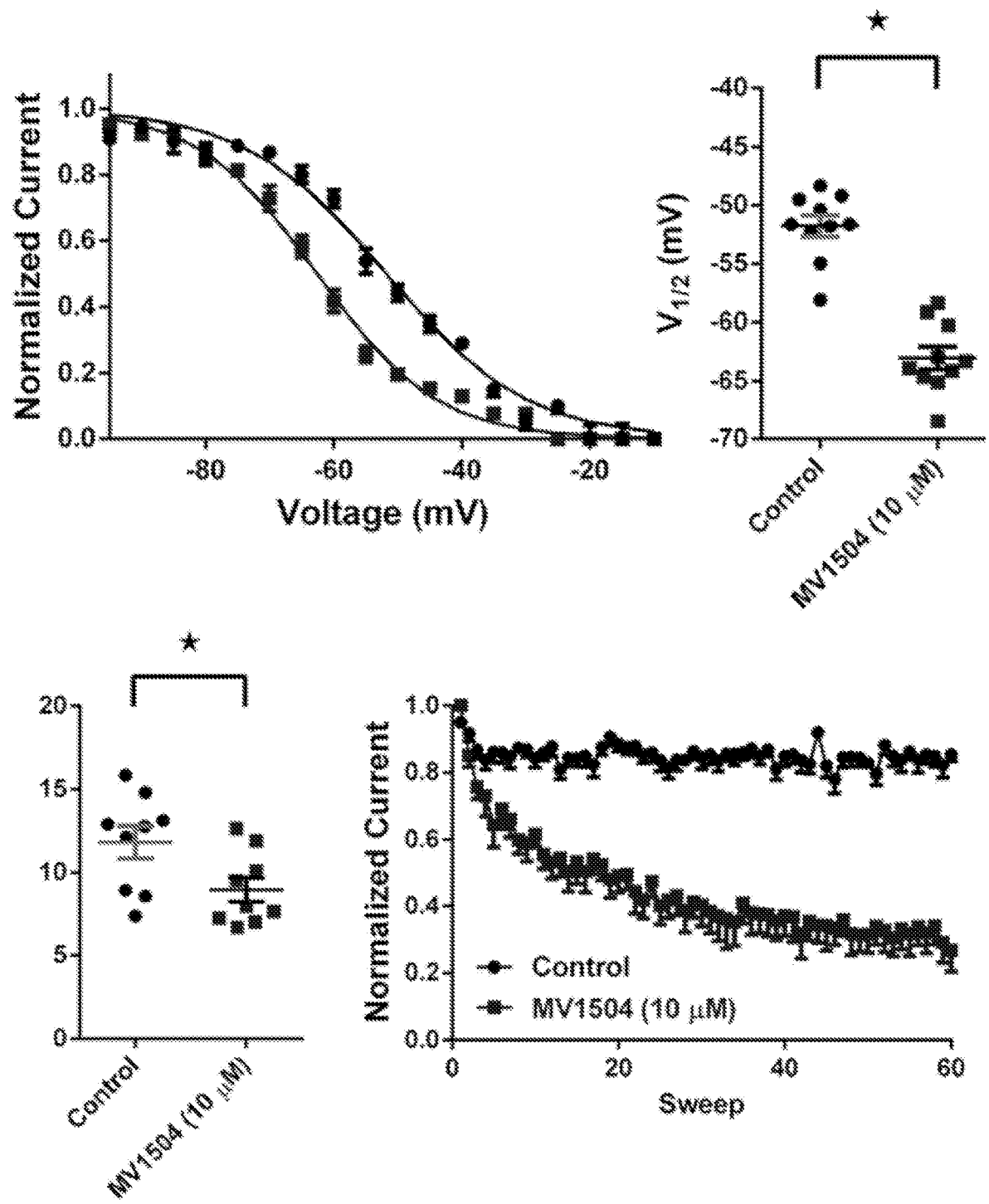
FIG. 5 shows MV1504 (light squares) at 10 µM at half maximal voltage for inactivation ($V_{1/2}$) which was shifted by −10.9 mV compared to a control (dark squares); shows a steady state inactivation curve comparing MV1504 (light squares) with a control (dark squares) plotted against normalized current and voltage; and also shows a use-dependent block at 20 Hz with MV1504 (light squares) in comparison to a control (dark squares).
Figure 6:
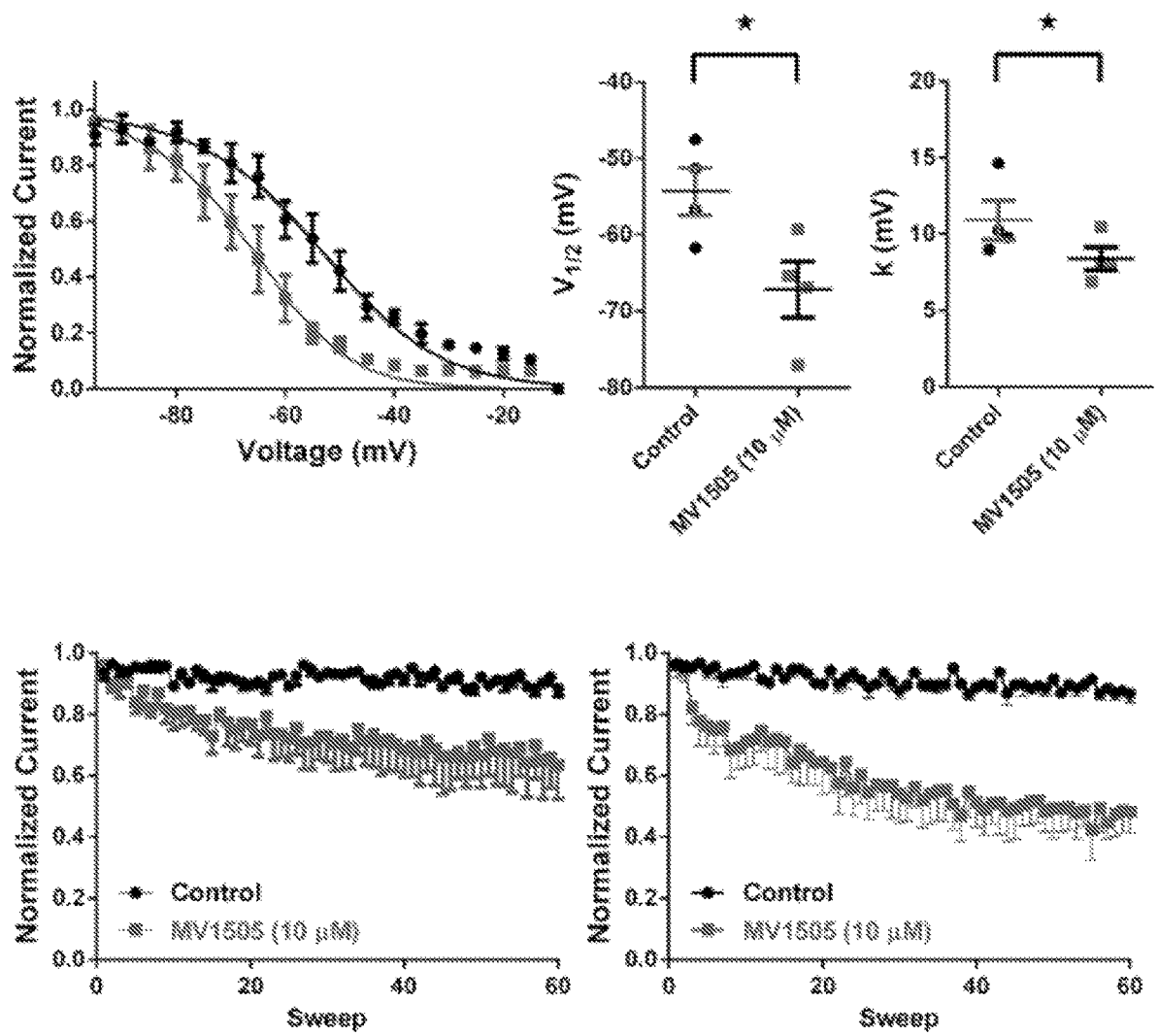
FIG. 6 shows MV1505 (light squares) at 10 µM at half maximal voltage for inactivation ($V_{1/2}$) which was shifted by −12.7 mV compared to a control (dark squares); shows a steady state inactivation curve comparing MV1505 (light squares) with a control (dark squares) plotted against normalized current and voltage; and also shows a use-dependent block at 20 Hz with MV1505 (light squares) in comparison to a control (dark squares).
Figure 7:
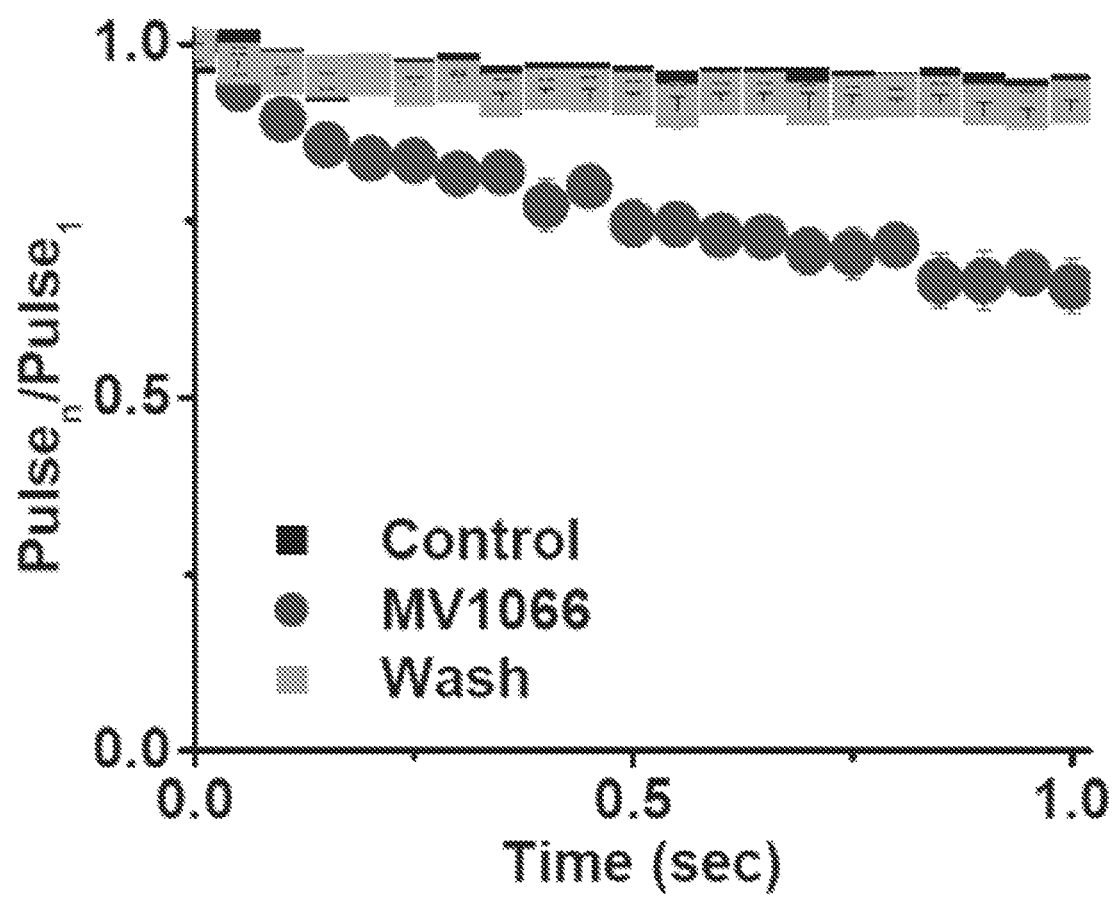
FIG. 7 shows a use-dependent block at 20 Hz with MV1066 (circles) in comparison to a control (dark squares) and wash (light squares). These compound exhibit profound use-dependent block. Use dependent block is an important characteristic for AED activity since it allows increased inhibition of sodium channels during increased neuronal activity as is observed during seizures.
Figure 8:
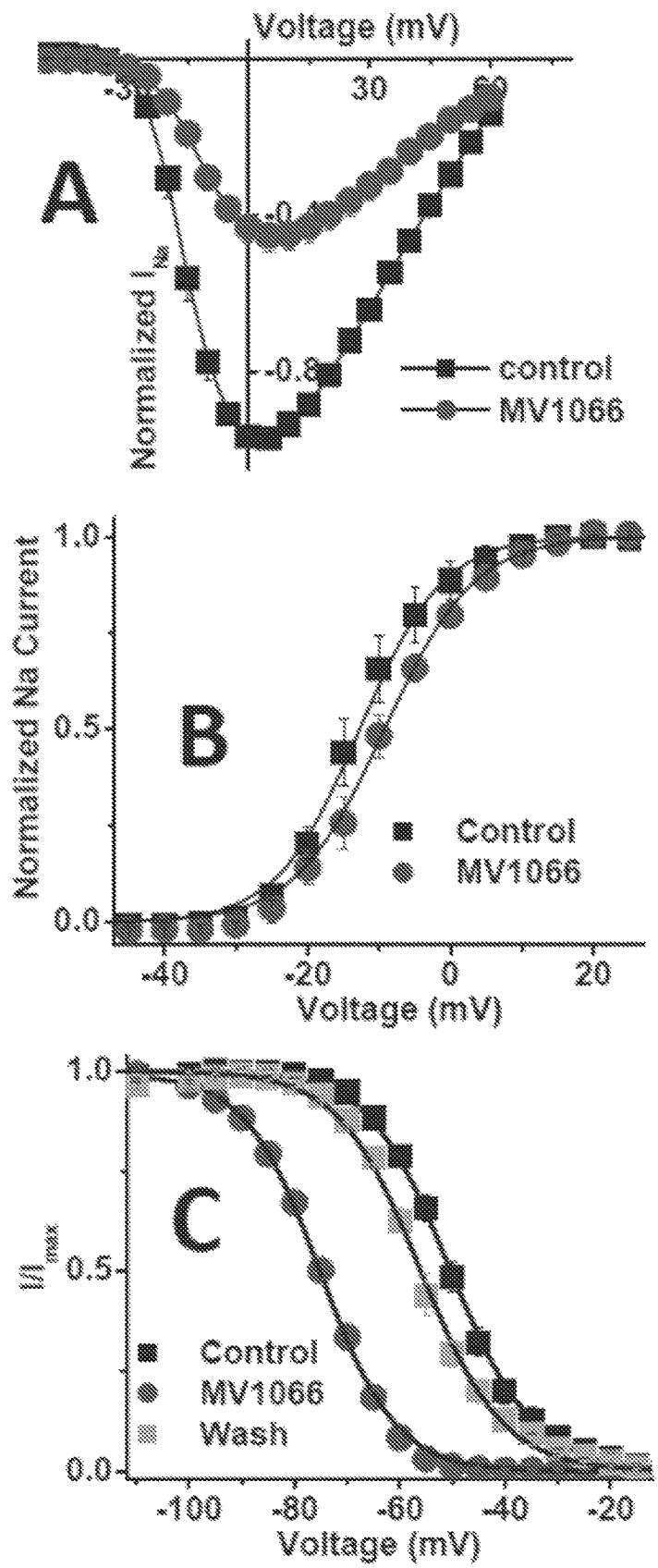
FIG. 8 shows (A) current/voltage relationship, (B) conductance and (C) steady state inactivation curve using 1 second pre-pulse of 100 µM MV1066 (circles) compared to a control (dark squares) and wash (light squares). The results shown demonstrate that the compound inhibits macroscopic current amplitude but has no effect on activation gating.
Figure 9:
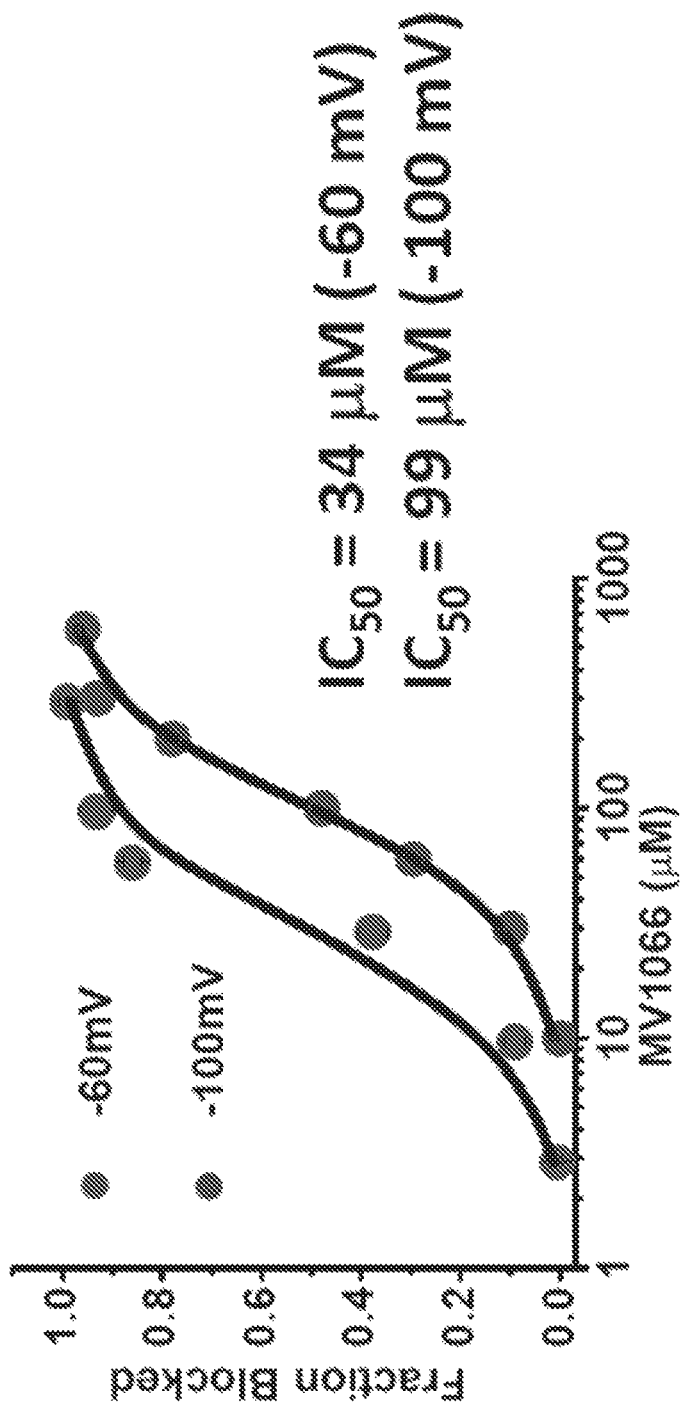
FIG. 9 shows a dose response curve for MV1066 in cells held at either −100 mV (light circles, bottom) or −60 mV (dark circles, top) and then stepped to +10 mV to elicit sodium channel currents. The compound had a greater affinity for cells held at −60 mV.

Compounds were tested on NaV1.6 sodium channels and showed an affinity for the inactivated state of the sodium channel. The compounds exhibited a steady state inactivation curve and use-dependent blocking. FIG. 4 shows MV1502 (light squares) at 1 µM at half maximal voltage for inactivation (V$_{1/2}$) which was shifted by −9.3 mV compared to a control (dark squares). FIG. 5 shows MV1504 (light squares) at 10 µM at half maximal voltage for inactivation (V$_{1/2}$) which was shifted by −10.9 mV compared to a control (dark squares); shows a steady state inactivation curve comparing MV1504 (light squares) with a control (dark squares) plotted against normalized current and voltage; and also shows a use-dependent block at 20 Hz with MV1504 (light squares) in comparison to a control (dark squares). FIG. 6 shows MV1505 (light squares) at 10 μM at half maximal voltage for inactivation ($V_{1/2}$) which was shifted by −12.7 mV compared to a control (dark squares); shows a steady state inactivation curve comparing MV1505 (light squares) with a control (dark squares) plotted against normalized current and voltage; and also shows a use-dependent block at 20 Hz with MV1505 (light squares) in comparison to a control (dark squares). FIG. 7 shows a use-dependent block at 20 Hz with MV1066 (circles) in comparison to a control (dark squares) and wash (light squares). These compound exhibit profound use-dependent block. Use dependent block is an important characteristic for AED activity since it allows increased inhibition of sodium channels during increased neuronal activity as is observed during seizures. FIG. 8 shows (A) current/voltage relationship, (B) conductance and (C) steady state inactivation curve using 1 second pre-pulse of 100 μM MV1066 (circles) compared to a control (dark squares) and wash (light squares). The results shown demonstrate that the compound inhibits macroscopic current amplitude but has no effect on activation gating. FIG. 9 shows a dose response curve for MV1066 in cells held at either −100 mV (light circles, bottom) or −60 mV (dark circles, top) and then stepped to +10 mV to elicit sodium channel currents. The compound had a greater affinity for cells held at −60 mV. The results in FIG. 8 and FIG. 9 suggest that MV1066 has a greater affinity for the inactivated state of the channel, which is a advantageous property that is found in clinically active compounds.

Example 14

Evaluation of compounds on human isoforms using a high-throughput flux assay.

Compounds were tested using a high-throughput flux assay across Nav1.5, Nav1.6 and Nav1.7. Flux $IC_{50}$ results are presented in Table 4.

TABLE 4

| | FLUX $IC_{50}$ | | | |
|---|---|---|---|---|
| Compound | | Nav1.6 | NaV1.5 | NaV1.7 |
| MV1501 | 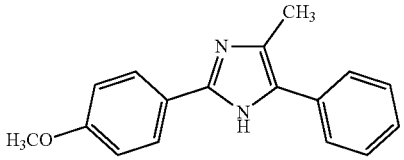 [SMILES: COc1ccc(-c2nc(C)c(-c3ccccc3)[nH]2)cc1] | 2.738 | 6.241 | 7.984 |
| MV1502 | 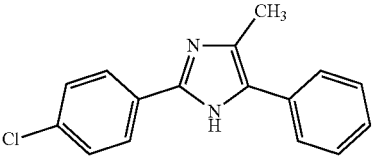 [SMILES: Cc1nc(-c2ccc(Cl)cc2)[nH]c1-c1ccccc1] | 1.612 | 4.887 | 4.756 |
| MV1504 | 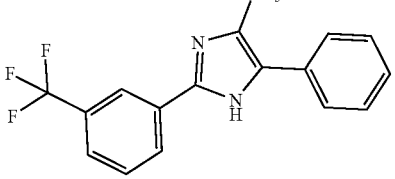 | 2.073 | 4.324 | 5.717 |
| MV1505 | 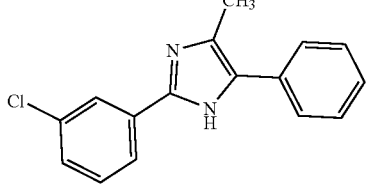 | 1.59 | 3.64 | 5.224 |
| MV1508 | 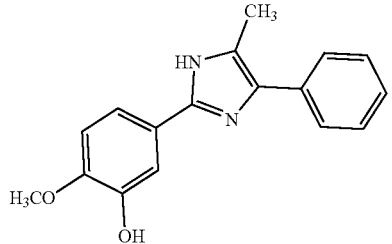 [SMILES: COc1ccc(-c2nc(-c3ccccc3)c(C)[nH]2)cc1O] | 1.884 | 2.611 | 4.58 |

TABLE 4-continued

| FLUX IC$_{50}$ | | | | |
|---|---|---|---|---|
| Compound | | Nav1.6 | NaV1.5 | NaV1.7 |
| MV1509 | [structure: 2-(4-acetamidophenyl)-4-methyl-5-phenyl-1H-imidazole] | 5.673 | 7.944 | 23.82 |

Example 15

Evaluation of compounds on human isoforms using Qube assay.

Compounds were tested using a Qube assay across NaV1.5, NaV1.6 and NaV1.7. Qube IP IC$_{50}$ results are presented in Table 5.

TABLE 5

| Qube EP IC$_{50}$ | | | | |
|---|---|---|---|---|
| Compound | | NaV1.6 | NaV1.5 | NaV1.7 |
| MV1501 | [structure: 2-(4-methoxyphenyl)-4-methyl-5-phenyl-1H-imidazole] | 7.434 | 27.02 | 14.8 |
| MV1502 | [structure: 2-(4-chlorophenyl)-4-methyl-5-phenyl-1H-imidazole] | 0.7494 | 12.66 | 3.884 |
| MV1504 | [structure: 4-methyl-5-phenyl-2-(3-(trifluoromethyl)phenyl)-1H-imidazole] | 3.321 | 13.26 | 7.951 |
| MV1505 | [structure: 2-(3-chlorophenyl)-4-methyl-5-phenyl-1H-imidazole] | 2.724 | 10 | 8.044 |

TABLE 5-continued

| | Qube EP IC$_{50}$ | | |
|---|---|---|---|
| Compound | NaV1.6 | NaV1.5 | NaV1.7 |
| MV1508 (structure: imidazole with CH$_3$, phenyl, and H$_3$CO/OH substituted phenyl, HN) | 3.987 | 11.86 | 11.55 |
| MV1509 (structure: imidazole with CH$_3$, phenyl, and acetamido-phenyl, HN) | 8.243 | 15.89 | 30 |

Example 16

In vivo evaluation for seizure suppression in a human gain of function NaV1.6 mutation knock-in mouse model.

Figure 10:
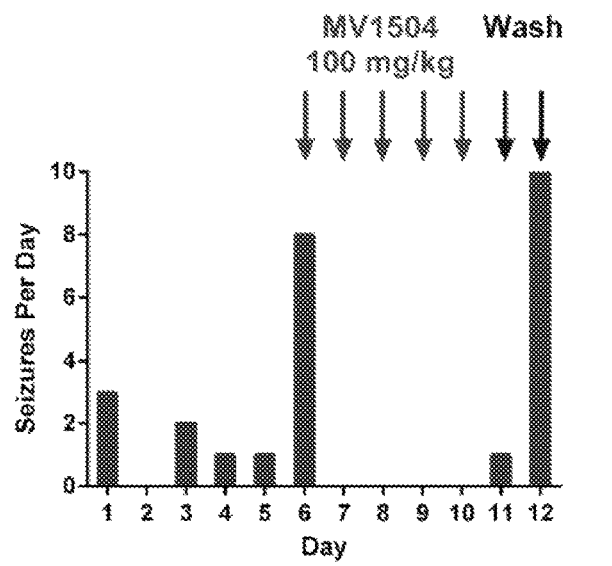
FIG. 10 shows administration of each of MV1502, MV1504 and MV1505 to mice suffering from spontaneous seizures (knock-in mouse model, carrying human N1768D NaV1.6 mutation), and shows that administration of these compounds treats the seizures.
Figure 10:
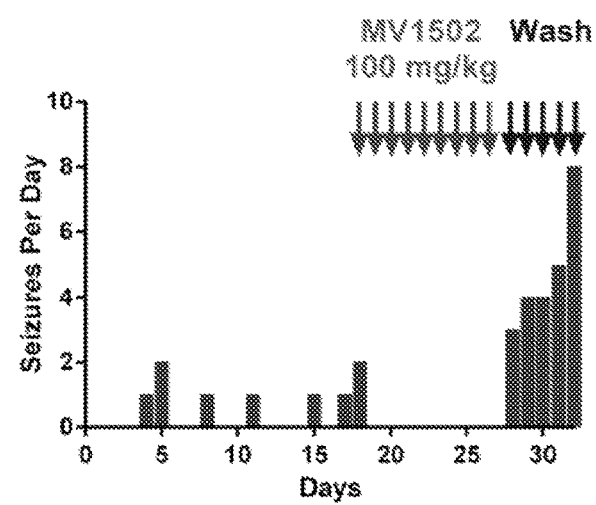
Figure 10:
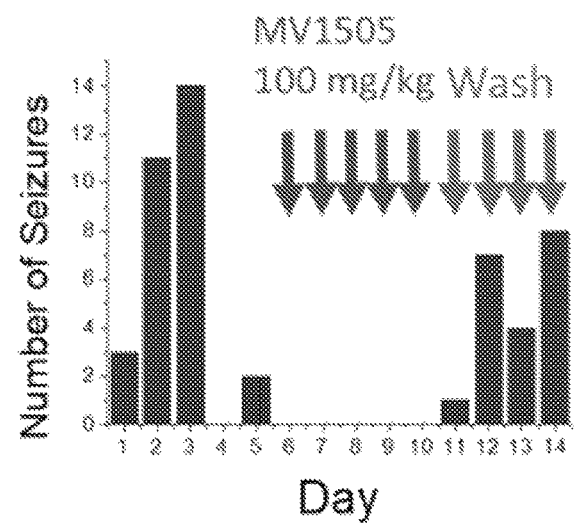

Compounds were tested in vivo for seizure suppression in a knock-in mouse carrying the human N1768D gain of function NaV1.6 mutation. These knock-in mice experience spontaneous seizures. All test compounds were evaluated at 100 mg/kg. MV1502 (n=2 mice), MV1504 (n=4 mice) and MV1505 (n=6 mice) each suppressed seizures in the knock-in mice upon administration at 100 mg/kg. FIG. 10 shows administration of each of MV1502, MV1504 and MV1505 to mice suffering from spontaneous seizures (knock-in mouse model, carrying human N1768D NaV1.6 mutation), and shows that administration of these compounds treats the seizures.

Example 17

Evaluation of effects on NaV1.6 sodium channel recovery from inactivation.

Figure 11:
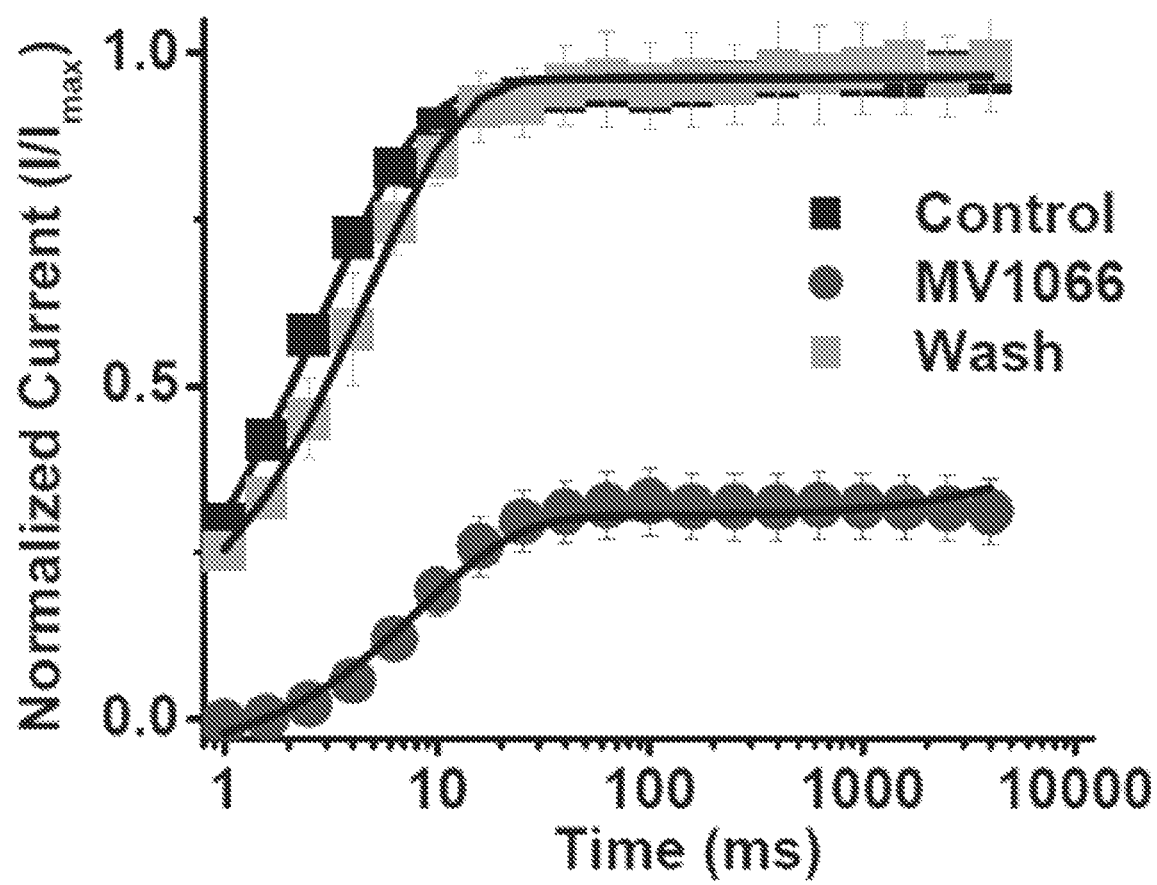
FIG. 11 shows MV1066 (circles) vs control (dark squares) and wash (light squares) plotted against normalized current ($I/I_{max}$) and time (ms).

Compounds were tested for their effects on recovery from inactivation parameters using a 1 second inactivation pre-pulse. MV1066 (100 µM) profoundly delays recovery from inactivation. This characteristic would reduce the number of sodium channels available for action potential initiation and conduction. Many clinically active compounds delay recovery from inactivation. FIG. 11 shows MV1066 (circles) vs control (dark squares) and wash (light squares) plotted against normalized current (I/I$_{max}$) and time (ms).

Example 18

Evaluation of compounds in MES models of seizures.

The MES is a model for generalized tonic-clonic seizures and provides an indication of a compound's ability to prevent seizure spread when all neuronal circuits in the brain are maximally active. These seizures are highly reproducible and are electrophysiologically consistent with human seizures. For an MES test, a drop of anesthetic/electrolyte solution (0.5% tetracaine hydrochloride in 0.9% saline) is applied to the eyes of each animal prior to placement of corneal electrodes. Electrical stimulus in the MES test may be 50 mA, 60 Hz, for mice and 150 mA, 60 Hz, for rats delivered for 0.2 s. Abolition of the hindleg tonic extensor component of the seizure was used as the endpoint. Mice may be initially tested at various intervals following various doses, e.g., 30, 100 and 300 mg/kg of test compound given by intraperitoneal (IP) injection while rats are initially screened at a fixed dose of 30 mg/kg Compounds were tested using a maximal electroshock (MES) model which represents acute animal seizures. The MES test is predictive of compounds with efficacy in the management of generalized tonic-clonic seizures and partial epilepsy. The MES is clinically validated as a preclinical animal model of human generalized seizures as evidenced by the clinical success of phenytoin. Results of MV1066 in the MES test are shown in Table 6 (mice) and Table 7 (rats). ED$_{50}$ values from the MES tests are shown in Table 8. The MV1066 protective index (I.P.) was 8.67 in mice and 19.9 in rats. MV1062 was also evaluated by the MES test and showed an ED$_{50}$ value of 30.78 (mice) and 10.78 (rats), a TD$_{50}$ (behavioral toxic dose) value of 601.21 (mice) and >500 (rats), and a protective index of 19.5 (mice) and >46 (rats). For comparison purposes, an IC50 NaV1.6 value for MV1062 was determined (90.18). The MES test showed that MV1062 and MV1066 have advantageous protective index values compared to clinical AEDs phenytoin, lamotrigine, carbamazepine, valproic acid and ethosuximide. Tests of behavioral toxicity suggest that the compounds also have advantages in this regard over phenytoin, lamotrigine, and carbamazepine, and ethosuximide.

TABLE 6

Time to peak effect in mice via IP administration of 100 mg/kg of MV1066

| | | | | Time (Hours) | | | | | | | | |
|---|---|---|---|---|---|---|---|---|---|---|---|---|
| Test | Dose | Form | Deaths | 0.25 N/F | 0.5 N/F/ | 1.0 N/F | 2.0 N/F | 4.0 N/F | 6.0 N/F | 8.0 N/F | 24 N/F | 30 N/F |
| SMES | 100.0 | SUS | | 4/4 | 4/4 | 4/4 | 4/4 | 4/4 | / | / | / | / |
| TOX | 100.0 | | | 1/4 | 0/4 | 0/4 | 0/4 | 0/4 | / | / | / | / |

N/F = number of animals active or toxic over the number tested

TABLE 7

Time to peak effect in rats via IP administration of 30 mg/kg of MV1066

| | | | Time (Hours) | | | | | | | | |
|---|---|---|---|---|---|---|---|---|---|---|---|
| Test | Dose | Deaths | 0.25 N/F | 0.5 N/F | 1.0 N/F | 2.0 N/F | 4.0 N/F | 6.0 N/F | 8.0 N/F | 24 N/F | 30 N/F |
| MES | 30.0 | | 2/4 | 4/4 | 4/4 | 3/4 | 4/4 | / | / | / | / |
| TUX | 30.0 | | 0/4 | 0/4 | 0/4 | 0/4 | 0/4 | / | / | / | / |

N/F = number of animals active or toxic over the number tested

TABLE 8

$ED_{50}$ values from MES test.

| Compound | Animal | Time (Hrs) | $ED_{50}$ | 95% Conf. Int. | Slope | STD Err |
|---|---|---|---|---|---|---|
| MV1066 | Mouse | 0.5 | 44.24 | 33.03-56.74 | 5.68 | 1.73 |
| | Rat | 0.5 | 25.13 | 14.6-46.44 | 2.6 | 0.88 |

Example 19

Evaluation of compounds in scM models of seizures.

Subcutaneous injection of the convulsant Metrazol produces clonic seizures in laboratory animals. The scMET test detects the ability of a test compound to raise the seizure threshold of an animal and thus protect it from exhibiting a clonic seizure. Animals may be pretreated with various doses of the test compound given by ip injection. At a previously determined TPE (time to peak) of the test compound, the dose of Metrazol which will induce convulsions in 97% of animals (CD97: 85 mg/kg mice) may be injected into a loose fold of skin in the midline of the neck. The animals may be placed in isolation cages to minimize stress and observed for the next 30 min for the presence or absence of a seizure. An episode of clonic spasms, approximately 3-5 seconds, of the fore and/or hindlimbs, jaws, or vibrissae may be taken as the endpoint. Animals which do not meet this criterion can be considered protected. The scM test represents acute animal seizures. The scM test, also known as the subcutaneous pentylentetrazol (scPTZ) test, is predictive of compounds with efficacy in the management of generalized absence epilepsy. This method is clinically validated since drugs active against spike-wave seizures blocked clonic seizures induced by scM, while drugs ineffective against spike-wave seizures were inactive in the scM test. $ED_{50}$ values from the scM tests are shown in Table 9. MV1062 was also evaluated by the scM test and showed an $ED_{50}$ value of 206.1 (mice) and 122.84 (rats), a $TD_{50}$ value of 601.21 (mice) and >500 (rats), and a protective index of 2.9 (mice) and >4 (rats). The scM test showed that MV1062 and MV1066 have advantageous protective index values compared to clinical AEDs phenytoin, lamotrigine, carbamazepine, and ethosuximide.

TABLE 9

$ED_{50}$ values from scM tests.

| Compound | Animal | Time (Hrs) | $ED_{50}$ | 95% Conf. Int. | Slope | STD Err |
|---|---|---|---|---|---|---|
| MV1066 | Mouse | 0.5 | 180.64 | 141.61-225.64 | 5.44 | 1.54 |
| | Rat | 0.5 | 96.96 | 59-141.39 | 2.93 | 0.76 |

Example 20

Evaluation of compounds in 6 Hz pyschomotor seizure test

Compounds were tested using a 6 Hz psychomotor seizure test. The resistance of some subjects to phenytoin and other traditional AEDs support the need to include additional tests in AED screening paradigms to detect novel AEDs. For example, both the MES and scM models are insensitive to levetiracetam, a compound considered potentially useful in the management of refractory seizures. In contrast, the 6 Hz seizure psychomotor seizure test has demonstrated levetiracetam-sensitivity and thus may offer some advantage of the MES and scM tests in the earlier identification of compounds with potential efficacy for therapy resistant epilepsy. The pharmacological profile demonstrated by the 6 Hz model differentiates itself from other acute seizure models because its ability to discriminates AEDs increases proportionally with the stimulus intensity, e.g., 22 mA, 32 mA and 44 mA, delivered. Thus, the 6 Hz test can serve as a therapy resistant screening paradigm of acute seizure activity. Results of the 6 Hz test in mice at 32 mA are shown in Table 10 and results at 44 mA are shown in Table 11. The 6 Hz test at 32 mA for MV1066 showed an $ED_{50}$ value of 67.11 (mice), a 95% confidence interval of 52.04-85.03, a slope of 5.45 and standard error of 1.45. It is noted that whereas at 22 mA several clinical AEDs may work, the 32 mA and 44 mA tests are more selective. For example, phenytoin and lamotrigine lose activity when subject to the 32 mA test. At 44 mA, ethosuximide is ineffective and levetiracetam and valproate need higher doses. The 6 Hz tests at 32 mA and 44 mA showed that MV1062 and MV1066 have advantageous protective index values compared to clinical AEDs phenytoin, lamotrigine, carbamazepine, valproic acid and ethosuximide.

TABLE 10

Time to peak effect in mice via IP administration of 100 mg/kg of MV1066 for 6 Hz stimulation at 32 mA.

| | | | Time (Hours) | | | | | | | |
|---|---|---|---|---|---|---|---|---|---|---|
| Test | Dose | Deaths | 0.25 N/F | 0.5 N/F | 1.0 N/F | 2.0 N/F | 4.0 N/F | 6.0 N/F | 8.0 N/F | 24 N/F | 30 N/F |
| 6 Hz | 100.0 | | 4/4 | 4/4 | 3/4 | 2/4 | 0/4 | / | / | / | / |
| TOX | 100.0 | | 0/4 | 0/4 | 0/4 | 0/4 | 0/4 | / | / | / | / |

N/F = number of animals active or toxic over the number tested

TABLE 11

Time to peak effect in mice via IP administration of 100 mg/kg of MV1066 for 6 Hz stimulation at 44 mA.

| | | | Time (Hours) | | | | | | | |
|---|---|---|---|---|---|---|---|---|---|---|
| Test | Dose | Deaths | 0.25 N/F | 0.5 N/F | 1.0 N/F | 2.0 N/F | 4.0 N/F | 6.0 N/F | 8.0 N/F | 24 N/F | 30 N/F |
| 6 Hz | 100.0 | | 2/4 | 2/4 | 2/4 | 0/4 | 0/4 | / | / | / | / |
| TOX | 100.0 | | 0/4 | 0/4 | 0/4 | 0/4 | 0/4 | / | / | / | / |

N/F = number of animals active or toxic over the number tested

Example 21

Evaluation of compounds in Corneal Kindled Mice model.

Corneal kindled mice are kindled electrically via 3 second stimulation at 8 mA, 60 Hz through corneal electrodes to produce 10 consecutive stage 6 seizures according to the Racine scale. Animals are defined as kindled once they progress to a reproducible stage 5 seizure. 72 hours after the mice have been kindled the test substance is administered and, according to a previously determined TPE (time to peak), the animals are electrically stimulated. The animals are considered protected when displaying a stage 3, or lower, seizure. Table 12 shows results for MV1062 tested in the Corneal Kindled Mice model across three dosages. The test shoed an $ED_{50}$ of 63.6 mg/kg and a protective index of 9.5. Table 13 shows results for MV1066 tested in the Corneal Kindled Mice model across four dosages. The test shoed an $ED_{50}$ of 64.1 mg/kg and a protective index of 6.0.

TABLE 12

Results for MV1062 in the Corneal Kindled Mice model.

| Dose (mg/kg) | TPE (hours) | N/F | Seizure Score | Avg. Score | TOX N/F |
|---|---|---|---|---|---|
| 20 | 0.5 | 0/8 | 5, 5, 5, 5, 5, 5, 5, 5 | 5.0 | / |
| 55 | 0.5 | 3/8 | 5, 3, 1, 5, 3, 5, 5, 5 | 4.0 | / |
| 100 | 0.5 | 7/8 | 5, 0, 3, 3, 0, 0, 0, 0 | 1.375 | / |

N/F = number of animals active or toxic over the number tested

TABLE 13

Results for MV1066 in the Corneal Kindled Mice model.

| Dose (mg/kg) | TPE (hours) | N/F | Seizure Score | Avg. Score | TOX N/F |
|---|---|---|---|---|---|
| 35 | 0.5 | 1/8 | 3, 5, 5, 5, 5, 5, 5, 5 | 4.75 | / |
| 72 | 0.5 | 5/8 | 2, 3, 5, 5, 5, 2, 0, 3 | 3.125 | / |

TABLE 13-continued

Results for MV1066 in the Corneal Kindled Mice model.

| Dose (mg/kg) | TPE (hours) | N/F | Seizure Score | Avg. Score | TOX N/F |
|---|---|---|---|---|---|
| 90 | 0.5 | 5/8 | 4, 0, 3, 0, 5, 5, 2, 3 | 2.75 | / |
| 120 | 0.5 | 8/8 | 0, 0, 0, 0, 0, 3, 0, 0 | 0.375 | / |

N/F = number of animals active or toxic over the number tested

Example 22

Comparison of compound selectivity across sodium channel isoforms.

Voltage-gated sodium channels occur in various isoforms, including NaV1.1, NaV1.2, NaV1.3, NaV1.4, NaV1.5 NaV1.6 NaV1.7 and NaV1.8. Compounds herein may be selective, or specific, to certain sodium channel isoforms. Compounds may selective modulate NaV1.6.

Figure 13:
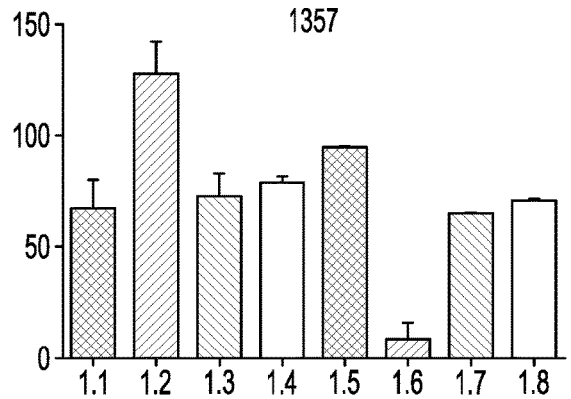
FIG. 13 shows selectivity of MV1357, MV1359, MV1362, MV1363, MV1365 and MV1366 for certain sodium channel isoforms.
Figure 13:
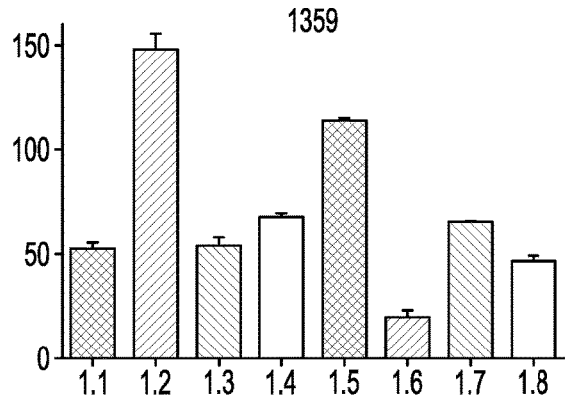
Figure 13:
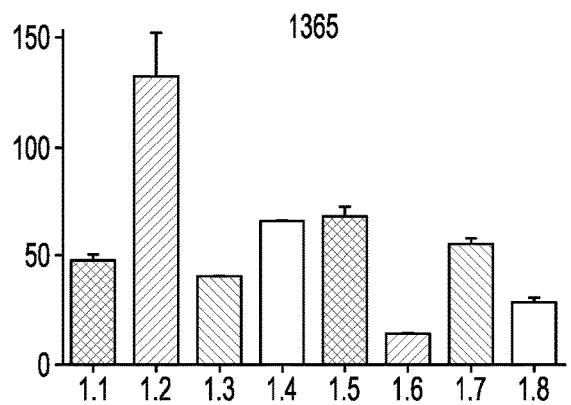
Figure 13:
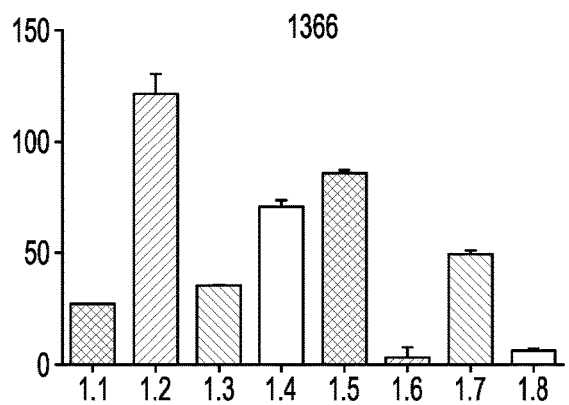
Figure 13:
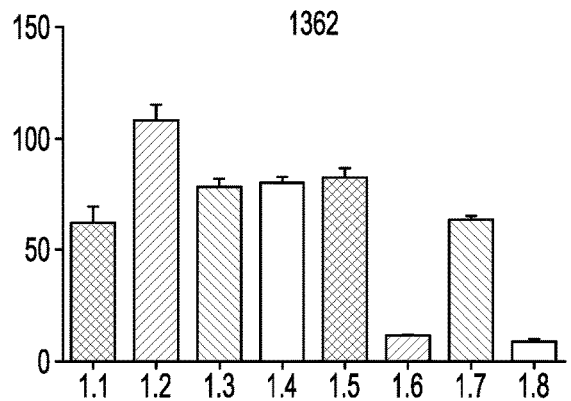
Figure 13:
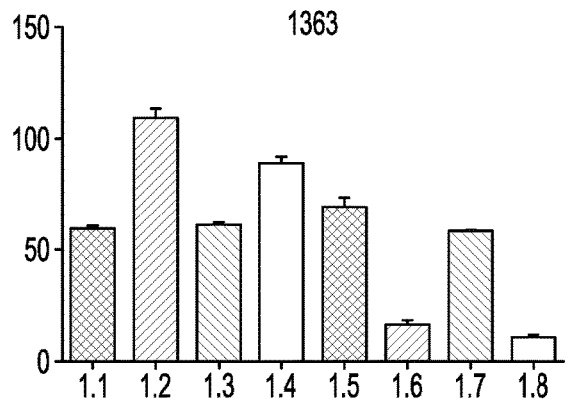
Figure 14:
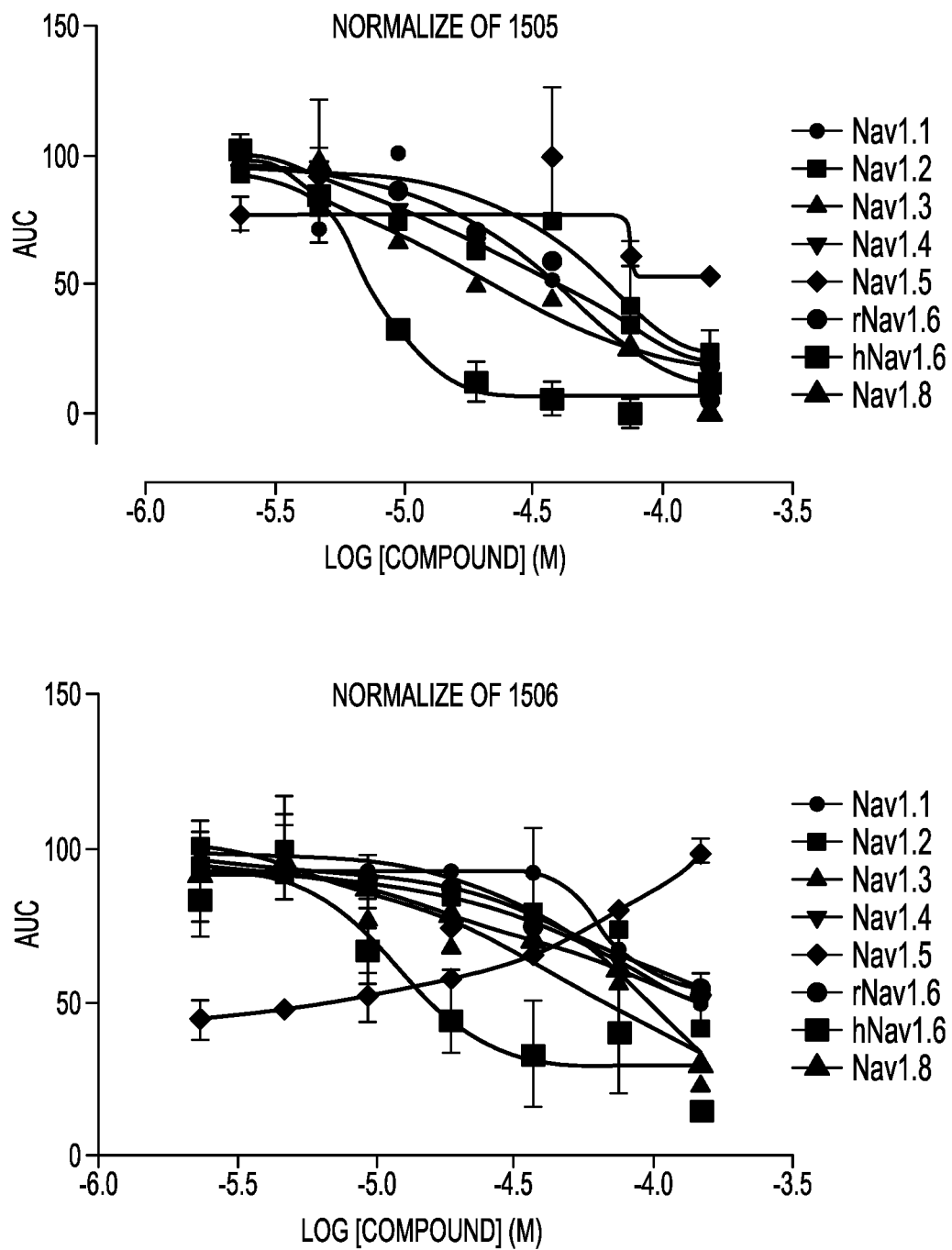
FIG. 14 shows selectivity of MV1505 and MV1506 for certain sodium channel isoforms the results plotting AUC vs compound concentration on a logarithmic scale.

Results show up-regulation of NaV1.2 and NaV1.6 isoforms, not only in rats with spontaneous seizures, but also after injury and before the onset of seizures. NaV1.6 is heavily expressed along the axon initial segment (AIS) and thus it is likely that this isoform plays a major role in facilitating neuronal excitability associated with epilepsy. Using shRNA to target NaV1.6 we have demonstrated that knockdown of Nav1.6 can increase after discharge thresholds in kindled rats. These studies support the targeting of Nav1.06 for therapy development. FIG. 13 shows selectivity of MV1357, MV1359, MV1362, MV1363, MV1365 and MV1366 for certain sodium channel isoforms. FIG. 14 shows selectivity of MV1505 and MV1506 for certain sodium channel isoforms the results plotting AUC vs compound concentration on a logarithmic scale.

Example 23

In vivo evaluation of compounds compared to clinical AEDs.

Figure 12:
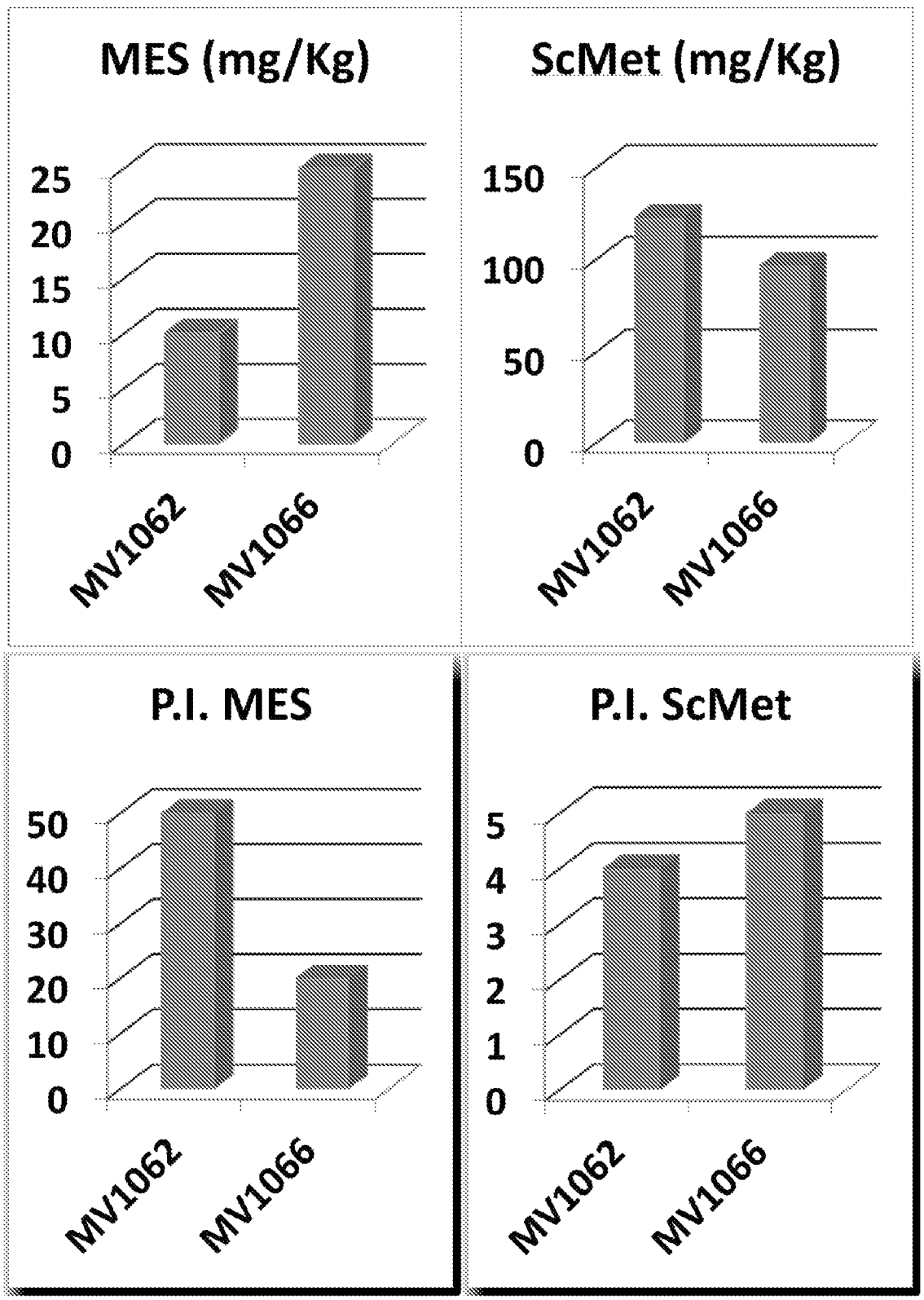
FIG. 12 shows in vivo data for MV1062 and MV1066 in rats with $ED_{50}$ and $TD_{50}$ values in mg/kg.

Compounds were compared to clinical AEDs by using IVIES, scM and 6 Hz tests in mice (via IP administration). Table 14 shows a comparison with $ED_{50}$ and $TD_{50}$ values in mg/kg and demonstrates advantages of compounds disclosed herein over phenytoin, lamotrigine, carbamazepine, valproic acid and ethosuximide. Table 15 and FIG. 12 shows additional in vivo data for MV1062 and MV1066 in rats with $ED_{50}$ and $TD_{50}$ values in mg/kg.

TABLE 14

Comparison of compound in vivo data in mice to clinical AEDs

|  | MES | | seM | | 6 Hz (32 mA) | | 6Hz (44 mA) | | TOX |
|---|---|---|---|---|---|---|---|---|---|
| Test | $ED_{50}$ | PI | $ED_{50}$ | PI | $ED_{50}$ | PI | $ED_{50}$ | PI | $TD_{50}$ |
| MV1062 | 30.8 | 19.5 | 206 | 2.9 | 69.6 | 8.6 | 80.5 | 7.5 | 601 |
| MV1066 | 44.2 | 8.7 | 180 | 2.1 | 67.1 | 5.7 | 72.4 | 5.3 | 383 |
| Phenytoin | 9.5 | 6.9 | None | n/a | None | n/a | None | n/a | 65.5 |
| Lamotrigine | 7.5 | 4.0 | None | n/a | None | n/a | None | n/a | 30.0 |
| Carbamazepine | 7.8 | 5.8 | None | n/a | None | n/a | None | n/a | 45.5 |
| Valproic Acid | 263 | 1.5 | 220 | 1.8 | 126 | 3.2 | 310 | 1.3 | 398 |
| Ethosuximide | None | n/a | 136 | 2.5 | 167 | 2.0 | None | n/a | 341 |

TABLE 15

Additional in vivo data from MES and scM tests in rats (via IP administration).

|  | MES | | scM | | TOX |
|---|---|---|---|---|---|
| Test | $ED_{50}$ | PI | $ED_{50}$ | PI | $TD_{50}$ |
| MV1062 | 10.8 | >46 | 122 | >4 | >500 |
| MV1066 | 25.1 | >19 | 96.9 | >5 | >500 |

Example 24

Properties of MV1115.

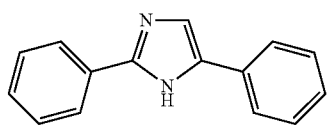

MV1115

For comparison purposes, the properties of MV1115 are provided. MV1115 has a solubility at pH 3 of 237 μM and at pH 7.4 of 175 μM. Chemical stability corresponds to 94% recovery after 24 h at pH 7.4 Metabolic stability corresponds to 87% recovery (CYP3A4, 1 hr). Passive permeability is 41.08 (not limiting). $IC_{50}$ (NaV1.6) is 32 μM. MV1115 shows the following in vivo data: $ED_{50}$ 61.7 and PI 2.0 (MES); $ED_{50}$ 160 (scM); $ED_{50}$ 47.2 and PI 2.7 (6 Hz); and 126 Tox.

Example 25

Properties of MV1118.

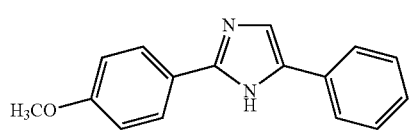

MV1118

For comparison purposes, the properties of MV1115 are provided. MV1115 has a solubility at pH 3 of 244 μM and at pH 7.4 of 117 μM. Chemical stability corresponds to 92% recovery after 24 h at pH 7.4 Metabolic stability corresponds to 92% recovery (CYP3A4, 1 hr). Passive permeability is 28.92 (not limiting). $IC_{50}$ (NaV1.6) is 20 μM. MV1118 shows the following in vivo data: $ED_{50}$ 46.8 and PI 4.8 (MES); $ED_{50}$ 142.2 and PI 1.57 (scM); $ED_{50}$ 52.2 and PI 4.3 (6 Hz); and 223 Tox.

We claim:

1. A method for treating a subject suffering from epilepsy, the method comprising administering to the subject a therapeutically effective amount of a compound according to Formula II, or a pharmaceutically acceptable salt, prodrug, tautomer, stereoisomer, hydrate, or solvate thereof:

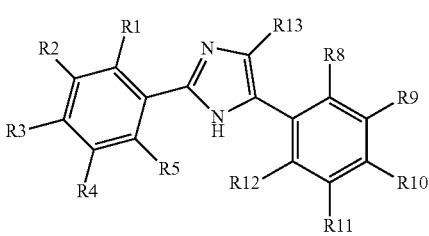

Formula II wherein
R1, R2, R3, R4, R5, R8 and R12 in each occurrence is independently H, $CH_3$, F, Cl, Br, I, $OCH_3$, $CF_3$, $OCF_3$, $NH_2$, COOH, CHO, OH, SH, $NO_2$, $COCH_3$, $CONH_2$, or $NHCOCH_3$;
R9, R10 and R11 each is independently H, $CH_3$, F, Cl, Br, I, $OCH_3$, $CF_3$, $OCF_3$, $NH_2$, COOH, CHO, OH, SH, $NO_2$, $COCH_3$, $CONH_2$, $NHCOCH_3$, or

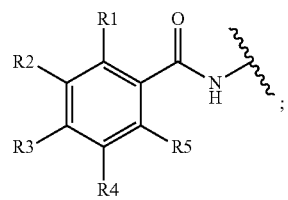

and
R13 is optionally substituted $C_1$-$C_6$ alkyl, optionally substituted $C_1$-$C_6$ haloalkyl, or halogen.

2. The method of claim 1, wherein R13 is optionally substituted $C_1$-$C_6$ alkyl.

3. The method of claim 2, wherein R13 is $CH_3$.

4. The method of claim 3, wherein the compound has the structure:

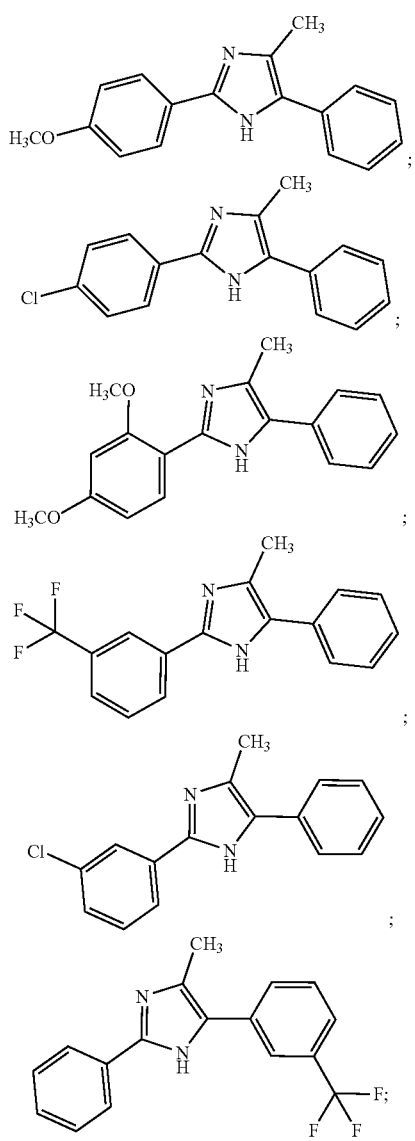
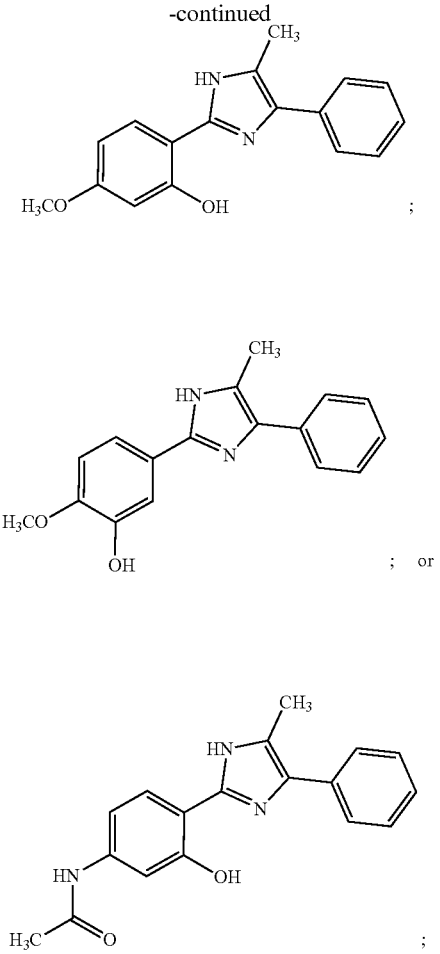
or a pharmaceutically acceptable salt, prodrug, tautomer, stereoisomer, hydrate, or solvate thereof.
5. The method of claim 1, wherein the epilepsy is partial epilepsy, generalized absence epilepsy, temporal lobe epilepsy or therapy resistant epilepsy.
* * * * *